US012336937B2

(12) United States Patent
Tedford et al.

(10) Patent No.: US 12,336,937 B2
(45) Date of Patent: Jun. 24, 2025

(54) MULTI-WAVELENGTH PHOTOTHERAPY DEVICES, SYSTEMS, AND METHODS FOR THE NON-INVASIVE TREATMENT OF DAMAGED OR DISEASED TISSUE

(71) Applicant: LumiThera, Inc., Poulsbo, WA (US)

(72) Inventors: Clark E Tedford, Poulsbo, WA (US); Scott DeLapp, San Diego, CA (US); Scott Bradley, San Marcos, CA (US)

(73) Assignee: LumiThera, Inc., Poulsbo, WA (US)

( * ) Notice: Subject to any disclaimer, the term of this patent is extended or adjusted under 35 U.S.C. 154(b) by 1010 days.

(21) Appl. No.: 17/109,063

(22) Filed: Dec. 1, 2020

(65) Prior Publication Data

US 2021/0315736 A1 Oct. 14, 2021

Related U.S. Application Data

(63) Continuation of application No. 14/956,366, filed on Dec. 1, 2015, now Pat. No. 10,881,550, which is a
(Continued)

(51) Int. Cl.
*A61F 9/007* (2006.01)
*A61N 5/06* (2006.01)
(Continued)

(52) U.S. Cl.
CPC .......... *A61F 9/0079* (2013.01); *A61N 5/0613* (2013.01); *A61N 5/0616* (2013.01);
(Continued)

(58) Field of Classification Search
CPC ......... A61F 9/0079; A61F 2009/00863; A61N 5/0613; A61N 5/0616; A61N 5/062;
(Continued)

(56) References Cited

U.S. PATENT DOCUMENTS 4,057,054 A 11/1977 Giannone
4,917,486 A 4/1990 Raven et al.
(Continued)

FOREIGN PATENT DOCUMENTS

CN 2453879 Y 10/2001
CN 101896144 A 11/2010
(Continued)

OTHER PUBLICATIONS

"Product Development," LumiThera, archived Aug. 20, 2014, URL= https://web.archive.org/web/20140820101900/https://www.lumithera.com:80/products/, download date Mar. 5, 2018. (2 pages).
(Continued)

*Primary Examiner* — Aaron F Roane
(74) *Attorney, Agent, or Firm* — Seed IP Law Group LLP

(57) ABSTRACT

Provided are multi-wavelength phototherapy devices, systems and methods for the treatment of a disorder or disease, including multi-wavelength low level light therapy ("PBM"), in particular to multi-wavelength PBM and other phototherapy systems and methods for improving functionality in and/or restoring functionality to a cell and/or tissue through the coordinated and targeted delivery to the cell or tissue of two or more doses of light having distinct wavelengths, wherein the two or more doses of light, when delivered in a coordinated fashion, can stimulate the activity of two or more light sensitive factors that, when activated, provide and/or enhance a desired target cell functionality. Ophthalmic phototherapy devices, systems, and treatment methods to expose an eye to selected multi-wavelengths of light to promote the healing of damaged or diseased eye tissue. The devices include a housing having an interior; an eyepiece disposed on the housing and configured and arranged for placement of an eye of the patient adjacent the eyepiece; a first light source producing a first light beam
(Continued)

having a first therapeutic wavelength and disposed within the housing; a second light source producing a second light beam having a second therapeutic wavelength and disposed within the housing, where the second therapeutic wavelength differs from the first therapeutic wavelength by at least 25 nm.

26 Claims, 34 Drawing Sheets

Related U.S. Application Data continuation-in-part of application No. PCT/US2015/049261, filed on Sep. 9, 2015.

(60) Provisional application No. 62/048,211, filed on Sep. 9, 2014, provisional application No. 62/048,187, filed on Sep. 9, 2014, provisional application No. 62/048,182, filed on Sep. 9, 2014.

(51) Int. Cl.
*A61F 9/008* (2006.01)
*A61N 5/067* (2006.01)

(52) U.S. Cl.
CPC ........... *A61N 5/062* (2013.01); *A61N 5/0622* (2013.01); *A61N 5/0624* (2013.01); *A61F 2009/00863* (2013.01); *A61N 2005/0643* (2013.01); *A61N 2005/0648* (2013.01); *A61N 2005/0651* (2013.01); *A61N 2005/0659* (2013.01); *A61N 2005/0662* (2013.01); *A61N 5/067* (2021.08)

(58) Field of Classification Search
CPC .... A61N 5/0622; A61N 5/0624; A61N 5/067; A61N 2005/0643; A61N 2005/0648; A61N 2005/0651; A61N 2005/0659; A61N 2005/0662
USPC .......................................................... 607/89
See application file for complete search history.

(56) References Cited

U.S. PATENT DOCUMENTS

| | | |
|---|---|---|
| 4,930,504 A | 6/1990 | Diamantopoulos et al. |
| 4,940,323 A | 7/1990 | Downing |
| 5,259,380 A | 11/1993 | Mendes et al. |
| 5,290,272 A | 3/1994 | Burstein et al. |
| 5,426,662 A | 6/1995 | Mefferd et al. |
| 5,447,527 A | 9/1995 | Waldman |
| 5,520,679 A | 5/1996 | Lin |
| 5,533,997 A | 7/1996 | Ruiz |
| 5,683,436 A | 11/1997 | Mendes et al. |
| 5,755,752 A | 5/1998 | Segal |
| 5,766,233 A | 6/1998 | Thiberg |
| 5,904,678 A | 5/1999 | Pop |
| 5,964,749 A | 10/1999 | Eckhouse et al. |
| 5,997,141 A | 12/1999 | Heacock |
| 6,019,754 A | 2/2000 | Kawesch |
| 6,235,014 B1 | 5/2001 | Abe et al. |
| 6,238,424 B1 | 5/2001 | Thiberg |
| 6,274,614 B1 | 8/2001 | Richter et al. |
| 6,283,956 B1 | 9/2001 | McDaniel |
| 6,287,296 B1 | 9/2001 | Seiler et al. |
| 6,319,273 B1 | 11/2001 | Chen et al. |
| 6,349,001 B1 | 2/2002 | Spitzer |
| 6,350,275 B1 | 2/2002 | Vreman et al. |
| 6,387,089 B1 | 5/2002 | Kreindel et al. |
| 6,443,976 B1 | 9/2002 | Flower et al. |
| 6,443,978 B1 | 9/2002 | Zharov |
| 6,471,716 B1 | 10/2002 | Pecukonis |
| 6,537,302 B1 | 3/2003 | Thiberg |
| 6,537,304 B1 | 3/2003 | Oron |
| 6,607,522 B1 | 8/2003 | Hamblin et al. |
| 6,676,655 B2 | 1/2004 | McDaniel |
| 6,677,366 B2 | 1/2004 | Richter et al. |
| 6,689,124 B1 | 2/2004 | Thiberg |
| 6,811,563 B2 | 11/2004 | Savage, Jr. et al. |
| 6,887,260 B1 | 5/2005 | McDaniel |
| 6,918,922 B2 | 7/2005 | Oron |
| 7,014,639 B2 | 3/2006 | Walneck et al. |
| 7,118,563 B2 | 10/2006 | Weckwerth et al. |
| 7,303,578 B2 | 12/2007 | De Taboada et al. |
| 7,309,348 B2 | 12/2007 | Streeter et al. |
| 7,354,432 B2 | 4/2008 | Eells et al. |
| 7,479,136 B2 | 1/2009 | Dotson |
| 7,534,255 B1 | 5/2009 | Streeter et al. |
| 7,695,504 B2 | 4/2010 | Anders et al. |
| 7,744,590 B2 | 6/2010 | Eells et al. |
| 7,914,523 B2 | 3/2011 | Barolet et al. |
| 7,919,094 B2 | 4/2011 | Schwaeble et al. |
| 8,025,687 B2 | 9/2011 | Streeter et al. |
| 8,106,038 B2 | 1/2012 | Margaron et al. |
| 8,167,921 B2 | 5/2012 | Streeter et al. |
| 8,308,784 B2 | 11/2012 | Streeter et al. |
| 8,471,967 B2 | 6/2013 | Miao et al. |
| 8,508,830 B1 | 8/2013 | Wang |
| 8,582,209 B1 | 11/2013 | Amirparviz |
| 8,705,177 B1 | 4/2014 | Miao |
| 8,956,396 B1 * | 2/2015 | Friend .................. A61N 5/0622 607/88 |
| 9,192,780 B2 | 11/2015 | McDaniel |
| 10,219,944 B2 | 3/2019 | Tedford et al. |
| 10,286,180 B2 | 5/2019 | Colbaugh |
| 10,596,037 B2 | 3/2020 | Tedford et al. |
| 10,881,550 B2 | 1/2021 | Tedford et al. |
| 2002/0004673 A1 | 1/2002 | Cho et al. |
| 2002/0087207 A1 | 7/2002 | Cho et al. |
| 2002/0173778 A1 | 11/2002 | Knopp et al. |
| 2002/0198575 A1 | 12/2002 | Sullivan |
| 2003/0004556 A1 | 1/2003 | McDaniel |
| 2003/0050674 A1 | 3/2003 | Joshi |
| 2003/0093135 A1 | 5/2003 | Denton et al. |
| 2004/0002694 A1 | 1/2004 | Pawlowski et al. |
| 2004/0008523 A1 | 1/2004 | Butler |
| 2004/0030370 A1 | 2/2004 | Lytle |
| 2004/0116909 A1 | 6/2004 | Neuberger et al. |
| 2004/0158234 A1 | 8/2004 | Previn et al. |
| 2004/0193234 A1 | 9/2004 | Butler |
| 2004/0215293 A1 | 10/2004 | Eells et al. |
| 2004/0243198 A1 | 12/2004 | Heacock et al. |
| 2005/0015120 A1 | 1/2005 | Seibel et al. |
| 2005/0055015 A1 | 3/2005 | Buzawa |
| 2005/0149150 A1 | 7/2005 | McDaniel |
| 2005/0159793 A1 | 7/2005 | Streeter |
| 2005/0203592 A1 | 9/2005 | Teichert |
| 2005/0234527 A1 | 10/2005 | Slatkine |
| 2005/0240168 A1 | 10/2005 | Neuberger et al. |
| 2006/0004306 A1 | 1/2006 | Altshuler et al. |
| 2006/0184214 A1 | 8/2006 | McDaniel |
| 2006/0235493 A1 | 10/2006 | Dotson |
| 2007/0123844 A1 | 5/2007 | Henry |
| 2007/0244526 A1 | 10/2007 | Zaghetto et al. |
| 2007/0252951 A1 | 11/2007 | Hammer et al. |
| 2008/0009839 A1 | 1/2008 | Dotson |
| 2008/0009922 A1 | 1/2008 | Bille |
| 2008/0015553 A1 | 1/2008 | Zacharias |
| 2008/0058783 A1 | 3/2008 | Altshuler et al. |
| 2008/0234668 A1 | 9/2008 | Linnik et al. |
| 2008/0246920 A1 | 10/2008 | Buczek |
| 2008/0269730 A1 | 10/2008 | Dotson |
| 2008/0269849 A1 | 10/2008 | Lewis |
| 2009/0062779 A1 | 3/2009 | Rizoiu et al. |
| 2009/0262308 A1 | 10/2009 | Ogawa |
| 2009/0309959 A1 | 12/2009 | Iwai et al. |
| 2010/0010592 A1 | 1/2010 | De Taboada et al. |
| 2010/0010594 A1 | 1/2010 | De Taboada et al. |
| 2010/0016783 A1 | 1/2010 | Bourke, Jr. et al. |
| 2010/0079356 A1 | 4/2010 | Hoellwarth |
| 2010/0079865 A1 | 4/2010 | Saarikko et al. |
| 2011/0098692 A1 | 4/2011 | Shazly et al. |

(56) References Cited

U.S. PATENT DOCUMENTS

| | | |
|---|---|---|
| 2011/0237999 A1 | 9/2011 | Muller et al. |
| 2011/0257467 A1 | 10/2011 | Clegg et al. |
| 2013/0009853 A1 | 1/2013 | Hesselink et al. |
| 2013/0023966 A1 | 1/2013 | Depfenhart et al. |
| 2013/0033756 A1 | 2/2013 | Spitzer et al. |
| 2013/0053929 A1 | 2/2013 | Colbaugh |
| 2013/0060187 A1 | 3/2013 | Friedman et al. |
| 2013/0069985 A1 | 3/2013 | Wong et al. |
| 2013/0079759 A1 | 3/2013 | Dotson et al. |
| 2013/0088413 A1 | 4/2013 | Raffle et al. |
| 2013/0100362 A1 | 4/2013 | Saeedi et al. |
| 2013/0103014 A1 | 4/2013 | Gooding et al. |
| 2013/0204235 A1 | 8/2013 | Palanker |
| 2013/0258270 A1 | 10/2013 | Cazalet et al. |
| 2014/0049451 A1* | 2/2014 | Sugiyama ............... G02B 27/01 345/8 |
| 2014/0128941 A1* | 5/2014 | Williams ............... H05B 45/00 315/193 |
| 2014/0171624 A1 | 6/2014 | Krammer et al. |
| 2014/0194957 A1 | 7/2014 | Rubinfeld et al. |
| 2014/0277292 A1* | 9/2014 | Steel ................... A61N 5/0618 607/88 |
| 2015/0231408 A1 | 8/2015 | Williams et al. |
| 2015/0234207 A1 | 8/2015 | Koifman |
| 2016/0067087 A1 | 3/2016 | Tedford et al. |

FOREIGN PATENT DOCUMENTS

| | | |
|---|---|---|
| CN | 201710538 U | 1/2011 |
| CN | 102271758 A | 12/2011 |
| CN | 102905750 A | 1/2013 |
| CN | 202682583 U | 1/2013 |
| EP | 1 829 496 A2 | 9/2007 |
| EP | 2 532 747 A1 | 12/2012 |
| JP | 2003-516830 A | 5/2003 |
| JP | 2006-101940 A | 4/2006 |
| JP | 2009-525141 A | 7/2009 |
| JP | 2013-521988 A | 6/2013 |
| JP | 2013-235256 A | 11/2013 |
| WO | 01/43825 A1 | 6/2001 |
| WO | 2004/105873 A1 | 12/2004 |
| WO | 2005/025672 A1 | 3/2005 |
| WO | 2007/092349 A2 | 8/2007 |
| WO | 2008/009062 A1 | 1/2008 |
| WO | 2008/131343 A1 | 10/2008 |
| WO | 2009/059730 A1 | 5/2009 |
| WO | 2011/116306 A2 | 9/2011 |
| WO | 2012/070054 A1 | 5/2012 |
| WO | 2012/167944 A1 | 12/2012 |
| WO | 2013/062654 A1 | 5/2013 |
| WO | 2013/148713 A1 | 10/2013 |
| WO | 2014/118571 A1 | 8/2014 |
| WO | 2016/040534 A1 | 3/2016 |

OTHER PUBLICATIONS

Barnstable et al., "Neuroprotective and antiangiogenic actions of PEDF in the eye: molecular targets and therapeutic potential," *Progress in Retinal and Eye Research* 23:561-577, 2004.

Begum et al., "Treatment with 670 nm Light Up Regulates Cytochrome C Oxidase Expression and Reduces Inflammation in an Age-Related Macular Degeneration Model," *PLoS One* 8(2), e57828, 2013. (11 pages).

Belevich et al., "Exploring the proton pump mechanism of cytochrome c oxidase in real time," *Proceedings of the National Academy of Sciences of the United States of America* 104(8):2685-2690, 2007.

Belevich et al., "Initiation of the proton pump of cytochrome c oxidase," *Proceedings of the National Academy of Sciences of the United States of America* 107(43):18469-18474, 2010.

Belevich et al., "Proton-coupled electron transfer drives the proton pump of cytochrome c oxidase," *Nature* 440(7085):829-832, 2006.

Brodeur, FLIP4, URL=www.spatrends.com/index, download date Mar. 1, 2005, 1 page.

Chung et al., "The Nuts and Bolts of Low-level Laser (Light) Therapy," *Annals of Biomedical Engineering* 40(2):516-533, 2012.

Damico et al., "New approaches and potential treatments for dry age-related macular degeneration," *Arquivos Brasileiros de Oftalmologia* 75(1):71-75, 2012.

Darlot et al., "Near-Infrared Light is Neuroprotective in a Monkey Model of Parkinson Disease," *Annals of Neurology* 79(1):59-75, 2016.

De Taboada et al., "Transcranial Laser Therapy Attenuates Amyloid-β Peptide Neuropathology in Amyloid-β Protein Precursor Transgenic Mice," *Journal of Alzheimer's Disease* 23(3):521-535, 2011.

Eells et al., "Mitochondrial signal transduction in accelerated wound and retinal healing by near-infrared light therapy," *Mitochondrion* 4(5-6):559-567, 2004.

English Translation of Office Action, mailed Sep. 3, 2019, for CN Application No. 201580055435.9, 14 pages.

English Translation of Office Action, dated Aug. 4, 2020, for Japanese Application No. 2019-201176, 3 pages.

Final Office Action, mailed Mar. 12, 2008, for U.S. Appl. No. 11/106,416, Dotson, "Ophthalmic Phototherapy Device and Associated Treatment Method," 8 pages.

Funk et al., "Outer Segments of Retinal Photoreceptors—A Review in the Light of Novel Findings," *Annual Research & Review in Biology* 4(16):2553-2565, 2014. (Abstract Only).

Gkotsi et al., "Recharging mitochondrial batteries in old eyes. Near infra-red increases ATP," *Experimental Eye Research* 122:50-53, 2014.

Glaser et al., "Retinal Pigment Epithelial Cells Release Inhibitors of Neovascularization," *Ophthalmology* 94:780-784, 1987.

Gorbikova et al., "The proton donor for O-O bond scission by cytochrome c oxidase," *Proceedings of the National Academy of Sciences of the United States of America* 105(31):10733-10737, 2008.

Grossman et al., "780 nm Low Power Diode Laser Irradiation Stimulates Proliferation of Keratinocyte Cultures: Involvement of Reactive Oxygen Species," *Lasers in Surgery and Medicine* 22:212-218, 1998.

Hamblin et al., "Mechanisms of Low Light Therapy," *Proc. of SPIE* 6140(614001): 2006, 12 pages.

Hashmi et al., "Role of Low-Level Laser Therapy in Neurorehabilitation," *PM&R* 2(12), (Supplement):S292-S305, 2010. (25 pages).

Huang et al., "Biphasic Dose Response in Low Level Light Therapy—An Update," *Dose-Response* 9(4):602-618, 2011.

Huang et al., "Biphasic Dose Response in Low Level Light Therapy," *Dose-Response* 7(4):358-383, 2009.

Huang et al., "Low-level laser therapy (810 nm) protects primary cortical neurons against excitotoxicity in vitro," *Journal of Biophotonics* 7(8):656-664, 2014.

Huang et al., "Low-level laser therapy (LLLT) reduces oxidative stress in primary cortical neurons in vitro," *J Biophotonics* 6(10):829-838, 2013.

International Organization for Standardization, "Ophthalmic instruments—Fundamental requirements and test methods—Part 2: Light hazard protection," ISO 15004-2:2007(E) first edition, 2007, 42 pages.

Ivandic et al., "Low-Level Laser Therapy Improves Vision in Patients with Age-Related Macular Degeneration," *Photomedicine and Laser Surgery* 26(3):241-245, 2008.

Jasaitis et al., "Nanosecond electron tunneling between the hemes in cytochrome $bo_3$," *Proceedings of the National Academy of Sciences of the United States of America* 104(52):20811-20814, 2007.

Johnstone et al., "The potential of light therapy in Parkinson's disease," *ChronoPhysiology and Therapy* 4:1-14, 2014.

Johnstone et al., "Turning on Lights to Stop Neurodegeneration: The Potential of Near Infrared Light Therapy in Alzheimer's and Parkinson's Disease," *Frontiers in Neuroscience* 9:Article 500, 2015. (15 pages).

Kaila et al., "Prevention of leak in the proton pump of cytochrome c oxidase," *Biochimica et Biophysica Acta* 1777(7-8):890-892, 2008.

Karu et al., "Exact Action Spectra for Cellular Responses Relevant to Phototherapy," *Photomedicine and Laser Surgery* 23(4):355-361, 2005.

(56) References Cited

OTHER PUBLICATIONS

Karu et al., "Cell Attachment to Extracellular Matrices in Modulated by Pulsed Radiation at 820 nm and Chemicals that Modify the Activity of Enzymes in the Plasma Membrane," *Lasers in Surgery and Medicine* 29:274-281, 2001.
Karu et al., "Cellular Effects of Low Power Laser Therapy Can be Mediated by Nitric Oxide," *Lasers in Surgery and Medicine* 36:307-314, 2005.
Karu et al., "Irradiation with He—Ne laser increases ATP level in cells cultivated in vitro," *Journal of Photochemistry and Photobiology B: Biology* 27:219-223, 1995.
Karu, "Mechanisms of Low-Power Laser Light Action on Cellular Level," *Proceedings of SPIE* 4159, 2000. (17 pages).
Kiire et al., "Subthreshold Micropulse Laser Therapy for Retinal Disorders," *Retina Today*, 2011, pp. 67-70.
Laakso et al. (ed.), *Proceedings of the 9th World Association for Laser Therapy Congress*, Foreword and Index, Gold Coast, Australia, Sep. 28-30, 2012, 6 pages.
Lane, "Power Games," *Nature* 443(7114):901-903, 2006.
Light Bioscience, "Gentlewaves LED Photomodulation Device," downloaded from http://www.lightbioscience.com/led_device.html on Mar. 1, 2005, 1 page.
Lim et al., "Probe pressure effects on human skin diffuse reflectance and fluorescence spectroscopy measurements," *Journal of Biomedical Optics* 16(1):011012, 2011, 9 pages.
Lisman et al., "Two Light-Induced Processes in the Photoreceptor Cells of Limulus Ventral Eye," *The Journal of General Physiology* 58:544-561, 1971.
Lubart et al., "Low Energy Laser Irradiation Promotes Cellular Redox Activity," *Photomedicine and Laser Surgery* 23(1):3-9, 2005. (15 pages).
LumiThera, "Photobiomodulation for eye diseases," Selected Abstracts, Aug. 21, 2013. (24 pages).
Masha et al., "Low-Intensity Laser Irradiation at 660 nm Stimulates Transcription of Genes Involved in the Electron Transport Chain," *Photomedicine and Laser Surgery* 31(2):47-53, 2013.
Merry et al., "Treatment of dry Age-related Macular Degeneration with Photobiomodulation," *Annual Meeting of the Association for Research in Vision and Ophthalmology*, Fort Lauderdale, FL, USA, May 6-9, 2012, 12 pages.
Miller et al., "The Role of Retinal Pigment Epithelium on the Involution of Subretinal Neovascularization," *Invest Ophthalmol Vis Sci.* 27(11):1644-1652, 1986.
Moro et al., "Photobiomodulation preserves behaviour and midbrain dopaminergic cells from MPTP toxicity: evidence from two mouse strains," *BMC Neuroscience* 14:Article 40, 2013. (9 pages).
Murphy et al., "Toward the discrimination of early melanoma from common and dysplastic nevus using fiber optic diffuse reflectance spectroscopy," *Journal of Biomedical Optics* 10(6):064020, 2005, 9 pages.
Office Action, mailed Apr. 3, 2007, for U.S. Appl. No. 11/106,416, Dotson, "Ophthalmic Phototherapy Device and Associated Treatment Method," 10 pages.
Office Action, mailed Feb. 25, 2008, for U.S. Appl. No. 11/858,351, Dotson, "Ophthalmic Phototherapy Treatment Method," 12 pages.
Office Action, mailed Jan. 14, 2015, for U.S. Appl. No. 13/679,557, Dotson et al., "Ophthalmic Phototherapy Device and Associated Treatment Method," 29 pages.
Office Action, mailed May 23, 2012, for U.S. Appl. No. 12/172,697, Dotson, "Ophthalmic Phototherapy Device and Associated Treatment Method," 31 pages.
Office Action, mailed Jan. 30, 2020, for Mexican Application No. MX/a/2017/003012, 5 pages. (w/ English Translation).
Office Action, mailed Jan. 22, 2020, for New Zealand Application No. 730040, 6 pages.
Ogata et al., "Upregulation of Pigment Epithelium-Derived Factor after Laser Photocoagulation," *American Journal of Ophthalmology* 132(3):427-429.

Oron et al., "Low-level laser therapy applied transcranially to mice following traumatic brain injury significantly reduces long-term neurological deficits," *Journal of Neurotrauma* 24(4):651-656, 2007. (Abstract Only).
Purushothuman et al., "Photobiomodulation with near infrared light mitigates Alzheimer's disease-related pathology in cerebral cortex—evidence from two transgenic mouse models," *Alzheimer's Research & Therapy* 6(2), 2014. (13 pages).
Riverside Facial Plastic Surgery and Sinus Center, Gentlewaves LED Photomodulation Fact Sheet, URL=http://www.riversideface.com/pages/gentlewaves.html, download date Mar. 9, 2015. (4 pages).
Robotic LED Skin Rejuvenation, FLIP4, URL=www.medspafinancing.com/new.html, download date Mar. 1, 2005, 1 page.
Rodríguez-Santana et al., "Laser Photobiomodulation as a Potential Multi-Hallmark Therapy for Age-Related Macular Degeneration," *Photomedicine and Laser Surgery* 31(9):409-410, 2013.
Rojas et al., "Low-level light therapy of the eye and brain," *Eye and Brain* 3:49-67, 2011.
Sharma et al., "Dose Response Effects of 810 nm Laser Light on Mouse Primary Cortical Neurons," *Lasers in Surgery and Medicine* 43(8):851-859, 2011. (16 pages).
Siletsky et al., "Time-resolved single-turnover of $ba_3$ oxidase from *Thermus thermophilus*," *Biochimica et Biophysica Acta* 1767(12):1383-1392, 2007.
Sommer et al., "Biostimulatory Windows in Low-Intensity Laser Activation: Lasers, Scanners, and NASA's Light-Emitting Diode Array System," *Journal of Clinical Laser Medicine & Surgery* 19(1):29-33, 2001.
Tang et al., "Low-Intensity Far-Red Light Inhibits Early Lesions That Contribute to Diabetic Retinopathy: In Vivo and In Vitro," *Investigative Ophthalmology & Visual Science* 54(5):3681-3690, 2013.
Tang et al., "Predicting complications with pretreatment testing in infantile haemangioma treated with oral propranolol," *British Journal of Ophthalmology* 100(7):902-906, 2016.
Tarita-Nistor et al., "Fixation Characteristics of Patients with Macular Degeneration Recorded with the MP-1 Microperimeter," *Retina* 28(1):125-133, 2008. (Abstract Only).
Tata et al., "Laser therapy: A review of its mechanism of action and potential medical applications," *Laser Photonics Rev.* 5(1):1-12, 2011.
Tedford et al., "Devices and Methods for Non-Invasive Multi-Wavelength Low Level Light Therapy for Ocular Treatments," U.S. Appl. No. 62/048,182, filed Sep. 9, 2014, 51 pages.
Tedford et al., "Wearable Devices and Methods for Multi-Wavelength Low Level Light Therapy for Ocular Treatments," U.S. Appl. No. 62/048,187, filed Sep. 9, 2014, 55 pages.
Tosk, "FDA Clears Gentle Waves: The First and Only Light Emitting Diode Device for the Treatment of Periorbital Wrinkles and Rhytids," URL=http://www.drmcdaniel.com/fda-clears-gentlewaves, download date Mar. 9, 2015, 2 pages.
Tuchin, *Tissue Optics: Light Scattering Methods and Instruments for Medical Diagnosis*, The International Society for Optical Engineering, Bellingham, WA, USA, 2000, pp. 1-11.
Van Breugal et al., "Power Density and Exposure Time of He—Ne Laser Irradiation are More Important Than Total Energy Dose in Photo-Biomodulation of Human Fibroblasts In Vitro," *Lasers in Surgery and Medicine* 12(1):528-537, 1992.
Wells et al., "Biophysical mechanisms responsible for pulsed low-level laser excitation of neural tissue," *Proc of SPIE* 6084:60840X-1-60840X-7, 2006, 7 pages.
Wong-Riley et al., "Photobiomodulation Directly Benefits Primary Neurons Functionally Inactivated by Toxins," *The Journal of Biological Chemistry* 280(6):4761-4771, 2005.
Xuan et al., "Transcranial Low-Level Laser Therapy Improves Neurological Performance in Traumatic Brain Injury in Mice: Effect of Treatment Repetition Regimen," *PLoS One* 8(1), e53454, 2013. (9 pages).
Anders, J. J. et al., "Low-Level Light/Laser Therapy Versus Photobiomodulation Therapy", Photomedicine and Laser Surgery, vol. 33, No. 4, 2015, 2 pages.

(56) References Cited

OTHER PUBLICATIONS

Anders, J. J. et al., "Light-Emitting Diode Therapy and Low-Level Light Therapy are Photobiomodulation Therapy", Photobiomodulation, Photomedicine, and Laser Surgery, vol. 37, No. 2, 2019, 3 pages.
Notice of Grounds for Preliminary Rejection for KR Application No. 10-2017-7009408, dated Nov. 29, 2022, 19 pages.

\* cited by examiner

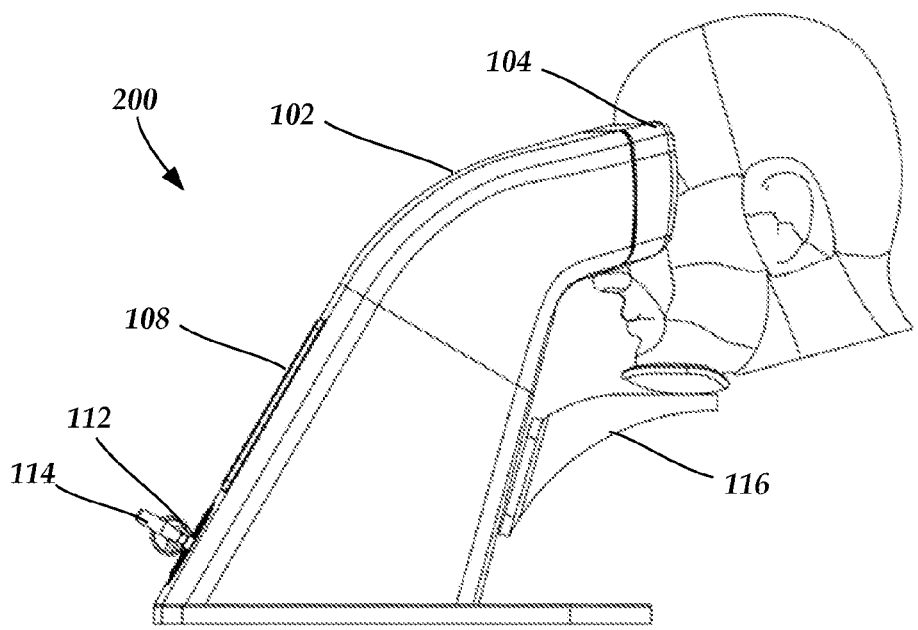
FIG. 2
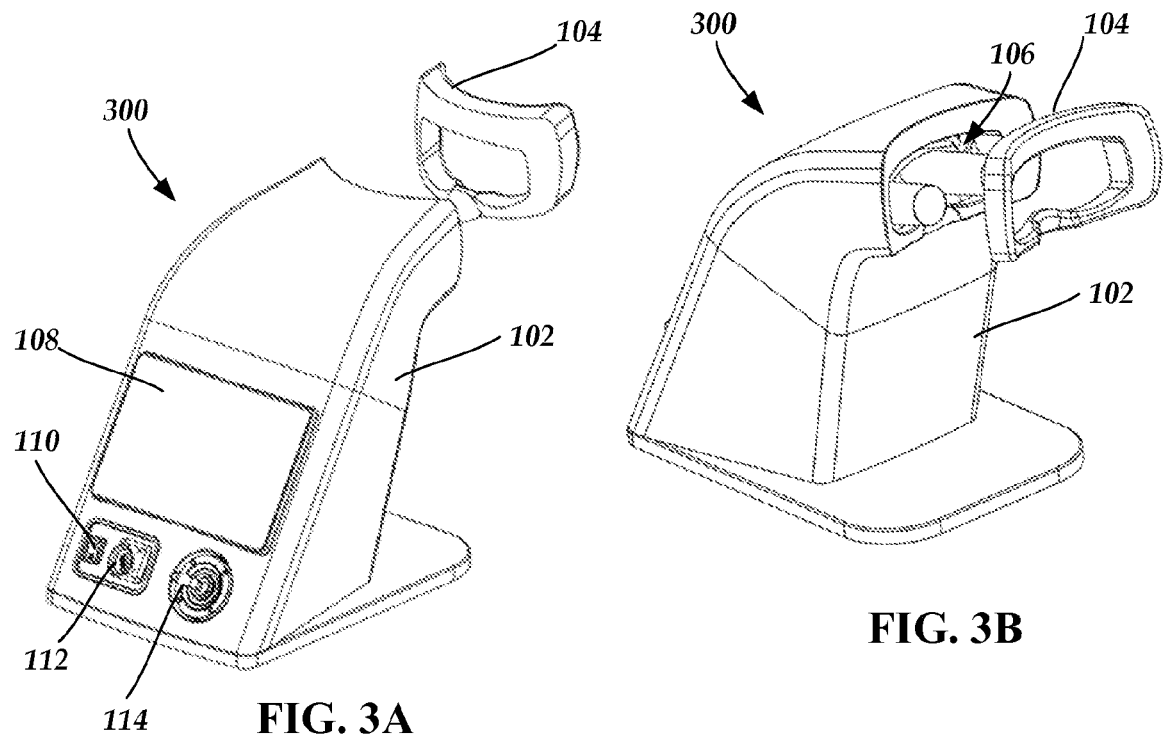
FIG. 3A
FIG. 3B

FIG. 23

| Group | Mean | S.D. (+/-) |
|---|---|---|
| Visual Acuity @ Baseline (letter score) | 41.29 | 11.36 |
| Visual Acuity @ 3 weeks (letter score) | 47.32 | 11.29 |
| Visual Acuity @ 3 months (letter score) | 50.050 | 6.353 |
| Contrast Sensitivity @ Baseline (log) | 1.503 | 0.229 |
| Contrast Sensitivity @ 3 weeks (log) | 1.605 | 0.243 |
| Contrast Sensitivity @ 3 weeks (log) | 1.664 | 0.181 |
| Central Drusen @ Baseline (volume) | 0.460 | 0.144 |
| Central Drusen @ 3 weeks (volume) | 0.445 | 0.169 |
| Central Drusen @ 3 months (volume) | 0.431 | 0.039 |

MULTI-WAVELENGTH PHOTOTHERAPY DEVICES, SYSTEMS, AND METHODS FOR THE NON-INVASIVE TREATMENT OF DAMAGED OR DISEASED TISSUE

CROSS-REFERENCE TO RELATED APPLICATIONS

This U.S. Non-provisional Patent Application claims priority as a continuation from U.S. Non-provisional application Ser. No. 14/956,366, which was filed on Dec. 1, 2015, which claims priority as a continuation-in-part from PCT Patent Application No. PCT/US2015/049261, which was filed on Sep. 9, 2015, which claims the benefit of U.S. Provisional Patent Application Nos. 62/048,182, 62/048,187, and 62/048,211, each of which was filed on Sep. 9, 2014. All of the above-identified applications are incorporated herein by reference in their entirety.

BACKGROUND OF THE DISCLOSURE

Technical Field

The present disclosure relates, generally, to multi-wavelength phototherapy, including multi-wavelength photobiomodulation ("PBM"). More specifically, disclosed herein are non-invasive phototherapy devices, systems, and methods, including ophthalmic phototherapy devices, systems, and methods, for improving functionality in and/or restoring functionality to a cell and/or tissue, such as a damaged or diseased eye cell or tissue, through the coordinated and targeted delivery to the cell or tissue of two or more doses of light each having a distinct wavelength peak, wherein the two or more doses of light, when delivered in a coordinated fashion, modulate the activity of two or more light sensitive factors or photoacceptors that, when activated, can enhance or inhibit a desired target cell functionality. The present disclosure also concerns the treatment of disorders and/or diseases that are associated with an absence and/or diminished functionality in a cell of a patient afflicted with the disorder and/or disease. The multi-wavelength phototherapy systems and methods disclosed herein can, therefore, be adapted for therapeutic use by the coordinated and targeted delivery of two or more distinct wavelengths of light to a cell or tissue in a patient afflicted with a disorder or disease to enhance a diminished functionality, reduce a hyperactive functionality, or correct an altered functionality in a cell or tissue that is associated with the disorder or disease thereby reducing the symptoms or slowing the progression of one or more aspect of the disorder and/or disease to, thereby, promote the healing of a damaged or diseased cell or tissue.

Description of the Related Art

Light can act on different mechanisms within cellular tissue to stimulate or suppress biological activity in a process commonly referred to herein as photobiomodulation ("PBM") or low level light therapy. PBM involves the use of visible light to near infrared light (NIR) (500-1000 nm) produced by a laser or a non-coherent light source applied to the surface of the body to produce beneficial effects in a wide range of disease states. Chung et al., *Ann. Biomed. Eng* (2011); Hashmi et al., *PM. R.* 2: S292-S305 (2010); Rojas et al., *Dovepress* 2011:49-67 (2011); and Tata and Waynant, *Laser and Photonics Reviews* 5:1-12 (2010). PBM requires the use of light with a suitable intensity, energy, and wavelengths, without significantly causing damage to the cells.

The mechanism of PBM at the cellular level has been ascribed to the activation of mitochondrial respiratory chain components resulting in stabilization of metabolic function. A growing body of evidence suggests that cytochrome C oxidase (CCO) is a key photoacceptor of light in the far red to near infrared spectral range. Grossman et al., *Lasers. Surg. Med.* 22:212-218 (1998); Karu et al., *J. Photochem. Photobiol. B.* 27:219-223 (1995); Karu and Kolyakov, *Photomed. Laser Surg.* 23:355-361 (2005); Karu et al., *Lasers Surg. Med.* 36:307-314 (2005); and Wong-Riley et al., *J. Biol. Chem.* 280:4761-4771 (2005).

There are many disorders including trauma or diseases that can afflict the eye. Ocular disease can include, for example, glaucoma, age-related macular degeneration, diabetic retinopathy, retinitis pigmentosa, central serous retinopathy (CRS), non-arteritic anterior ischemic optic neuropathy (NAION), Leber's hereditary optic neuropathy disease, uveitis, and the like. Other disorders can include physical trauma (e.g., cataract or lens surgery) or other sources of ocular damage or degeneration. Ocular degeneration can include the process of cell destruction resulting from a primary destructive event such as ocular trauma or surgery, as well as from secondary, delayed and progressive destructive mechanisms that are invoked by cells due to the occurrence of a primary destructive or disease event.

It is desirable to develop methods and devices for treatment of these ocular diseases, disorders, or degeneration. In particular, it is desirable to develop methods and devices for treatment that may be less invasive or have fewer side effects than surgery or pharmacological treatments or which can be used in conjunction with surgery or pharmacological treatments to aid in healing or treatment.

SUMMARY OF THE DISCLOSURE

The present disclosure provides multi-wavelength phototherapy devices, systems, and methods for use in the non-invasive treatment of disorders or diseases that are associated with an absent or diminished cell or tissue functionality. The multi-wavelength phototherapy devices, systems, and methods disclosed herein can, therefore, be adapted for therapeutic use by the coordinated and targeted delivery of two or more distinct wavelengths of light to a cell or tissue in a patient afflicted with a disorder or disease to enhance a diminished functionality, reduce a hyperactive functionality, or correct an altered functionality in a cell or tissue that is associated with the disorder or disease thereby reducing the symptoms or slowing the progression of one or more aspect of the disorder or disease.

Within certain embodiments, the present disclosure provides multi-wavelength phototherapy devices, systems, and methods for improving and/or restoring one or more functionality of a target cell, which systems and methods include the coordinated and targeted delivery to a cell and/or tissue of two or more distinct wavelengths of light to stimulate the activity of two or more light sensitive factors or photoacceptors thereby improving and/or restoring target cell functionality, in particular a functionality of a target cell that is associated with a disorder and/or disease.

Within other embodiments, the present disclosure provides multi-wavelength phototherapy devices, systems, and methods for stimulating cytochrome c oxidase (CCO) activity in a cell and/or tissue, which methods include the coordinated and targeted delivery of two or more doses of light to a cell having two or more light sensitive factors that are associated with, and necessary for, CCO activity, wherein a first light dose has a first wavelength that can activate a first light sensitive factor in CCO and a second light dose has a second wavelength that can activate a second light sensitive factor in CCO thereby stimulating CCO activity. Within certain aspects of these embodiments, stimulating CCO activity improves and/or restores the functionality of a target cell, in particular a target cell within a target tissue, such as a target tissue having one or more cell that is associated with a disorder and/or disease, certain aspects of which can be reversed and/or the progression of which can be slowed by increasing intracellular CCO activity.

Within further embodiments, the present disclosure provides multi-wavelength phototherapy devices, systems, and methods for the treatment of a patient afflicted with a disorder and/or a disease that is associated with one or more absent or diminished cellular functionality, wherein the systems and methods include the coordinated and targeted delivery of two or more distinct wavelengths of light to one or more cells in the patient to restore the absent cellular functionality and/or enhance the diminished cellular functionality thereby treating the disorder and/or disease. Within certain aspects of these embodiments, the absent or diminished cellular functionality includes an intracellular functionality, such as intracellular CCO activity, which in a target cell having two or more light sensitive factors that are associated with, and necessary for, the intracellular functionality.

Within yet other embodiments, the present disclosure provides multi-wavelength phototherapy devices, systems, and methods for the treatment of a patient afflicted with an ocular disorder and/or a disease that is associated with one or more absent and/or diminished functionality in an ocular cell, the systems and methods including the coordinated and targeted delivery of two or more distinct wavelengths of light to an eye in the patient to restore and or enhance the absent and/or diminished functionality to the ocular cell thereby treating the ocular disorder and/or disease.

Within certain aspects of these devices, systems, and methods the ocular disorder and/or disease is an acute or chronic ocular disorder and/or disease, which includes, for example, an ocular degenerating disease, such as blurred or loss of vision, visual acuity impairment, inflammation, and deterioration in contrast sensitivity.

Within other aspects of these devices, systems, and methods the ocular disorder and/or disease is an ocular syndrome such as, for example, glaucoma, age-related macular degeneration (AMD) including either dry or wet, diabetic retinopathy, retinitis pigmentosa, CRS, NAION, Leber's disease, ocular surgery, uveitis, hypertensive retinopathy, or a process that interferes with one or more function of an eye via a vascular or neurological mechanism, and optic neuritis.

Within further aspects of these devices, systems, and methods the ocular disorder and/or disease is an acute or chronic ocular eyelid disease including bleparitis, periorbital wrinkles, seborrhea, or other eyelid skin condition such as, for example, psoriasis and eczema.

Within yet other aspects of these devices, systems, and methods the ocular disorder and/or disease is an acute or chronic ocular conjunctiva or corneal disease including an acute injury such as exposure keratitis or UV keratitis, dry eyes, viral infections, bacterial infections, corneal abrasions, corneal edema, surgical incisions, perforating injuries, episcleritis or scleritis.

Within still further aspects of these devices, systems, and methods the ocular disorder and/or disease is an acute or chronic anterior chamber and vitreous disease including iritis, vitritis, endophthalmitis (bacterial and sterile).

In at least some embodiments, an apparatus adapted to provide PBM therapy to a subject experiencing symptoms associated with one or more ocular disorders or disease or a subject who has been diagnosed with one or more ocular disorders or disease through the eye of the subject either with the open or closed eyelid, sclera or any angle approach that provides for access to the target tissues. The apparatus can include a controller that can operate in a standalone, independent manner, or in response to a signal from a remote control. The controller can activate one or more light sources adapted to delivery light to the subject's ocular tissue.

In at least some embodiments, the devices, systems, and methods described herein can be used to treat, or otherwise improve the resultant effects of ocular conditions, such as acute or chronic ocular diseases, or the symptoms associated with such ocular conditions. In at least some embodiments, the devices, systems, and methods described herein can be used to treat or otherwise improve the symptoms or effects associated with ocular degenerating diseases, such as blurred or loss of vision, visual acuity impairment, inflammation, ischemia, anatomical deposits, (e.g., lipofusion, b-amyloid or drusen) and deterioration in contrast sensitivity.

In accordance with several embodiments, the devices, systems, and methods described herein are used to treat, or otherwise address subjects having, or experiencing symptoms of acute or chronic ocular syndromes (e.g., glaucoma, dry or wet age-related macular degeneration (AMD), diabetic retinopathy, retinitis pigmentosa, central serous retinopathy (CRS), non-arteritic anterior ischemic optic neuropathy (NAION), Leber's disease, ocular surgery, uveitis, hypertensive retinopathy, or any process that interferes with function via vascular or neurological mechanism, and optic neuritis.

The devices, systems, and methods described herein can also be used to treat, or otherwise address subjects having acute and chronic ocular eyelid disease including bleparitis, periorbital wrinkles, seborrhea and other eyelid skin conditions i.e., psoriasis, eczema, etc. The apparatuses and methods described herein can also be used to treat, or otherwise address subjects having acute and chronic ocular conjunctiva and corneal disease including any acute injuries such as exposure keratitis or UV keratitis, dry eyes, viral infections, bacterial infections, corneal abrasions, corneal oedema, surgical incisions, perforating injuries, episcleritis and scleritis. The devices, systems, and methods described herein can also be used to treat, or otherwise address subjects having acute and chronic anterior chamber and vitreous disease including iritis, vitritis, endophthalmitis (bacterial and sterile). Categories are generally determined based on the area affected or on the etiology and it should be appreciated that some disorders, diseases, or conditions can overlap between two or more categories.

In one embodiment, the present disclosure provides a self-standing device for delivery of light therapy to ocular tissue of an eye of a patient. The device includes a housing having an interior; an eyepiece disposed on the housing and configured and arranged for placement of an eye of the patient adjacent the eyepiece; a first light source producing a first light beam having a first therapeutic wavelength and disposed within the housing; a second light source producing a second light beam having a second therapeutic wavelength and disposed within the housing where the second therapeutic wavelength differs from the first therapeutic wavelength by at least 25 nm; and an aperture disposed within the housing. The device is configured and arranged to direct the first and second light beams through the aperture and through the eyepiece to provide light therapy to the eye of the patient.

In another embodiment, the present disclosure provides a self-standing device for delivery of light therapy to ocular tissue of an eye of a patient. The device includes a housing having an interior; an eyepiece disposed on the housing and configured and arranged for placement of an eye of the patient adjacent the eyepiece; a first light source producing a first light beam having a first therapeutic wavelength and disposed within the housing; a second light source producing a second light beam having a second therapeutic wavelength and disposed within the housing where the second therapeutic wavelength differs from the first therapeutic wavelength by at least 25 nm; and a reflective filter disposed within the housing and configured and arranged to substantially pass light having the first therapeutic wavelength and substantially reflect light having the second therapeutic wavelength. The device is configured and arranged to direct the first and second light beams to the reflective filter and then through the eyepiece to provide light therapy to the eye of the patient.

Within other embodiments, the present disclosure provides wearable devices for delivery of PBM therapy to ocular tissue of an eye of a patient. Such wearable devices include a frame comprising a front piece and two earpieces extending from the front piece; a first light source producing a first light beam having a first therapeutic wavelength and disposed within or on the frame; and a second light source producing a second light beam having a second therapeutic wavelength and disposed within or on the frame, where the second therapeutic wavelength differs from the first therapeutic wavelength by at least 25 nm. At least a portion of the first and second light beams are directed toward the eye of the patient when the patient is wearing the wearable device.

A related embodiment is a wearable device for delivery of PBM therapy to ocular tissue of an eye of a patient. The device includes a frame comprising a front piece and two earpieces extending from the front piece; at least one light source producing a light beam having a therapeutic wavelength and disposed within the frame; a spatial light modulator disposed within the frame and positioned to receive the light beam and to modulate the light beam to generate a modulated light beam; and a light directing element to receive the modulated light beam and direct at least a portion of the modulated light beam to the eye of the patient when the patient is wearing the device.

In further embodiments, the present disclosure provides methods of providing light therapy to ocular tissue of a patient using any of the apparatuses, devices, or systems described herein. In certain aspects, the methods include placing at least one eye of the patient at the eyepiece of the device; and directing light of at least one of the first therapeutic wavelength or the second therapeutic wavelength from device to the at least one eye of the patient to produce a therapeutic effect. In other aspects, the methods include placing the wearable device on the patient; and directing light of at least one of the first therapeutic wavelength or the second therapeutic wavelength from device to the at least one eye of the patient to produce a therapeutic effect.

BRIEF DESCRIPTION OF THE DRAWINGS

These and other aspects of the present disclosure will be best understood in conjunction with the following drawings, which exemplify certain aspects of the various embodiments.

FIG. 2 is a side view of one embodiment of a second embodiment of an opthalmic phototherapy device with a chin rest, according to the present disclosure.

FIG. 3A is a perspective back view of a third embodiment of an opthalmic phototherapy device with a removable patient interface surface, according to the present disclosure.

FIG. 3B is a perspective side view of the opthalmic phototherapy device of FIG. 3A, according to the present disclosure.

FIG. 23 is a table summarizing mean visual acuity, contrast sensitivity, and central Drusen at baseline, three weeks, and after three months of PBM therapy. Data presented are a mean from the patient population+/−a standard deviation (S.D.).

DETAILED DESCRIPTION

Figure 1A:
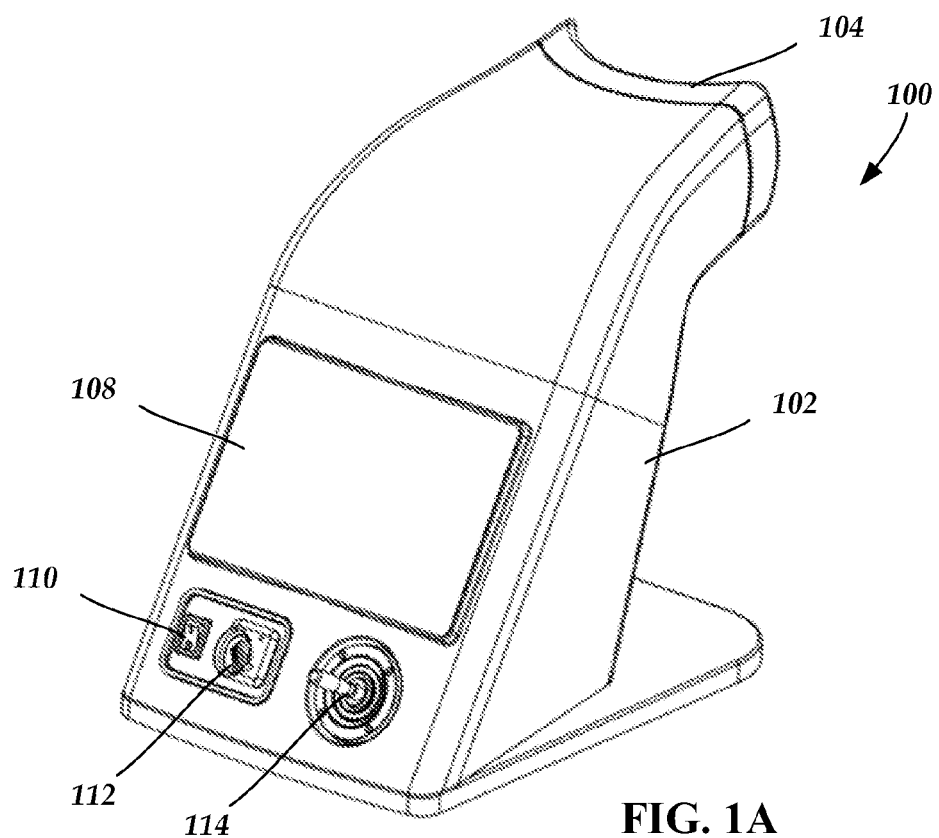
FIG. 1A is a perspective back view of one embodiment of an opthalmic phototherapy device, according to the present disclosure.
Figure 1B:
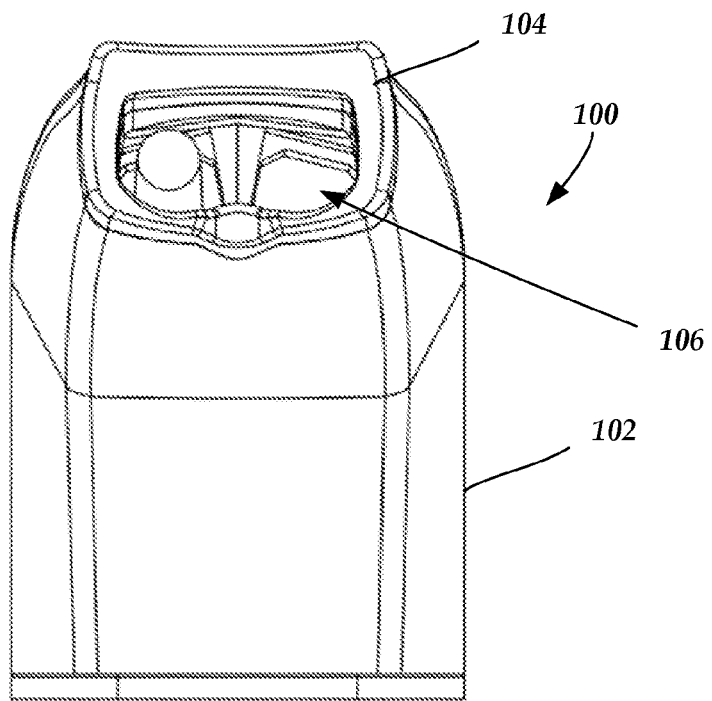
FIG. 1B is a front view of the opthalmic phototherapy device of FIG. 1A, according to the present disclosure.
Figure 1C:
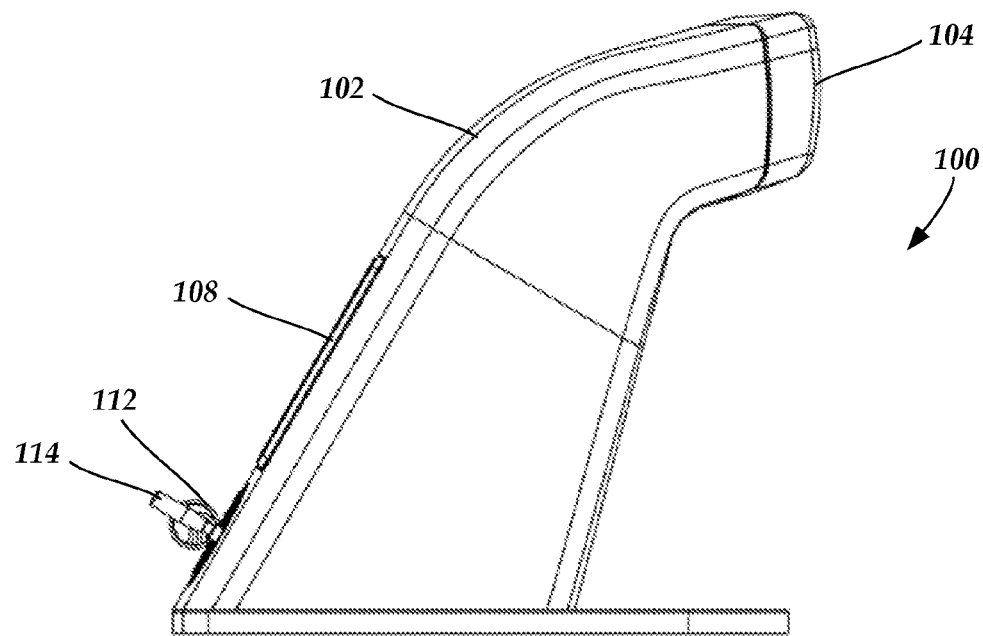
FIG. 1C is a side view of the opthalmic phototherapy device of FIG. 1A, according to the present disclosure.
Figure 1D:
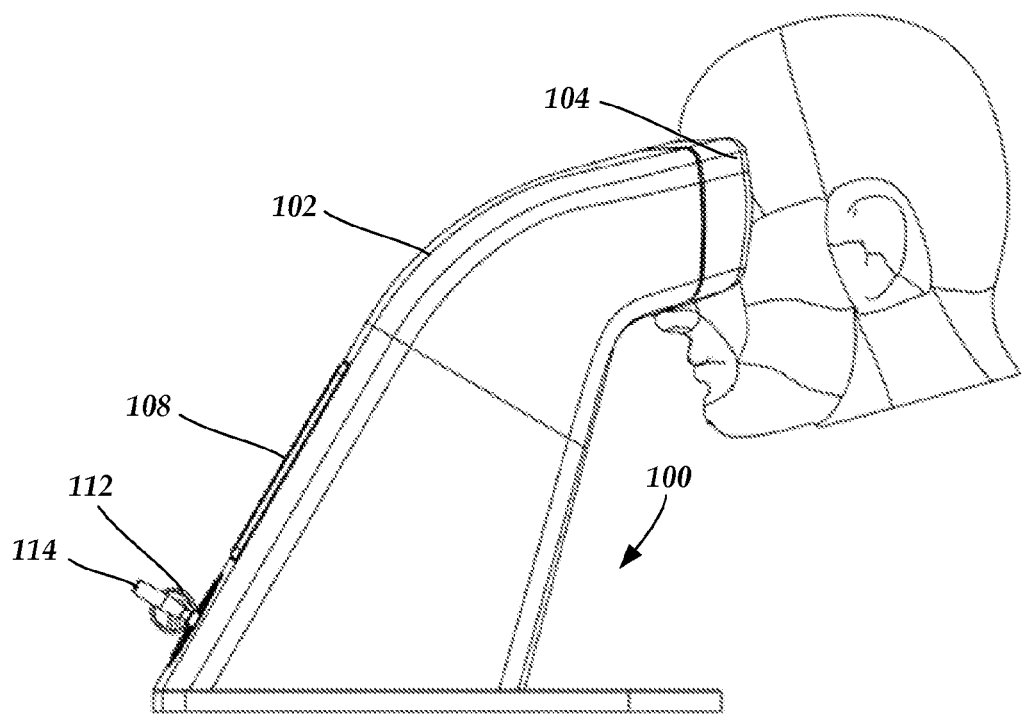
FIG. 1D is a side view of the opthalmic phototherapy device of FIG. 1A with a patient, according to the present disclosure.

The multi-wavelength phototherapy devices, systems and methods, which are described in further detail herein, are based upon the discovery that certain cellular responses, including cellular responses within a damaged and/or diseased tissue, can be promoted through the coordinated and targeted delivery to a cell of light having two distinct wavelengths, wherein a first dose of light having a first wavelength (or range of wavelengths) can stimulate a first intracellular activity and a second dose of light having a second wavelength (or range of wavelengths) can stimulate a second intracellular activity. Moreover, certain therapeutic benefits can be achieved in a patient afflicted with a damaged and/or diseased tissue by promoting a desired cellular response that contributes to the healing of a damaged tissue and/or reversal or slowing of disease progression in a diseased tissue.

Photobiomodulation ("PBM") is a non-invasive form of low level light therapy ("PBM") that involves the therapeutic administration of light energy to a subject (e.g., a human or animal) at lower irradiances than those used for cutting, cauterizing, or ablating biological tissue, resulting in desirable photobiomodulatory effects while leaving tissue undamaged. In non-invasive phototherapy, it is desirable to apply an efficacious amount of light energy to the internal tissue to be treated using light sources positioned outside the body. (See, e.g., U.S. Pat. Nos. 6,537,304 and 6,918,922, both of which are incorporated in their entireties by reference herein.)

Therapeutic benefits can be achieved for a patient afflicted with damaged and/or diseased tissue by promoting one or more cellular responses within a cell of a damaged and/or diseased tissue, which cellular responses can be promoted through the coordinated and targeted delivery of two or more doses of light, wherein a first dose of light has a first wavelength or range of wavelengths, which can stimulate a first intracellular activity, and a second dose of light has a second wavelength or range of wavelengths, which can stimulate a second intracellular activity, wherein the coordinated stimulation of the first and second intracellular activities promotes a desired cellular response thereby facilitating healing of the damaged tissue and/or reversing or slowing disease progression in the diseased tissue.

In the non- or minimally-invasive multi-wavelength phototherapy devices, systems, and methods disclosed herein, an efficacious amount of light energy is delivered to an internal tissue, as exemplified herein by an ocular tissue, from one or more light sources that are: (1) exterior to the body (i.e., non-invasive) or that is in a subcutaneous location within the body (i.e., minimally-invasive) and (2) capable of producing light having a distinct and specified wavelength and/or range of wavelengths. In particular, the multi-wavelength phototherapy systems and methods disclosed herein employ light having a first wavelength or range of wavelengths that can stimulate a first light sensitive factor and light having a second wavelength or range of wavelengths that can stimulate a second light sensitive factor, wherein the targeted and coordinated delivery of light having a first wavelength and light having a second wavelength promotes a cellular response within a targeted tissue thereby facilitating the healing of the damaged tissue and/or reversing or slowing the progression of disease in the diseased tissue.

As described in further detail herein, such multi-wavelength phototherapy devices, systems, and methods provide a therapeutic benefit when delivered alone, which therapeutic benefit can be further enhanced when those systems and methods are used in combination with one or more small molecule drug and/or biologic and/or when used in combination with a second therapeutically suitable device and/or other treatment regimen, which drugs, biologics, devices, and/or treatment regimen can be administered to a patient prior to, concurrently with, and/or subsequent to the targeted and coordinated delivery of the multi-wavelength phototherapy.

Light exhibiting a single wavelength or range of wavelengths such as, for example, red light having a wavelength of 600-700 nm or near-infrared light ("NIR") having a wavelength of 800-900 nm can be used to stimulate mitochondrial cytochrome c oxidase ("CCO") enzymatic activity. As disclosed herein, the targeted and coordinated use of two or more sources of light, each light source having a distinct wavelength and intensity, can yield a unique, additive, or synergistic therapeutic benefit that is substantially improved. Within some aspects, the therapeutic benefit may be greater than simply the therapeutic benefit exhibited by each wavelength of light when delivered in isolation and/or when delivered in a non-targeted, non-coordinated fashion to the cell and/or tissue of interest.

More specifically, distinct wavelengths of light can, for example, stimulate structurally and functionally distinct moieties within a protein of a target cell, such as the CuA and CuB moieties of a mitochondrial cytochrome c oxidase ("CCO"). It is recognized as part of the present disclosure that by coordinating temporally the delivery of two or more wavelengths of light to the CuA and CuB moieties of a mitochondrial CCO, the electron flow and oxygen binding via the CCO enzyme can be independently, sequentially, or in combination optimized to: (a) substantially improve overall CCO activity, (b) restore mitochondrial membrane potential ("MMP"), and (c) increase the level of ATP synthesis. Moreover, such temporally coordinated and targeted delivery of multiple wavelengths of light substantially improves the therapeutic efficacy of previously-described, single wavelength phototherapy systems and methods.

The multi-wavelength phototherapy devices, systems and methods of the present disclosure can, therefore, be used advantageously to restore mitochondrial membrane potential (MMP) and/or to increase ATP formation in a damaged and/or diseased tissue, which damaged and/or diseased tissue exhibits a characteristic reduction in its access to oxygen.

As described in further detail herein, the present disclosure contemplates, for example, the targeted and coordinated delivery of light having a wavelength of from about 640 nm to about 700 nm to activate a CCO CuB moiety thereby displacing one or more CCO inhibitors (such as, e.g., the vasodilator NO) that occupy one or more CCO oxygen binding sites. The localized release of NO from mitochondria can, therefore, be exploited to improve local blood flow thereby increasing O2 and nutrient levels in a damaged and/or a diseased tissue. The targeted delivery of light having a wavelength of from about 640 nm to about 700 nm may also be employed to preferentially increase the O2 binding affinity at a CCO active site thereby stimulating electron transport and aerobic generation of ATP.

As a further example, the present disclosure also provides the delivery of near infrared ("NIR") light (i.e., light having a wavelength of from about 800 nm to about 900 nm), which NIR light exhibits therapeutic benefit by facilitating the photo-mediated transfer of electrons from cytochrome C to CCO thereby improving the efficiency of electron flow and restoring mitochondrial membrane potential (MMP).

Thus, the present disclosure provides devices, systems, and methods that employ light having two or more distinct wavelengths, or ranges of wavelengths, which systems and methods include the coordinated delivery, which includes both concurrent delivery and temporally coordinated delivery, of multiple wavelengths of light with predefined optical parameters, such as, e.g., duration of delivery, frequency of delivery, continuous delivery, pulsed delivery, and fluence level of delivery, to provide, thereby, an individualized and personalized treatment regimen, which is optimized to restore, promote, and/or enhance mitochondrial function and, as a consequence, facilitate the recovery of a damaged tissue and/or reverse or slow the progression of disease in a diseased tissue.

As described herein, various aspects of such multi-wavelength phototherapy devices, systems, and methods may be tailored to affect important intracellular mediators such as, e.g., ATP, GTP, Nitric Oxide (NO), and/or reactive oxidative species (ROS), each of which is used by a cell to transmit intracellular stimuli via one or more signal transduction pathways, which, in turn, regulate downstream cellular activities/functionalities.

The capacity of the devices, systems, and methods of the present disclosure to control such second messenger-mediated cellular pathways provides an opportunity to affect key regulatory mechanisms of cell activity. Protein kinases, for example, represent a major class of enzymes that lead to the phosphorylation of protein targets. ATP, which is the active substrate for protein kinases, transfers a high-energy phosphorous bond to target proteins. Protein activity can, therefore, be increased or decreased by the phosphorylation of a target protein at one or more sites. As a consequence, enzyme activities and/or cellular pathways can be controlled by the availability of ATP to and the level of ATP within a cell, such as can be achieved by the inhibition or activation of one or more protein targets by one or more protein kinases.

As part of the present disclosure, it was discovered that the use of multiple wavelengths of light provides unique opportunities for treating damaged and/or diseased tissue by regulating signal transduction, mediating protein kinase activity, improving cellular performance, and restoring cellular function.

The multi-wavelength phototherapy devices, systems, and methods disclosed herein can be readily adapted for regulating and controlling cellular gene expression and restoring cellular function in a damaged and/or diseased tissue. Gene expression patterns are used by cells to coordinate and regulate numerous pathways that influence subsequent cellular activity. Multi-wavelength phototherapy systems and methods can, for example, be adapted for use in changing a gene expression pattern for multiple genes involved in cellular metabolism. Up regulation of several genes involved in electron chain transport, energy metabolism, and oxidative phosphorylation can be exploited to rejuvenate a cell's metabolic capacity and/or to stimulate ATP production, which can drive other pleiotropic processes and, collectively, can facilitate long-term improvement in and/or normalization of one or more cellular functions. In a related aspect, the multi-wavelength phototherapy systems and methods disclosed herein can also be adapted to affect NFU, a major cellular regulator of inflammatory pathways and gene expression.

Based upon these and other discoveries, which are described in detail herein, the present disclosure provides:

1. Multi-wavelength phototherapy devices, systems and methods for stimulating cytochrome c oxidase (CCO) activity in a cell and/or tissue, which methods include the coordinated delivery of two or more doses of light to a cell having two or more light sensitive factors that are associated with CCO activity, wherein each light dose has a distinct wavelength or range of wavelengths, wherein a first wavelength of light can stimulate a first light sensitive factor and a second wavelength of light can stimulate a second light sensitive factor thereby improving and/or restoring the one or more functionality of the target cell, in particular a target cell within a target tissue;

2. Multi-wavelength phototherapy devices, systems and methods for improving and/or restoring one or more functionality of a target cell, which systems and methods include the coordinated and targeted delivery to a cell and/or tissue of two or more distinct wavelengths of light to stimulate the activity of two or more light sensitive molecules thereby improving and/or restoring the one or more functionality of the target cell, in particular a target cell within a target tissue;

3. Multi-wavelength phototherapy devices, systems and methods for the treatment of a patient afflicted with a disorder and/or a disease that is associated with one or more absent and/or diminished cellular functionality, the systems and methods including the coordinated and targeted delivery of two or more distinct wavelengths of light to one or more cells in the patient thereby restoring the absent cellular functionality and/or enhancing the diminished cellular functionality thereby treating the disorder and/or disease; and 4. Multi-wavelength phototherapy devices, systems and methods for the treatment of a patient afflicted with an ocular disorder and/or a disease that is associated with one or more absent and/or diminished functionality in an ocular cell, the systems and methods including the coordinated and targeted delivery of two or more distinct wavelengths of light to an eye in the patient to restore and or enhance the absent and/or diminished functionality to the ocular cell thereby treating the ocular disorder and/or disease.

These and other aspects of the present disclosure can be better understood by reference to the following non-limiting definitions.

Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter. As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It will be understood that, unless indicated to the contrary, terms intended to be "open" (e.g., the term "including" should be interpreted as "including but not limited to," the term "having" should be interpreted as "having at least," the term "includes" should be interpreted as "includes but is not limited to," etc.). Phrases such as "at least one," and "one or more," and terms such as "a" or "an" include both the singular and the plural. Following long-standing patent law convention, the terms "a", "an", and "the" refer to "one or more" when used in this application, including the claims. Thus, for example, reference to "a cell" includes a plurality of such cells, and so forth.

Conditional language, for example, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

It will be further understood that where features or aspects of the disclosure are described in terms of Markush groups, the disclosure is also intended to be described in terms of any individual member or subgroup of members of the Markush group.

All references cited herein, whether supra or infra, including, but not limited to, patents, patent applications, and patent publications, whether U.S., PCT, or non-U.S. foreign, and all technical and/or scientific publications are hereby incorporated by reference in their entirety.

As used herein, the term "phototherapy," refers to the therapeutic delivery of light energy to a subject (e.g., a human or other mammal) to achieve one or more therapeutic benefits. The term "phototherapy," encompasses the term "Low level light therapy" or "LLLT," which refers to the therapeutic delivery of light energy at an irradiance level that is at or above an irradiance level that can promote one or more desired biostimulatory effects and is below an irradiance level that can cut, cauterize, and/or ablate a biological tissue. See, e.g., U.S. Pat. Nos. 6,537,304 and 6,918,922, each of which is incorporated by reference herein in its entirety.

As used herein, the term "light source" refers to an element of the light therapy apparatus (a/k/a phototherapy apparatus) that is configured to provide an optical output (e.g., to transmit light from a light therapy apparatus to a target tissue, such as an ocular tissue, of a patient). As used herein, the term "red light" refers to light having a wavelength of from about 640 nm to about 700 nm and the term "near infrared light" or "NIR" refers to light having a wavelength of from about 800 nm to about 900 nm.

As used herein, the terms "cytochrome c oxidase," "CCO," "Complex IV," and "EC 1.9.3.1" refer to a large transmembrane protein complex that is produced in the mitochondria and located within the mitochondrial membrane of eukaryotic cells. CCO is the last enzyme in the mitochondrial respiratory electron transport chain of mitochondria—receiving an electron from each of four cytochrome c molecules, transferring them to an oxygen molecule, and converting molecular oxygen to two molecules of water. CCO binds four protons from the inner aqueous phase to make water and translocates four protons across the membrane, thereby establishing a transmembrane proton electrochemical potential, which is used by ATP synthase for the synthesis of ATP.

As used herein, the terms "treatment," "treating," "therapeutic regimen," and "treatment regimen" refer, generally, to a therapeutic systems and methods that promote the healing of a damaged tissue and/or reverse or slow the progression of disease in a diseased tissue, which can be achieved by restoring one or more functionality in a cell within the damaged and/or diseased tissue. The terms "treatment," "treating," "therapeutic regimen," and "treatment regimen" include protocols and associated procedures that are used to provide a therapeutic system or method that includes one or more periods during which light is irradiated to one or more targeted cells and tissues, including ocular cells and tissues.

As used herein, the terms "target," "target area," and "target region" refer to a particular ocular area, region, location, structure, population, or projection within a tissue, such as a retina or an optic nerve, to which light is delivered in association with the treatment of a particular condition, disease, disorder, or injury, such as a condition, disease, disorder, or injury of an eye. In certain embodiments, the irradiated portion of a tissue, such as an eye can include the entire tissue. In other embodiments, the irradiated portion of the tissue can include a targeted region of the tissue, such as the retinal region, the macula, or the cornea of an eye.

As used herein, the term "degeneration" refers, generally, to a process of cell destruction resulting from primary destructive events such as trauma or surgery, as well as from secondary, delayed and progressive destructive mechanisms that are invoked by cells due to the occurrence of the primary destructive or disease event.

As used herein, the term "primary destructive events" refers to disease processes or physical injury or insult, including surgery, but also include other diseases and conditions, which, in the case of ocular disorders and diseases, can include glaucoma, age-related macular degeneration, diabetic retinopathy, retinitis pigmentosa, CRS, NAION, Leber's disease, ocular surgery, uveitis, cerebral ischemia including focal optic nerve ischemia, and physical trauma such as crush or compression injury to ocular tissues, including a crush or compression injury of the optic nerves or retina, or any acute injury or insult producing ocular degeneration.

As used herein, the term "secondary destructive mechanisms" refers to any mechanism that leads to the generation and release of neurotoxic molecules, including but not limited to, apoptosis, depletion of cellular energy stores because of changes in mitochondrial membrane permeability, release or failure in the reuptake of excessive glutamate, free radical damage, reperfusion injury, deposition of insoluble proteins including lipofuscin and β-amyloid and activity of complement, cytokines, and inflammatory conditions.

As used herein, the term "cytoprotection" refers to a therapeutic strategy for slowing or preventing the otherwise irreversible loss of a target tissue, such as an ocular tissue, due to degeneration after a primary destructive event, whether the tissue degeneration loss is due to disease mechanisms associated with the primary destructive event or secondary destructive mechanisms.

Both primary and secondary mechanisms contribute to forming a "zone of danger" wherein a tissue within the zone of danger that has survived a primary destructive event remains at a risk of dying due to one or more processes having a delayed effect.

As used herein, the term "restoration" refers to an increase in a functionality of a cell, such as a cell from a damaged and/or diseased tissue, to a level that is comparable to, equal to, or higher than the functionality of a comparable normal cell, such as a cell from a comparable undamaged and disease-free tissue, such as a tissue from a healthy individual.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p-value". Those p-values that fall below a user-defined cutoff point are regarded as significant. A p-value in some embodiments less than or equal to 0.05, in some embodiments less than 0.01, in some embodiments less than 0.005, and in some embodiments less than 0.001, are regarded as significant.

As used herein, the term "diagnosed" refers to a determination that has been made regarding a damaged and/or diseases tissue. A diagnosis may be made prior to using or performing the present multi-wavelength phototherapy systems and methods.

Light Delivery Devices

Within certain aspects, the present disclosure provides ophthalmic multi-wavelength phototherapy devices, including self-standing and wearable ophthalmic multi-wavelength phototherapy devices, and associated treatment methods. A device and method for exposing an eye to selected wavelengths of light that can promote the healing of damaged or diseased eye tissue. For example, a self-standing for use in an office or a wearable apparatus or device for use at home or elsewhere can deliver a therapeutic, independently controlled, multi-wavelength combination of low level light to ophthalmologic tissue. Treatment may include, for example targeting of damaged or diseased tissue with an ophthalmologic device capable of delivering multi-wavelength phototherapy therapeutics alone. Device and sensors or other imaging modalities may be used to establish the optimal ocular spatial and tissue parameters to provide an efficacious treatment to the eye. In at least some embodiments, the multi-wavelength device is used in combination with other pharmaceuticals or devices to enhance or personalize phototherapy treatment to ocular tissues.

The coordinated, independent use of selected wavelengths and the application of selected combinations of multi-wavelength PBM can create highly targeted, beneficial cellular responses. In at least some embodiments, a therapeutic approach to treat ocular disease or disorders can use the combination of two or more wavelengths alone or the use of one or more wavelengths in combination with a medical device, biologic or pharmaceutical to provide a desired therapeutic utility.

The use of individual wavelengths, such as red light (640-700 nm) or near infrared (NIR) light (800-900 nm), can each individually stimulate mitochondrial cytochrome C oxidase (CCO) enzyme activity as found in both in vitro and in vivo studies. It is found, however, that the individual wavelengths target distinct copper sites (e.g., CuA and CuB) within the multi-subunits of CCO and produce distinct biological responses. Thus, the coordinated use of both wavelengths in combination to target CuA and CuB) and to sequentially enhance both electron transfer and oxygen binding on the CCO enzyme can, at least in some embodiments, improve overall therapeutic CCO efficacy. The efficiency of CCO activity, restoration of mitochondrial membrane potential (MMP) and improvements in adenosine triphosphate (ATP) synthesis may all be intimately linked. This multi-wavelength approach may be used, at least in some embodiments, to restore MMP or to increase ATP formation (e.g. in a disease or disorder wherein the absence of or limited availability of oxygen is seen).

In one example, when blood flow is restricted, the use of one wavelength (in the range of 640-700 nm on CuB) may initially displace inhibitors, such as Nitric Oxide (NO), from the oxygen binding site. NO is a potent vasodilator and local NO release from mitochondria may improve local blood flow, increasing $O_2$ and nutrients into the diseased tissue area. In addition, stimulation with light having a wavelength in the range of 640-700 nm may preferentially increase $O_2$ binding affinity to the active site to stimulate electron transport and aerobic generated ATP. In other instances, where electron chain transfer of electrons from cytochrome C to CCO is dysfunctional and a more viable pathway for addressing ATP generation, may target CuA treatment with NIR at, for example, 810 nm (or in the range of 800 to 900 nm) may provide for photo-mediated, transfer of electrons from cytochrome C and improved efficiency of electron flow with restoration of MMP.

In some embodiments, the use of both wavelengths concurrently or in some sequence with predefined optical parameters (e.g., duration, frequency, continuous or pulsed, fluence level) can provide a treatment to restore mitochondrial function. Utilization of independently controlled, multi-wavelength light therapy may allow for enhancement or optimization of therapeutic effects and can be monitored or tailored to the disorder or disease state.

The use of multi-wavelength phototherapy may be tailored to effect important intracellular mediators. ATP, guanosine triphosphate (GTP), NO, reactive oxidative species (ROS) are all used by cells as the active substrates for signal transduction, which is the process known to transmit intracellular stimuli, which in turn regulates numerous cellular pathways and subsequent cellular activity. Control of cellular pathways by specific second messengers can provide a key regulator mechanism of cell activity. Protein kinases represent a major class of enzymes that lead to the phosphorylation of protein targets. ATP is the active substrate for protein kinases and used to transfer the high energy phosphorous bond to the target proteins. Protein activity can be increased or decreased by one or more phosphorylation sites. Therefore, enzyme or cellular pathway activity can be greatly controlled by the availability of ATP and ATP levels in the cell, either through inhibition or activation of specific protein targets by protein kinases.

The use of multiple wavelengths of light can, for example, regulate signal transduction, mediate protein kinase activity, improve cellular performance, or restore cellular function in damage or diseased tissue. The combined benefits of photons from one or more wavelengths can facilitate regulating second messengers affecting a specific pathway. For example, a light therapy could include the use of NO, ROS or ATP monitoring in the role of combination phototherapy to establish characteristics suitable for photobiomodulation applications.

Separately, the use of multiple wavelengths of light can be utilized to regulate and control cellular gene expression and restore cellular function in damage or diseased tissue. Gene expression patterns are used by cells to coordinate and regulate numerous pathways that influence subsequent cellular activity. Phototherapy (670 nm) is implicated in changing the gene expression pattern for multiple genes involved in cellular metabolism. Up regulation of several genes involved in electron chain transport, energy metabolism and oxidative phosphorylation is seen, thus rejuvenating the cells metabolic capacity and stimulating the increase in ATP production, which drives other pleiotropic processes, all leading to long-term improvement or normalization of cellular functions. Phototherapy may affect NFU, a major cellular regulator of inflammatory pathways and gene expression. The combined benefits of photons from one or more wavelengths can target and regulate gene expression of specific pathways. Gene expression mapping in multi-wavelength phototherapy can be used to identify characteristics suitable for photobiomodulation applications.

In at least some embodiments, the use of phototherapy in combination with gene therapy can stimulate, enhance or control the regulation and expression of novel genes incorporated into the nucleus through viral vectors or other gene therapy techniques. This is distinct from using light-activated gene products and utilizes selected wavelengths to naturally stimulate cellular gene expression profiles for newly implanted gene therapy. In at least some embodiments, the use of gene therapy can facilitate the regeneration of retinal tissue or to provide for gene therapy in the mitochondrial genetic ocular disorders, such as Leber's hereditary optic neuropathy or AMD. In those cases, gene therapy in combination with photobiomodulation to stimulate specific mitochondrial electron transport protein expression may provide a better or optimized therapeutic combination approach.

Separately, RNA and protein expression patterns are used by cells to effectively regulate numerous pathways and subsequent cellular activity. Multiple wavelengths of light can be used to indirectly regulate and improve RNA and protein expression and restore cellular function in damage or diseased tissue. Protein mapping can be used in combination with phototherapy to identify characteristics suitable for photobiomodulation applications. AMD is considered a chronic inflammatory disease where protein deposits further propagate the inflammatory state and disease progression. Therefore, the use of multi-wavelength PBM can deliver a combination therapeutic. In RPE cell studies, the use of 590 nm light has been shown to inhibit VEGF expression and thus the use of 590 nm PBM (or another wavelength in the range of 500 to 650 nm) can be useful in the treatment of wet AMD subtype to suppress VEGF protein expression locally in ocular tissue.

VEGF antibody treatment (Lucentis®) is a currently approved pharmaceutical treatment for wet AMD. Separately, the use of 810 nm PBM (or another wavelength in the range of 800 to 900 nm) can improve mitochondrial function, reduce inflammatory markers, or prevent β-amyloid deposits in age-related Alzheimer's mice (or any combination of these effects). Further, the use of 670 nm PBM (or another wavelength in the range of 600 to 750 nm) can reduce inflammatory markers like complement C3 expression and deposition in AMD mouse models but does not affect b-amyloid deposition. Both deposition of lipofusion and β-amyloid have been implicated in the etiology of the diseased eyes in AMD patients. The combinations of multi-wavelength PBM can be used alone or used with one or more drugs, such as, for example, one or more of an anti-VEGF monoclonal antibodies (MAbs) (e.g. Lucentis® and Avastin®); an anti-inflammatory drug (e.g. non-steroidal, anti-inflammatory agents, anti-complement agent (e.g. Properidin, C3, MASP-2, C5 inhibitors); antioxidants or vitamin supplements (e.g., AREDS supplements (Lipotriad Visonary™, Viteyes 2®, ICaps®, and PreserVision®), contain similar constituents but either in different proportions, or with additional ingredients,) or visual cycle disruptor (e.g. isomerase inhibitors (ACU-4429).

In at least some embodiments, the targeted use of phototherapy to improve mitochondrial function via increased CCO activity, restoration of MMP and regulation of ATP synthesis may be achieved by the use of multiple wavelengths of light to create the appropriate local cellular response to damage or disease. Localized cellular conditions in trauma and disease may differ across discrete tissue or organ areas and are under dynamic local regulation. For example, phototherapy of local CCO activity can lead to release of inhibitory NO from the $O_2$ binding site. NO is a powerful vasodilator and signal transducer which can regulate the local blood flow to targeted tissue. This may be useful in reversing local ischemia or restricted blood flow to damaged or diseased tissue.

In at least some embodiments, a treatment can include the discrete targeting of phototherapy to tissues such as within the retina and associated surrounding ocular tissue types. As an example, it may be most beneficial to treat discrete local optic nerve ischemia as seen in non-arteric ischemic optic neuropathy (NAION). In another example, it may be most beneficial to target anatomical islands of cellular deposits that may be a nidus for inflammation, ischemia or disease in dry AMD. In early stage AMD, discrete cellular deposits of lipofusion or drusen can be identified on the retina by standard imaging techniques (OCT, fluorescence imaging). In such an example, the use of imaging modalities such as OCT or fluorescence may be used to target the multi-wavelength phototherapy to slow the disease, stop or reverse the deposition of proteins such as lipofusion or β-amyloid and reduce, slow or stop the progression of the disease.

These targeted phototherapy applications provide a disease-modifying approach to chronic ocular disease. An instrument can produce phototherapy alone or in combination with OCT or some other imaging devices (e.g., PET, MRI, Ultra-sound, Doppler, Fluorescence, Femtosensors, etc.) as an approach to identify discrete areas of interest and target cell or tissue boundaries with a combination of wavelengths to enhance, optimize, or personalize patient treatment.

In another such example, imaging modalities, such as femtosensors to monitor local retinal $O_2$ levels, may be used to identify AMD patients with local hypoxia and to combine with phototherapy to improve treatments and to monitor increased $O_2$ levels to restore mitochondrial retinal function.

In at least some embodiments, the selection of wavelength and doses and treatment parameters may vary depending on the underlying disease or disorder. The independent targeting of multiple wavelengths of light can facilitate one or more of local phototherapy, individualized patient phototherapy, restored cellular performance, or to slow or stop ocular disease propagation. These approaches can be performed alone, in combination with existing diagnostic devices or as instruments combining phototherapy and diagnostic modalities.

In at least some embodiments, photobiomodulation includes the selection of wavelengths and dosing parameters. Distinct wavelengths have individual tissue absorption properties, which impact the depth of penetration and the appropriate dose for clinical efficacy. A device can include a component, such as a camera or other sensor, that can use used to capture patient orbital features, including depth, size, skin color, or distances. This allows for setting of the dose for each wavelength separately or in combination at preset values to enhance or optimize treatment parameters. In at least some embodiments, the sensor may be used to aid in the dose selection through the open or closed eyelid, taking into account, for example, tissue color or thickness.

In at least some instances, there is some amount of intervening tissue between the light source and the target tissue. In at least some embodiments, a wavelength of light can be selected at which the absorption by intervening tissue is below a damaging level. Such embodiments may also include setting the power output of the light source at low, yet efficacious, irradiances (for example, between approximately 100 $\mu W/cm^2$ to approximately 10 $W/cm^2$) at the target tissue site, or setting the temporal profile of the light applied to the tissue (e.g., temporal pulse widths, temporal pulse shapes, duty cycles, pulse frequencies) or time periods of application of the light energy at hundreds of microseconds to minutes to achieve an efficacious energy density at the target tissue site being treated. Other parameters can also be varied in the use of phototherapy. These other parameters contribute to the light energy that is actually delivered to the treated tissue and may affect the efficacy of phototherapy.

In at least some embodiments, the target area of the subject's tissue includes the area of injury, for example, to the optic nerve and surrounding ocular tissue. In some embodiments, the target area includes portions of the eye.

In at least some embodiments, the devices and methods of phototherapy described herein are used to treat ocular disorders. As used herein, ocular disorder can refer to at least one characteristic or experiencing symptoms of ocular syndromes (e.g., glaucoma, age-related macular degeneration, diabetic retinopathy, retinitis pigmentosa, CRS, NAION, Leber's disease, ocular surgery, uveitis, or the like, and not limited to and including further indications as described throughout this application).

In at least some embodiments, the devices and methods of phototherapy described herein are used to treat physical trauma (e.g., cataract or lens surgery) or other sources of ocular inflammation or degeneration or aid in rehabilitation of the ocular degenerative effects caused by the physical trauma. Ocular degeneration can include, for example, the process of cell destruction resulting from primary destructive events such as ocular trauma or surgery, as well as from secondary, delayed and progressive destructive mechanisms that are invoked by cells due to the occurrence of the primary destructive or disease event.

Primary destructive events can include disease processes or physical injury or insult, including surgery, but also include other diseases and conditions such as glaucoma, age-related macular degeneration, diabetic retinopathy, retinitis pigmentosa, CRS, NAION, Leber's disease, ocular surgery, uveitis, cerebral ischemia including focal optic nerve ischemia, and physical trauma such as crush or compression injury to ocular tissues, including a crush or compression injury of the optic nerves or retina, or any acute injury or insult producing ocular degeneration.

Secondary destructive mechanisms can include any mechanism that leads to the generation and release of neurotoxic molecules, including but not limited to, apoptosis, depletion of cellular energy stores because of changes in mitochondrial membrane permeability, release or failure in the reuptake of excessive glutamate, free radical damage, reperfusion injury, deposition of insoluble proteins including lipofusin and β-amyloid and activity of complement, cytokines and inflammatory conditions. Both primary and secondary mechanisms contribute to forming a "zone of danger" for ocular tissue, where the tissue in the zone have at least temporarily survived the primary destructive event, but are at risk of dying due to processes having delayed effect.

In at least some embodiments, the devices and methods described herein are used to provide cytoprotection. Cytoprotection can include a therapeutic strategy for slowing or preventing the otherwise irreversible loss of ocular tissue due to degeneration after a primary destructive event, whether the tissue degeneration loss is due to disease mechanisms associated with the primary destructive event or secondary destructive mechanisms.

In at least some embodiments, the devices and methods described herein are used to improve ocular function, to provide ocular enhancement, to prevent or slow the progression of loss of ocular function, or to regain previously lost ocular function, or any combination thereof. Ocular function can include both visual acuity function and contrast sensitivity function.

Diseases or conditions affecting ocular function include, but are not limited to, primary destructive events, disease processes or physical injury or insult, including age-related macular degeneration and other diseases and conditions such as glaucoma, stroke, diabetic retinopathy, retinitis pigmentosa, CRS, NAION, Leber's disease, ocular surgery, uveitis, cerebral ischemia including focal optic nerve ischemia, and physical trauma such as crush or compression injury to ocular tissues, including a crush or compression injury of the optic nerves or retina, or any acute injury or insult producing ocular degeneration.

As used herein, the terms "therapeutic regimen" and "treatment regimen" refer to a protocol and associated procedures used to provide a therapeutic treatment that includes one or more periods during which light is irradiated to one or more ocular target regions. As used herein, the terms "target," "target area," and "target region" refer to a particular ocular area, region, location, structure, population, or projection (e.g., within the retina or optic nerve) to be irradiated by light in association with the treatment of a particular type of ocular condition, disease, disorder, or injury. In at least some embodiments, the irradiated portion of the eye can be the entire eye. In other embodiments, the irradiated portion of the eye is a targeted region of the eye, such as the retinal region, the macula, or the cornea.

In at least some embodiments, the methods and devices described herein can be used to promote the proliferation, migration and regenerative cellular properties of endogenous progenitor retinal stem cells for use in retinal or ocular diseases. Stem cells have the capacity to both self-renew and generate post-mitotic cells. The retinal pigment epithelium (RPE) is a monolayer of cells underlying and supporting the neural retina. It begins as a plastic tissue, capable, in some species, of generating lens and retina, but differentiates early in development and remains normally non-proliferative throughout life. However, subpopulations of adult human RPE cells can be activated in vitro to a self-renewing cell, the retinal pigment epithelial stem cell (RPESC) that loses RPE markers, proliferates extensively, and can redifferentiate into stable cobblestone RPE monolayers. Clonal studies demonstrate that RPESCs are multipotent and in defined conditions can generate both neural and mesenchymal progeny. This plasticity may explain human pathologies in which mesenchymal fates are seen in the eye, for example in proliferative vitroretinopathy (PVR) and phthisis bulbi. The RPESC as an accessible, human CNS-derived multipotent stem cell, useful for the study of fate choice, replacement therapy, and disease modeling.

In at least some embodiments, the methods and devices described herein can be used to promote the proliferation, migration and regenerative cellular properties following implantation of stem cells used in retinal or ocular diseases. Stem cell-based therapy is being pursued for treatment of retinal degenerative disease. Retinal stem cells have been isolated from several mammalian species, including humans. However, transplantation of these cells has been minimally successful due to the limited ability of the cells to migrate and integrate into the host retina. Bone marrow-derived stem cells may be an alternative, but bone marrow contains several types of pluripotent/multipotent cells, including hematopoietic stem cells, mesenchymal stem cells, and a heterogeneous population of non-hematopoietic cells that differentiate into mesenchymal tissues but possibly into other tissue types.

In at least some embodiments, the methods and devices described herein can be used in combination with compositions and methods applicable to cell-based or regenerative therapy for retinal diseases and disorders. In at least some embodiments, the methods and devices described herein can be used with pharmaceutical compositions, devices and methods for the regeneration or repair of retinal tissue using stem cells (e.g., Very Small Embryonic-like Stem cells (VSELs), mesenchymal stem cells, ectodermal stem cells, etc.).

For example, the methods and devices described herein can be used in a method for treating a retinal disorder with PBM after administering to an individual in need thereof an ectodermal stem cell population to the individual's retinal tissue, and intravenously administering to the individual a mesenchymal stem cell population. The ectodermal stem cells may be derived from fetal neural tissue. In at least some embodiments, the methods and devices described herein can be used in deriving the mesenchymal stem cell population from a source selected from at least one of umbilical cord blood, adult bone marrow and placenta. In at least some embodiments, the methods and devices described herein can be used to treat one or more disease or disorders including, but not limited to, macular degeneration, retinitis pigmentosa, diabetic retinopathy, glaucoma or limbal epithelial cell deficiency. In at least some embodiments, the cells are induced in vitro to differentiate into a neural or epithelial lineage cells prior to administration and preconditioned with PBM. In other embodiments, the cells are administered with at least one other agent, such as a drug for ocular therapy, or another beneficial adjunctive agent such as an anti-inflammatory agent, anti-apoptotic agents, antioxidants or growth factors. In these embodiments, PBM treatment can be administered simultaneously with, or before, or after, the postpartum cells. The use of PBM may be used stimulate the regenerative aspects of the stem cells or use to supplement beneficial adjunctive therapeutic agents or both.

Another embodiment is a cell lysate prepared from mesenchymal stem cells or ectodermal stem cells that have been treated with PBM. The cell lysate, may be separated into a membrane enriched fraction and a soluble cell fraction. The present disclosure features the treatment of PBM to the cells in vitro prior to cell lysate preparation and prior to administration as well as after implantation into the patient.

The PBM methods for the treatment of ocular conditions, as described herein and in U.S. Provisional Patent Application No. 62/048,211 may be practiced and described using various light delivery systems. U.S. Provisional Patent Application No. 62/048,211, which was filed on Sep. 9, 2014 and entitled MULTI-WAVELENGTH PHOTO-THERAPY SYSTEMS AND METHODS FOR THE TREATMENT OF DAMAGED OR DISEASED TISSUE, is incorporated herein by reference in its entirety.

In one embodiment, the device is in a configuration conducive to office-based usage. The device may be self-standing or can be attached to an existing apparatus. This device may be augmented to include other diagnostic or therapeutic capabilities related to ocular disorders or to form a system with other devices.

The devices described herein are in a wearable configuration. This device may be augmented to include other diagnostic or therapeutic capabilities related to ocular disorders or to form a system with other devices.

The light delivery apparatus or device can be a floor, desk, cart, or table based unit. The device contains one or more light engines containing one or more light sources to deliver light of one or more selected wavelengths. The light from the sources can be combined using, for example, beam shaping optics, optical filters, light pipes, or combinations of these to achieve the desired spatial and spectral irradiance pattern at the eye. Other optical components may be included to guide the light from the light engine to the eye. In at least some embodiments, the device output is substantially spatially fixed, such that proper exposure of the target region requires the position of the patient to be manipulated and optimized. Such patient manipulation may be aided with the use of an adjustable chin rest or forehead rest or both. Fine spatial adjustment of the output may be accomplished through the use of, for example, moving elements (e.g., fold mirrors, etc.) within the device, actuated either manually or electrically. In other embodiments, the output of the device is substantially spatially adjustable. In this case, the device may contain a forehead or chin rest or both as a patient interface, and the output of the device may be adjusted to expose the target region. Large spatial adjustments can be accomplished with, for example, one or multiple optical elements (e.g., lenses, fold mirrors, etc.) translating or rotating to redirect the light to the target region. The adjustability may cover the expected range of positions for a single eye, or it may cover the range of positions expected for both eyes, eliminating the need to readjust a patient if treating both eyes sequentially.

As the device is suited for an office environment, it should be expected that a multitude of patients will interface with the device, and measures may be taken to limit cross-contamination between individuals. In at least some embodiments, removable forehead or chin rests can be provided that are either cleanable or disposable. In at least some embodiments, the forehead or chin rests may be protected by a cleanable or disposable barrier.

In at least some embodiments, the device contains an interface with which the user (doctor, practitioner, or patient) can initiate controls. This may include a touch screen or keyboard to select various treatment modalities, enter or extract data, perform device diagnostics, etc. A tangible or virtual joystick or other mechanism may be included to spatially adjust the system output.

FIGS. 1A-1D illustrate one embodiment of a light therapy device 100. The device 100 includes a housing 102, a patient interface surface 104, and at least one eyebox or eyepiece 106. The device also optionally includes a user interface 108, a power switch 110, a locking mechanism 112, and a beam positioning mechanism 114. The housing 102 holds the light engine and other optics, as described in more detail below. The illustrated housing 102 is one example of a housing, but it will be understood that other housing configurations can be used including a housing that attaches to, or supports, other optical devices.

The patient interface surface 104 is arranged so that the patient is positioned correctly to irradiate the eye or eyes of the patient with light therapy. The patient interface surface may be arranged to roughly fit the contours of the face of a patient and may include a disposable or cleanable surface to prevent or reduce patient cross-contamination.

The eyebox or eyepiece 106 may accommodate both eyes of the patient or only a single eye. In some embodiments, there may be separate eyeboxes or eyepieces for the right and left eyes. The eyebox or eyepiece 106 may have a peripheral region that is intended to contact the area around a patient's eye or the patient interface surface 104 may be sufficient to position the patient correctly to receive light therapy. The eyebox or eyepiece 106 may be simply an opening into which the patient positions his eye or the eyebox or eyepiece may include a lens or other optical components.

The optional user interface 108 can be built into the device and can be any suitable interface including, but not limited to, a touchscreen interface, a keyboard and display, or the like. Alternatively or additionally, the device 100 can include or permit a wired or wireless connection to an external user interface such, as for example, an external computer, a keyboard, a mouse or joystick, or the like. The user interface 108 is typically operated by the doctor or other practitioner, but, in some embodiments, there may be portions of the user interface that can be operated by the patient such as, for example, a button or other element for halting or starting light therapy. The user interface 108 may be used to input therapy parameters, patient information, operate the device 100, or any other suitable use. In some embodiments, the user interface 108 may also be coupled to an internal camera (for example, camera 754 of FIG. 7) so that the practitioner can view the patient's eye to aid in diagnosis or directing light therapy.

The optional power switch 110 can have any suitable form. The optional locking mechanism 112 may be provided to allow a user to lock operation of the device 100. The optional beam positioning mechanism 114 can be used to move the beam to interact with the patient's eye or eyes and can be any suitable mechanism including, but not limited to, a joy stick, a track ball, or a touchscreen.

FIG. 2 illustrates another embodiment of a device 200 that includes a housing 102, a patient interface surface 104, at least one eyebox or eyepiece 106, an optional user interface 108, an optional power switch 110, an optional locking mechanism 112, an optional beam positioning mechanism 114, and a chin rest 116. The chin rest 116 can have any suitable form and may have a surface that is disposable or cleanable to receive the chin of the patient. Preferably, the height of the chin rest relative to the remainder of the device is adjustable.

FIGS. 3A and 3B illustrate yet another embodiment of a device 300 that includes a housing 102, a patient interface surface 104, at least one eyebox or eyepiece 106, an optional user interface 108, an optional power switch 110, an optional locking mechanism 112, and an optional beam positioning mechanism 114. In this embodiment, the patient interface surface 104, as illustrated in FIGS. 3A and 3B, is removable so that it can be cleaned or replaced.

Figure 4:
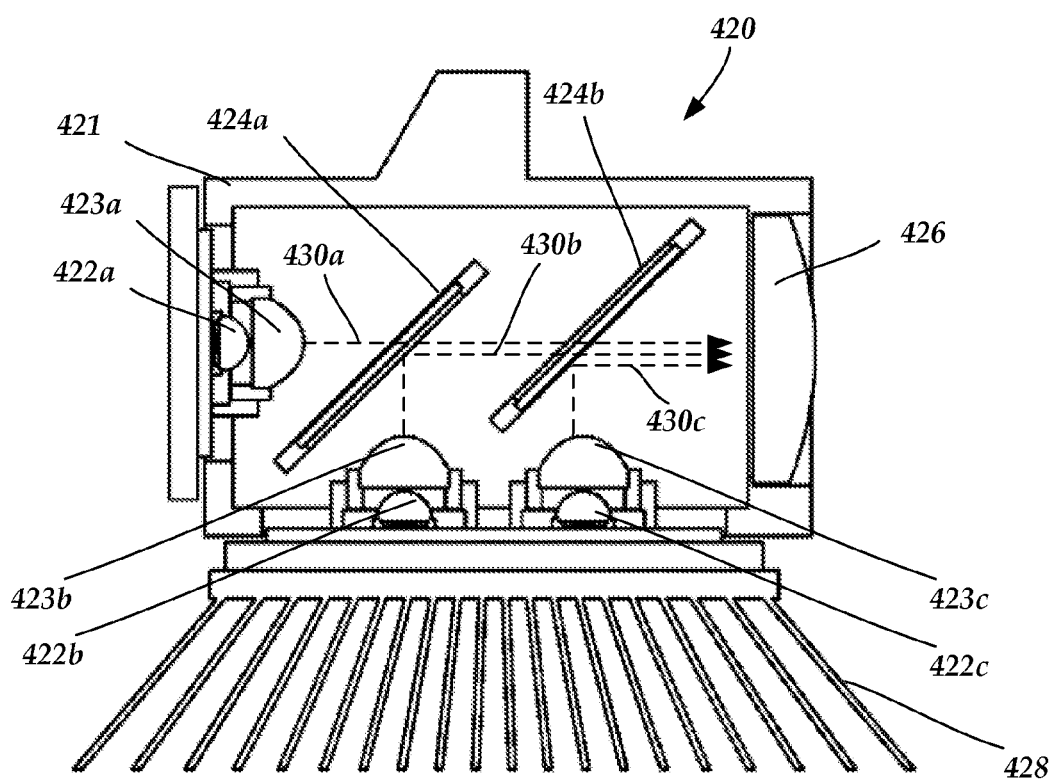
FIG. 4 is a schematic cross-sectional view of one embodiment of a light engine for use with a light therapy device, according to the present disclosure.

FIG. 4 illustrates one example of a light engine 420 for use with the device 100 (see, FIG. 1A) and positioned within the housing 102 (see, FIG. 1A) of device 100. The light engine 420 includes an engine housing 421, one or more light sources 422a, 422b, 422c, one or more light directing components 424a, 424b, an optional lens 426, and an optional heat exchanger or heat sink 428. Light emitted from the light sources 422a, 422b, 422c forms light beams 430a, 430b, 430c, respectively.

Any suitable light source can be used in this embodiment or any of the other embodiments described herein including, but not limited to, light emitting diodes (LEDs), laser diodes, lamps, lasers, and the like. In at least some embodiments, one or more light emitting diodes are used. In other embodiments, one or more laser diodes are used. The one or more laser diodes can be gallium-aluminum-arsenic (GaAlAs) laser diodes, Aluminum gallium indium phosphide (AlGaLnP) laser diodes, diode-pumped solid state (DPSS) lasers, or vertical cavity surface-emitting laser (VCSEL) diodes, for example.

In at least some embodiments where multiple light sources are used, the light sources can be coupled to one or more optical fibers. Other light sources that generate or emit light with an appropriate wavelength and irradiance can also be used. In some embodiments, a combination of multiple types of light sources can be used. Each light source can optionally include one or more of a lens (for example, lenses 423a, 423b, 423c), diffuser, waveguides, or other optical elements associated with the light source.

In some embodiments, the device may also include one or more non-light energy sources, such as magnetic energy sources, radio frequency sources, DC electric field sources, ultrasonic energy sources, microwave energy sources, mechanical energy sources, electromagnetic energy sources, and the like. For example, the phototherapy could be combined with OCT, PET, MM, femtosensors, or the like to provide instruments with therapeutic, diagnostic, tracking or enhanced targeting capabilities.

In at least some embodiments having two or more light sources, the individual light sources may be selected to generate light of different wavelengths. The wavelengths or ranges of wavelengths that are to be delivered to the eye are generated by the light sources, but can be filtered to remove some or all of the light of other wavelengths. In at least some embodiments, a first light source provides light of a first wavelength (which may be delivered with light of adjacent wavelengths or filtered to remove other light) and a second light source provides light of a second wavelength. In at least some embodiments, the first and second wavelengths differ by at least 25, 50, 75, 100, 150, 200, 250, 300, 400, or 500 nm. In some embodiments, a third light source provides light of a third wavelength and the third wavelength differs from the first and second wavelengths differ by at least 25, 50, 75, 100, 150, 200, 250, 300, 400, or 500 nm.

The light engine 420 includes one or more light directing components 424a, 424b. In the illustrated embodiment, light directing components 424a, 424b are reflective filters. Light directing component 424a is selected to pass light in light beam 430a having a first wavelength generated by first light source 422a and to reflect light in light beam 430b having a second wavelength generated by second light source 422b. Light directing component 424b is selected to pass light in light beam 430a having a first wavelength and light in light beam 430b having a second wavelength generated by second light source 422b. Light directing component 424b reflects light in light beam 430c having a third wavelength generated by second light source 422c. The light directing component 424b directs the desired wavelengths of light to lens 426.

Other light directing components can be used including, but not limited to, optical fibers, absorbing filters, reflective or absorbing polarizers, beamsplitters, and the like. In some embodiments, the device is operated so that two or more of the light sources generate light simultaneously. In other embodiments, the device operates to deliver light from a single light source at any given time, although the light sources may be turned on and off in any suitable light delivery sequence. The lens 426 can be a single lens or a combination of lenses and may include other optical components such as, for example, diffusers, apertures, filters, and the like.

Figure 5:
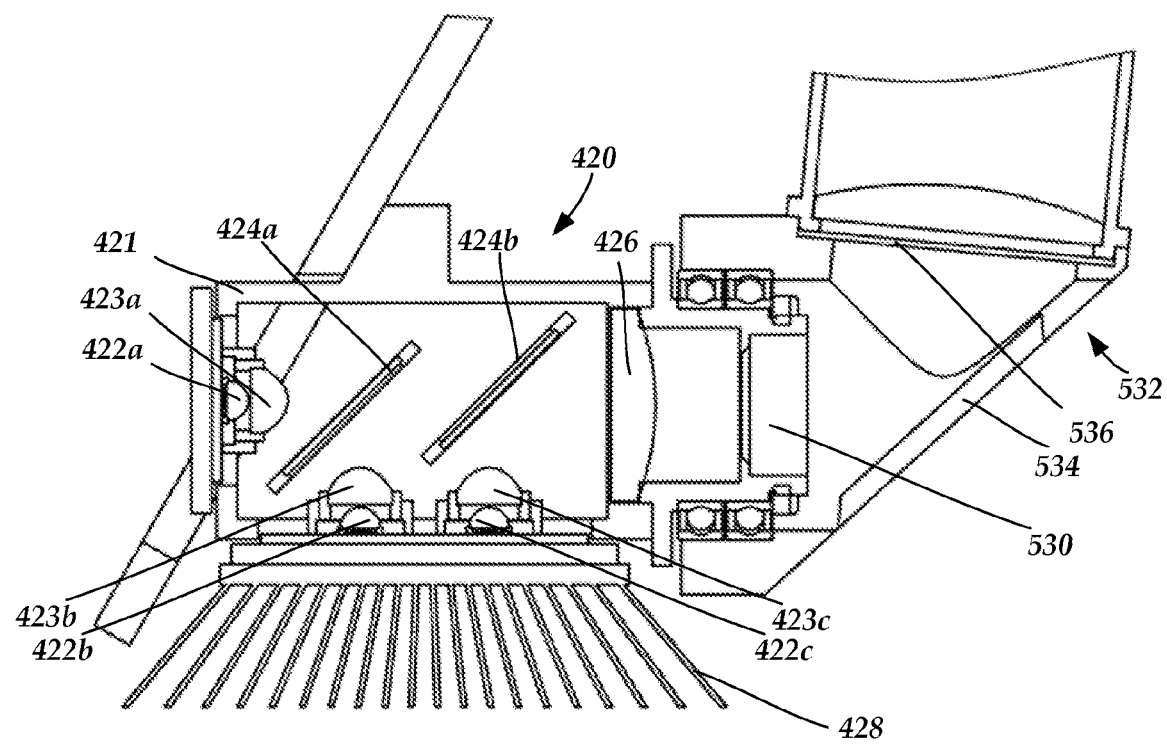
FIG. 5 is a schematic cross-sectional view of one embodiment of the light engine of FIG. 4 with additional optical components for use with a light therapy device, according to the present disclosure.

FIG. 5 illustrates the light engine 420 of FIG. 4 with additional optical components including an aperture 530 and a relay structure 532. The aperture 530 receives the light from the lens 426 and limits light directed to the eye of the patient. The relay structure 532 directs the light from the light engine 420 to the patient and can include any number of suitable components including, for example, one or more mirrors 534 and one or more lenses 536.

Figure 6A:
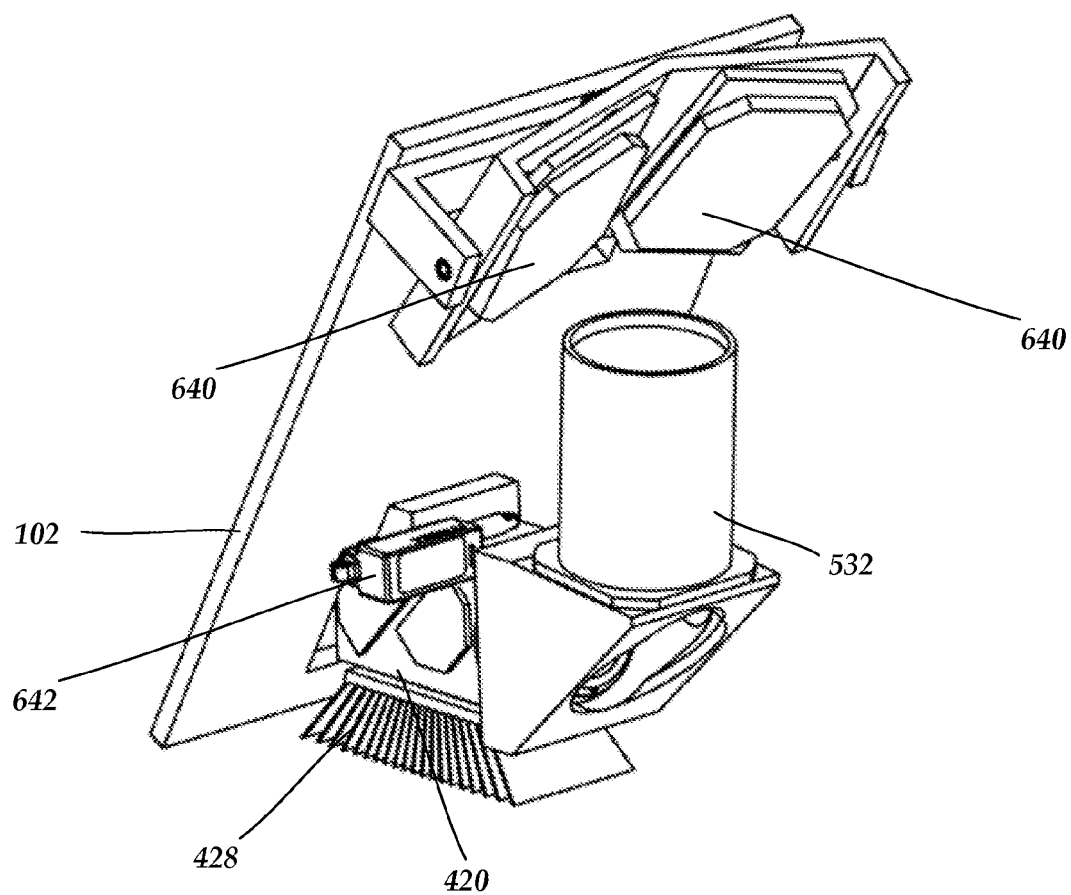
FIG. 6A is a side perspective view of one embodiment of optical components for use with a light therapy device, according to the present disclosure.
Figure 6B:
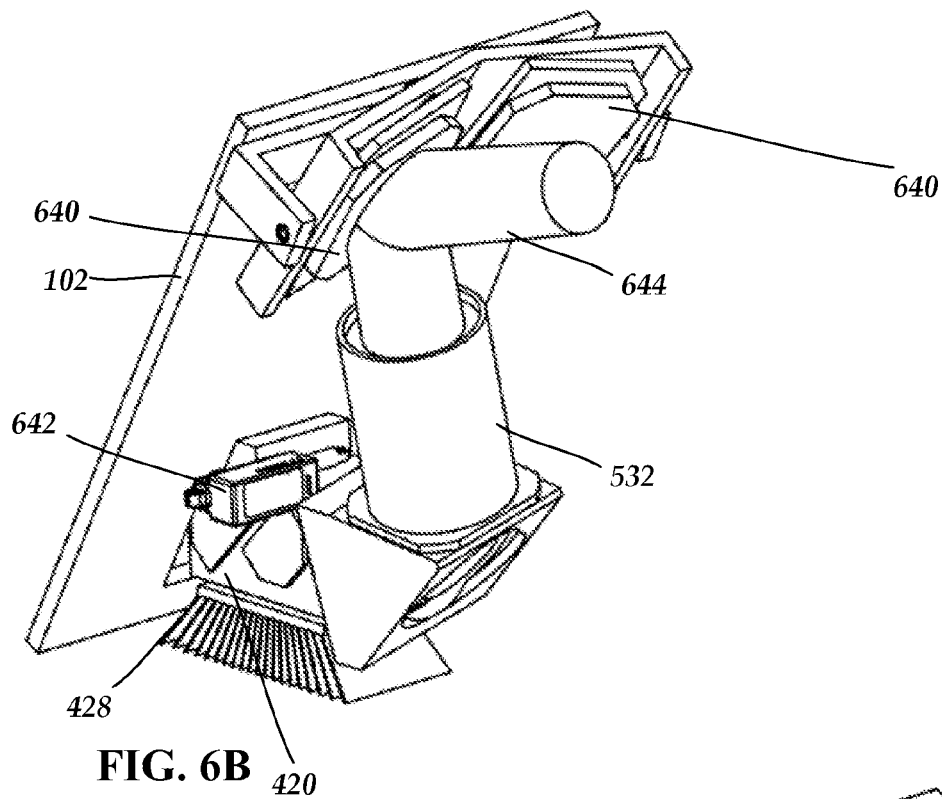
FIG. 6B is a side perspective view of the optical components of FIG. 6A with light directed to the left eye of a patient, according to the present disclosure.
Figure 6C:
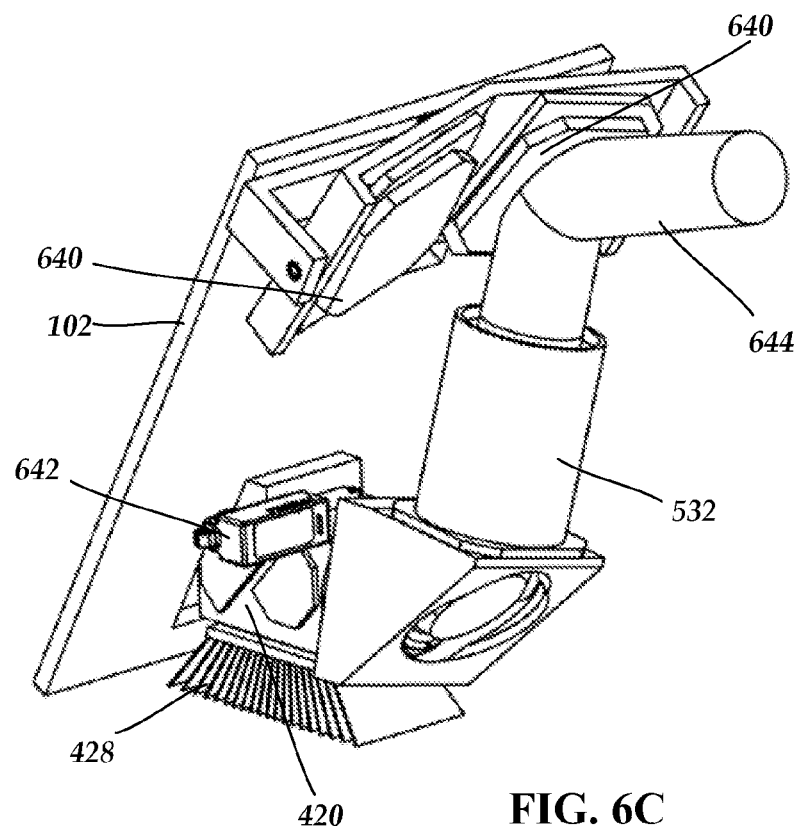
FIG. 6C is a side perspective view of the optical components of FIG. 6A with light directed to the right eye of a patient, according to the present disclosure.

FIGS. 6A-6C illustrate additional components of the device for delivery of light from the light engine 642 to the patient including a portion of the device housing 102, flow mirrors 640, and actuator 642. The actuator 642 can be used to rotate portions of the relay structure 532 (or even part of the light engine 420) to adjust the direction that the light beam 644 (FIGS. 6B and 6C) is directed. FIG. 6B illustrates a position with the light beam directed toward the left eye of the patient and FIG. 6C illustrates a position with the light beam directed toward the right eye of the patient. In some embodiments, the actuator 642 may simply have two positions. In other embodiments, the actuator 642 permits finer adjustment of the light beam position. In at least some embodiments, the actuator 642 is coupled to the user interface 108 or beam positioning mechanism 114 or both.

In at least some embodiments, the irradiance of the light beam is selected to provide a predetermined irradiance at the target ocular tissue. The target tissue may be an area of the eye affected by disease or trauma that has been identified using standard medical imaging techniques, it may be a portion of the eye that is known to be affected by a particular disease, it may be a portion of the eye that is known to control certain functions or process, or it may be any section of the eye. The selection of the appropriate irradiance of the light beam emitted from the emission surface to achieve a desired irradiance at the level of the target ocular tissue preferably includes, among other factors, the wavelength or wavelengths of light selected, the type of disease (if any), the clinical condition of the subject, and the distance to the target region.

In at least some embodiments with a plurality of light sources, certain light sources emit light at a higher or lower power as compared to other light sources. Power output of the light source can thus be tailored depending on the thickness of the eyelid, cornea, or other intervening tissue between the emission surface of the light source and the target ocular tissue. The parameters of the light emitted by the light sources are discussed in greater detail below.

Figure 8:
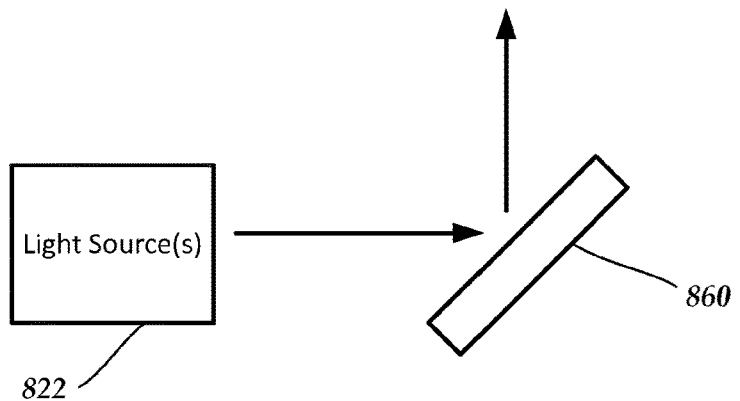
FIG. 8 is a schematic block diagram of the use of a spatial light modulator in the system for providing light therapy, according to the present disclosure.

In some embodiments, the device may also include a spatial light modulator to produce an image using the light from the light sources or to facilitate targeting of the light to a particular part of the eye (for example, the retina or a portion of the retina). FIG. 8 illustrates an arrangement with the light source(s) 822 with light directed to a spatial light modulator (SLM) 860 that modulates the light and directs the modulated light beam to the patient. The spatial light modulator 860 can be, for example, a liquid crystal on silicon (LCOS) display, a liquid crystal display (LCD), a micromirror array such as a digital light processor (DLP), a scan mirror, or any other suitable device that can reflect light and optionally can be used to form an image. The spatial light modulator may also include additional projection optics such as, lenses and the like. In at least some embodiments, the device may also utilize the lens of the patient's eye to also facilitate image formation.

The spatial light modulator may be reflective, as illustrated in FIG. 8, or transmissive in which the light is modulated as it is transmitted through the SLM. The spatial light modulator can be inserted at any suitable place along the light path. For example, a reflective SLM could be placed at the position of the fold mirror 534 in the embodiment illustrated in FIG. 5 or in any other suitable portion of the device. A transmissive SLM could be placed before or after the lens 426 or aperture 530 in the embodiment illustrated in FIG. 5 or in any other suitable portion of the device.

In at least some embodiments, targeting of the light source on a particular portion of the eye of the patient can be performed using the spatial light modulator, a camera to observe the patient's eye to allow manual or automatic adjust of the direction of the light beam, pupil tracking sensor, or any combination thereof.

Figure 7:
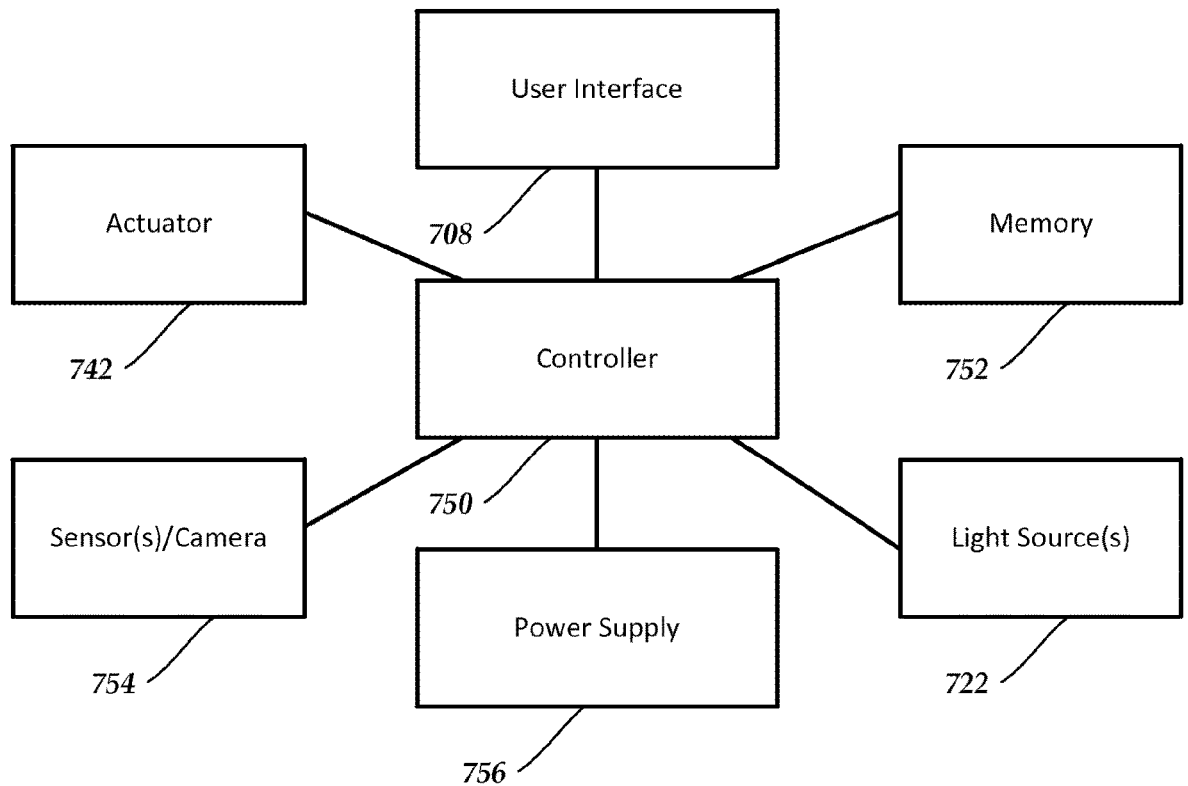
FIG. 7 is a schematic block diagram of components of one embodiment of a system for providing light therapy, according to the present disclosure.

FIG. 7 illustrates one embodiment of a system for operating the devices for treatment of ocular disease, disorders, degeneration, and the like. The system includes a controller 750, the user interface 708 (for example, user interface 108 of FIGS. 1A-3A), the actuator 742 (for example, actuator 642 of FIGS. 6A-6C), the light source(s) 722 (for example, light sources 422a, 422b, 422c of FIGS. 4 and 5), memory 752, one or more sensor(s)/camera 754, and a power supply 756. These components are described in more detail below. It will be recognized that other systems can include more or fewer components and that the components may be linked together in arrangements different from those illustrated in FIG. 7. For example, the spatial light modulator 860 of FIG. 8 can also be linked to the controller 750 of FIG. 7. In addition, any linkage between components can be through wired or wireless communication or any combination thereof.

Within certain embodiments of the present disclosure, light delivery devices are wearable to, thereby, facilitate portability and allow for the option of usage outside of a traditional ophthomology office such as, for example, usage at home, while at work, or during recreational activities and travel. Thus, the presently described wearable devices provide such advantages as reducing travel burden on a patient and providing convenience to the patient in selecting time for delivery of the therapy.

Wearable devices may be monocular, in that it is intended to expose only one eye to the light therapy, or it may be binocular, where the device may treat both eyes concurrently, sequentially, or in a specified sequence. Binocular devices are described herein in detail and the design considerations, parameters, and structures discloses herein can also be implemented in monocular devices.

Wearable devices may contain one or more light sources of one or more wavelengths. In at least some embodiments, the device contains of an array of light sources directed towards the eyes and spaced at specific intervals to produce the desired spatial and spectral irradiance on the eye. In at least some embodiments, optical components can be used to redirect the light from the light sources toward the wearer's eye. Intermediate optical elements (e.g., lenses, filters, diffusers) can further shape the output of the device as required.

In at least some embodiments, the light source is positioned out of the line of sight of the eyes, and the light is directed to the eyes via light-pipes or waveguides or any other suitable components. The waveguides may function to mix multiple wavelengths or to homogenize the device output. The waveguides may incorporate integral lenses, coatings, or diffusers to shape the beam at the entrance and exit of the waveguide. In at least some embodiments, the waveguide is transparent, such that the user has largely unimpeded vision while wearing the device. Planar optical elements such as volume-phase holograms, surface-relief holograms, diffraction gratings, or similar elements may be placed upon, or incorporated into, the waveguide to direct the light and shape the output, while keeping the waveguide largely transparent.

In at least some embodiments, the light source is positioned out of the line of sight of the eyes, and the light is directed to the eyes via reflection from a surface. A coating may be placed on the surface to facilitate reflection. The surface may be flat, or it may be curved in one or more directions, in which case the curves may be prescribed to shape the light output of the device. The surface may be largely reflective at the incident angle of the light, and may be largely transmissive at normal incidence, such that the wearer's vision is largely unimpeded. A coating may be applied to the surface such that only specific wavelengths are reflected, while others are transmitted.

In at least some embodiments, the device is connected wirelessly or through a wire to an external control unit. The external unit may contain control electronics, associated drivers, software, and the like, or any combination of these. It may be tethered to the wearable device with a fiber optic cable for the delivery of light. In at least some embodiments, the control unit is connected to the wearable device with a cable, supplying signals or electrical power. In at least some embodiments, the control unit interfaces wirelessly with the wearable unit. The control unit and/or wearable device may be powered by one or more batteries, or may be powered via an external power source.

In at least some embodiments, the light sources and an internal programmable controller are powered by a power source within the device. In at least some embodiments, the power source is placed at a position remote from the device. The power source may comprise one or more electronic components, including, for example, capacitors, diodes, resistors, inductors, transistors, regulators, batteries, fuel cells, or any other suitable energy storage device. It is contemplated that the power source may use any type of device, component, or system configured to store electromagnetic energy. In at least some embodiments, the power source comprises a zinc air battery, similar to those used in hearing aids.

Within certain aspects of these embodiments, the power source is rechargeable. For example, the power source can include a lithium vanadium pentoxide battery, a manganese dioxide lithium battery, a nickel cadmium battery, a nickel-metal hydride battery, a lithium ion battery, or a battery of any other suitable rechargeable battery chemistry. In at least some embodiments, the power source may comprise an inductive coil and charging circuit that can be charged inductively by an external charging station. In at least some embodiments, the power source may be an RF-powered device that can be charged by radio frequency (RF) energy. In at least some embodiments, the external power source may optionally be used to power the device.

In at least some embodiments that employ a rechargeable power source, the charge capacity of the power source is sufficient to last through at least one treatment session. Duration and frequency of the treatment required varies with the severity of the ocular disease involved. In at least some embodiments, the charge capacity need only be sufficient to power the programmable controller and light sources for 5 minutes to 30 minutes. In at least some embodiments, the treatment period is at least 20 minutes. In those subjects requiring treatment for long periods and/or at high frequencies, some embodiments employ two, three, or more power sources that are coupled to the programmable controller and light sources and provide sufficient power for the longer or more frequent treatment sessions. In at least some embodiments, a single high capacity power source can be used. In at least some embodiments, the power source can include a combination of one or more capacitors and one or more batteries.

Figure 9:
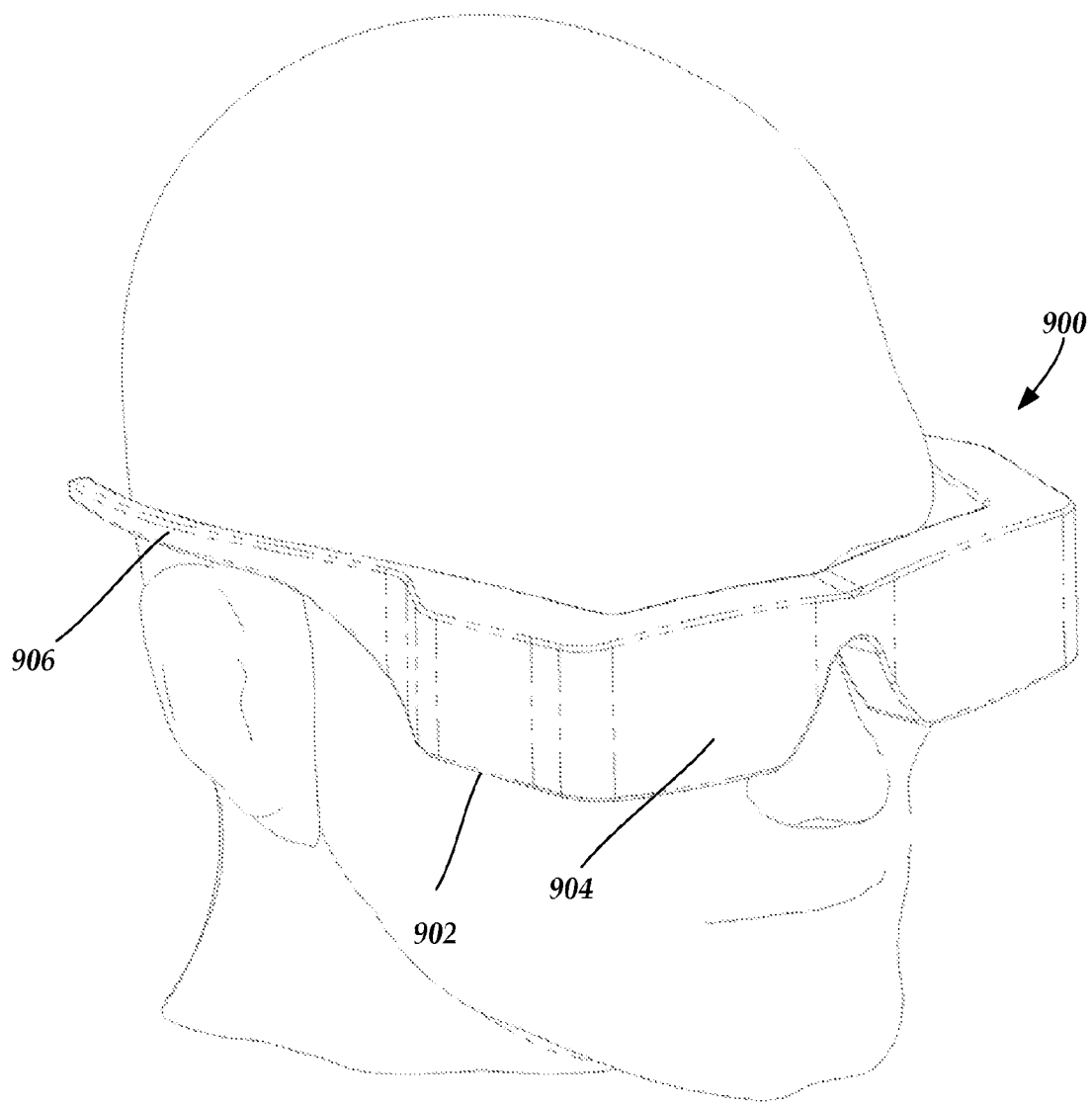
FIG. 9 is a perspective side view of one embodiment of a wearable opthalmic phototherapy device, according to the present disclosure.

FIG. 9 illustrates one embodiment of a wearable light therapy device 900. The device 900 includes a frame 902, a front piece 104 to sit in front of the patient's eyes, and two earpieces 906.

Figure 10A:
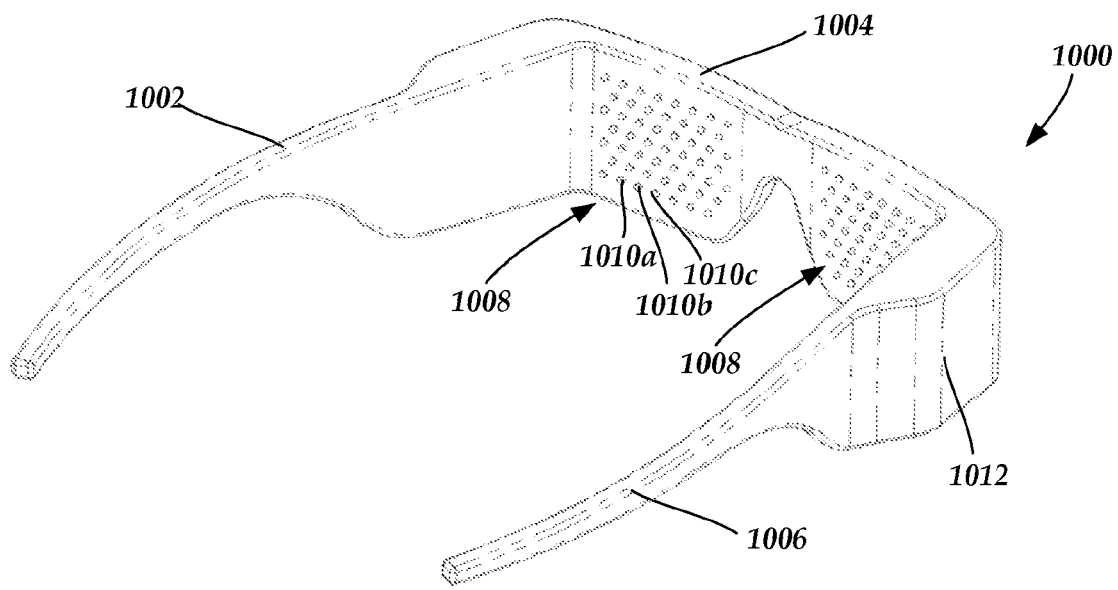
FIG. 10A is a perspective back/side view of a second embodiment of a wearable opthalmic phototherapy device, according to the present disclosure.
Figure 10B:
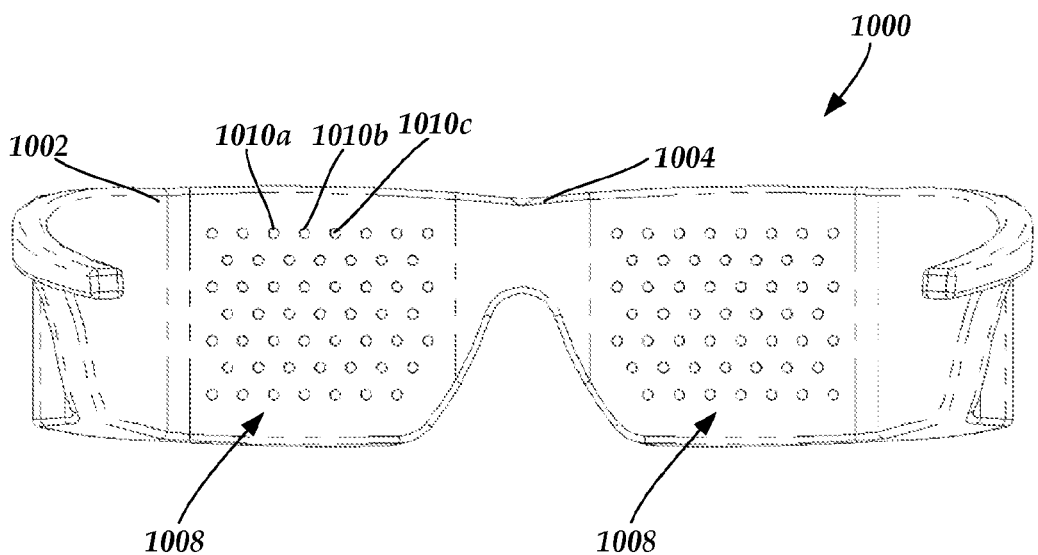
FIG. 10B is a back view of the opthalmic phototherapy device of FIG. 10A, according to the present disclosure.

FIGS. 10A and 10B illustrate one embodiment of a wearable light therapy device 1000 that includes a frame 1002, front piece 1004, earpieces 1006, right and left arrays 1008 of light sources 1010a, 1010b, 1010c and one or more frame casings 1012 in which electronics or a battery can be stored. The earpieces 1006 are one example of an affixation element of the frame 1002 which is attached to the front piece 1004 to hold the device 1000 on the wearer. Examples of other affixation elements include, but are not limited to, a headband, a helmet, a mask, or the like or any combination thereof. The light sources 1010a, 1010b, 1010c can be the same or different. The one or more frame casings 1012 can include a controller, light source electronics, a battery or any combination thereof within the casing. In at least some embodiments, the frame casing 1012 or other part of the frame 1002 may also incorporate at least one button or other user input element that can be used to initiate, terminate, or alter operation of the device 1000. Alternatively or additionally, the device can be initiated, terminated, or parameters of the light delivery can be entered or altered wirelessly or through a wired connection to a port in the frame.

Other light sources that generate or emit light with an appropriate wavelength and irradiance can also be used. In some embodiments, a combination of multiple types of light sources can be used. Each light source can optionally include one or more of a lens, diffuser, filter, or other optical elements associated with the light source. In at least some embodiments, one or more of the fluence, power, pulse length, pulse width, wavelength, or any other light emission parameter, or any combination of these parameters, of each light source can be controlled or adjusted independently of the other light sources.

In at least some embodiments with two or more different light sources 1010a, 1010b, 1010c, the individual light sources are selected to generate light of different wavelengths. For example, the arrays 1008 in the device 1000 can be arrays of three different light sources 1010a, 1010b, 1010c that can be arranged in any suitable arrangement such as, for example, a repeating sequence of light sources 1010a, 1010b, 1010c along a row or column or both or along a diagonal, a sequence (that may be repeating) with one row, column, or diagonal of light source 1010a followed by a row, column, or diagonal of light source 1010b and then a row, column, or diagonal of light source 1010c, or any other suitable regular or irregular arrangement. It will also be understood that the number of light sources emitting different wavelengths is not limited to three, but there can be two, four, five, six, or more different light sources emitting different wavelengths of light. In other embodiments, all of the light sources 1010a, 1010b, 1010c can emit the same wavelength(s) of light.

For example, in at least some embodiments, a first light source 1010a provides light of a first wavelength (which may be delivered with light of adjacent wavelengths or filtered to remove other light) and a second light source 1010b provides light of a second wavelength. In at least some embodiments, the first and second wavelengths differ by at least 25, 50, 75, 100, 150, 200, 250, 300, 400, or 500 nm. In some embodiments, a third light source 1010c provides light of a third wavelength and the third wavelength differs from the first and second wavelengths by at least 25, 50, 75, 100, 150, 200, 250, 300, 400, or 500 nm.

FIGS. 11A-11E illustrate another embodiment of a wearable light therapy device 1100 that includes a frame 1102, front piece 1104, earpieces 1106, right and left arrays 1108 of light sources 1110a, 1110b, 1110c and one or more frame casings 1112 in which electronics or a battery can be stored. All of the design considerations, properties, and description provided for similarly named elements of other embodiments is also applicable to the elements of device 1100, unless indicated otherwise. For example, the light sources 1110a, 1110b, 1110c may be the same or different or there may be one, two, three, four, or more different light sources producing different wavelengths of light.

This embodiment also includes one or more viewing ports 1105 through which the wearer can see. These viewing ports may be open or may incorporate glass or plastic which optionally form a lens. In at least some embodiments, the viewing ports 1105 incorporate prescription lenses that are selected based on the wearer's eyesight.

Figure 11A:
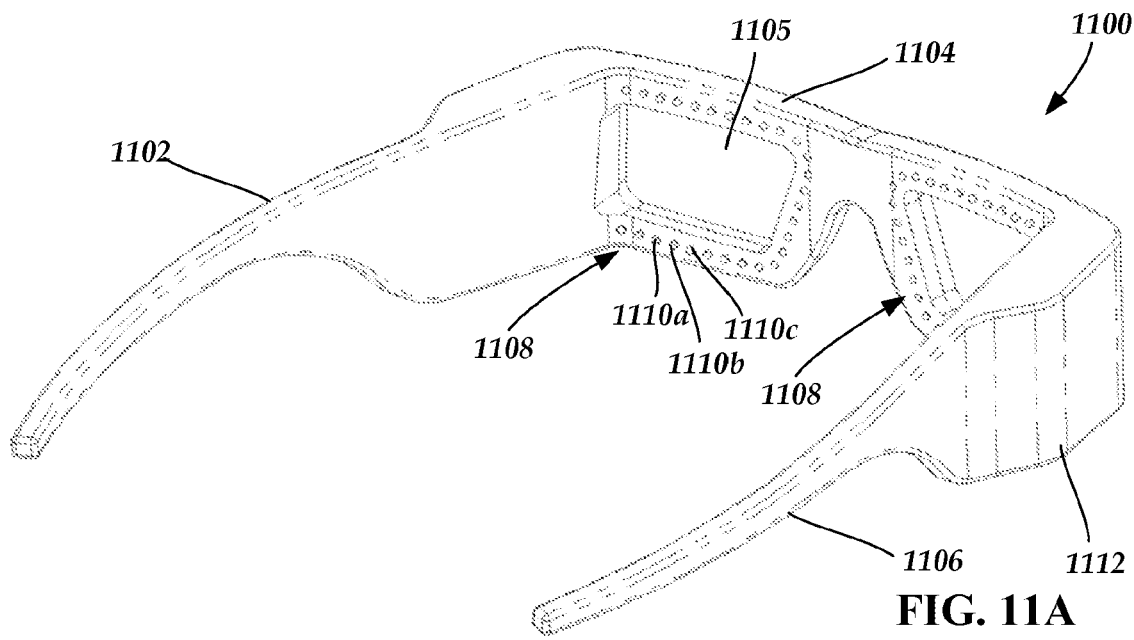
FIG. 11A is a perspective back/side view of a third embodiment of a wearable opthalmic phototherapy device, according to the present disclosure.
Figure 11B:
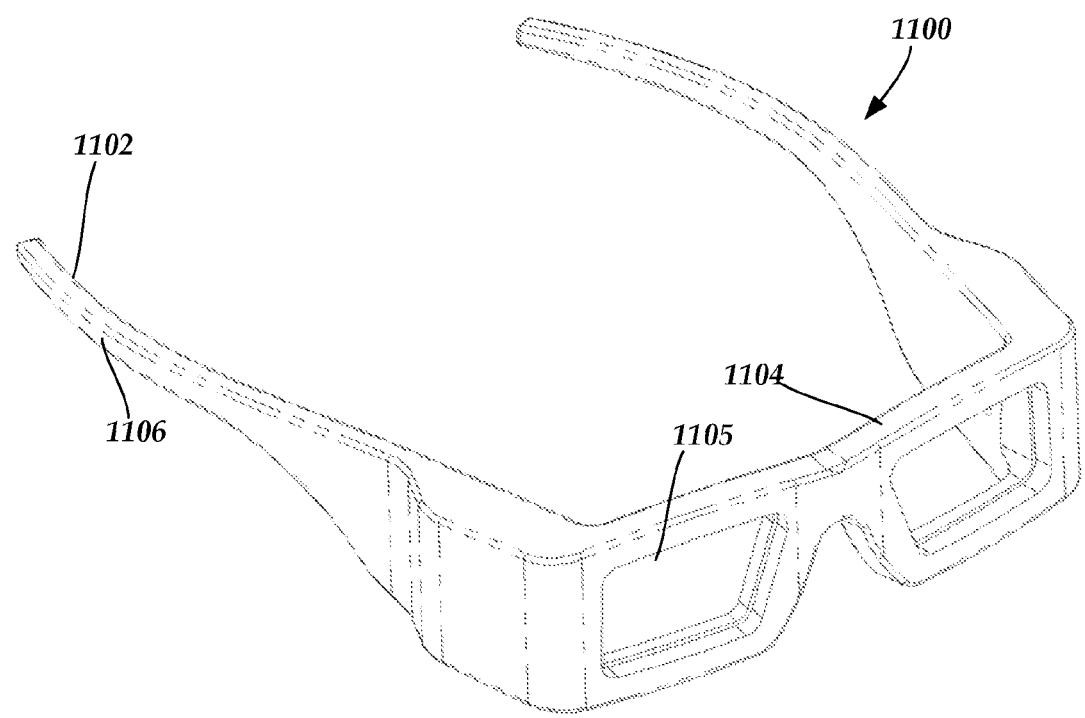
FIG. 11B is a perspective front/side view of the opthalmic phototherapy device of FIG. 11A, according to the present disclosure.
Figure 11C:
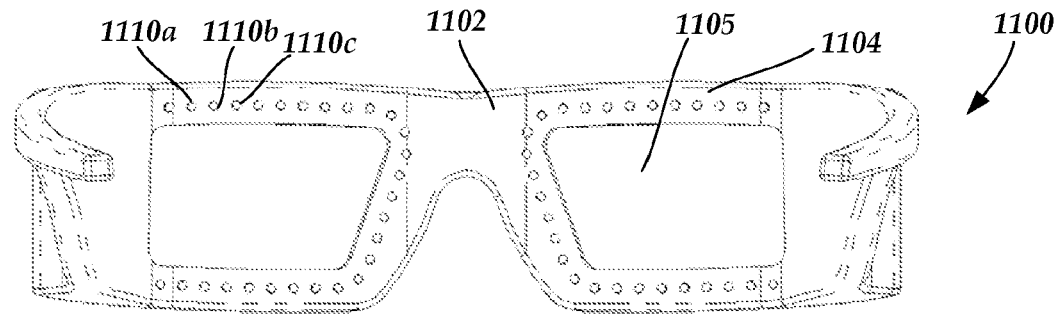
FIG. 11C is a back view of the opthalmic phototherapy device of FIG. 11A, according to the present disclosure.
Figure 11D:
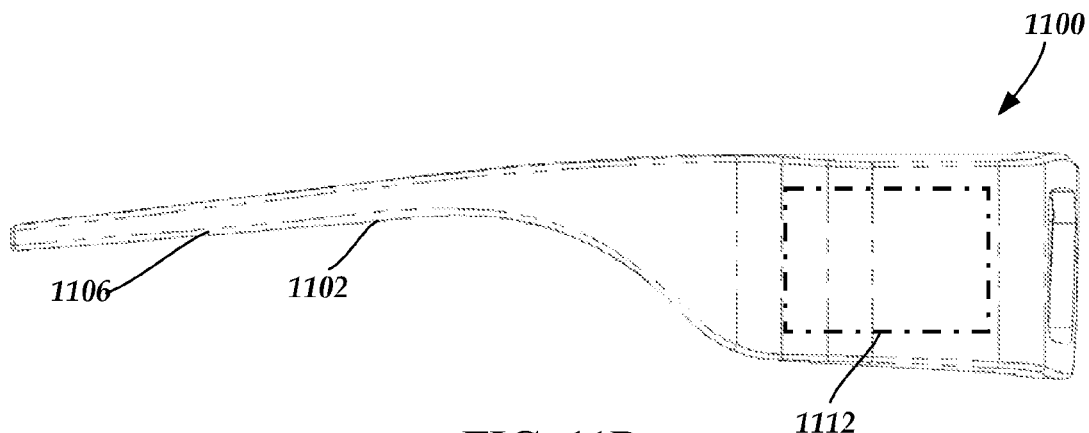
FIG. 11D is a side view of the opthalmic phototherapy device of FIG. 11A, according to the present disclosure.
Figure 11E:
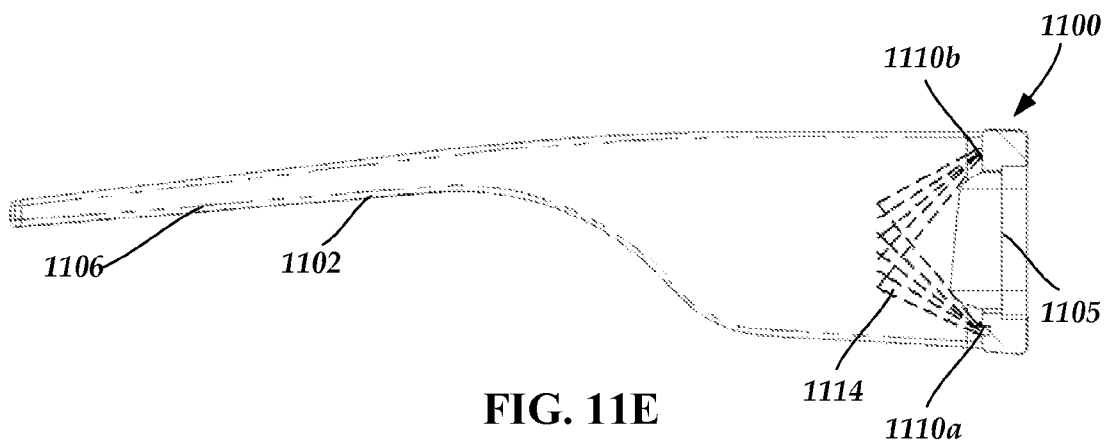
FIG. 11E is a cross-sectional view of the opthalmic phototherapy device of FIG. 11A showing the direction of light travel to the eye of the wearer, according to the present disclosure.

As particularly illustrated in FIGS. 11A and 11C, the light sources 1110a, 1110b, 1110c are arranged around the three sides of the viewing ports 1105. In other embodiments, the light sources may be arranged around one, two, four, or more sides (when the port has more than four sides) of the viewing port. The light sources 1110a, 1110b, 1110c are arranged to produce light 1114 that is at least partially directed toward the wearer's eye, as illustrated in FIG. 11E. In at least some embodiments, the light sources may be oriented toward the wearer's eye or may include at least one optical element (for example, a lens or reflector) that directs or redirects light towards the wearer's eye. In other embodiments, the light source simply generates light in a cone of directions, some of which reach the wearer's eye.

Figure 12A:
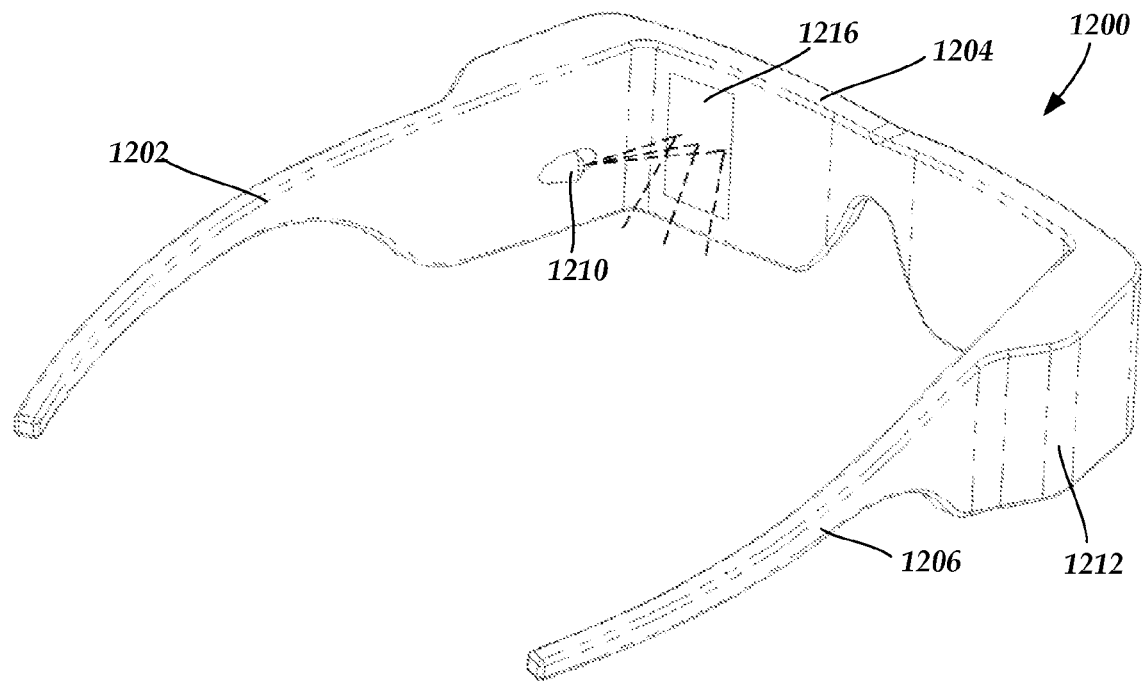
FIG. 12A is a perspective back/side view of a fourth embodiment of a wearable opthalmic phototherapy device, according to the present disclosure.

FIG. 12A illustrates another embodiment of a wearable light therapy device 1200 that includes a frame 1202, front piece 1204, earpieces 1206, light source 1210 and one or more frame casings 1212 in which electronics or a battery can be stored. All of the design considerations, properties, and description provided for similarly named elements of other embodiments is also applicable to the elements of device 1200, unless indicated otherwise.

The light source 1210 can provide different wavelengths of light using separate light generating elements (for example, LEDs, laser diodes, or the like) within the frame and directed through the light source 1210. Alternatively or additionally, there may be multiple light sources 1210 disposed on the frame in a row column or other arrangement. Although a single light source on the left earpiece is illustrated, it will be understood that there can be a similar light source on the right earpiece, as illustrated in FIG. 12C.

A reflector 1216 is provided on the frame to receive the light from the light source 1210 and redirect at least a portion of the light to the wearer's eye. The reflector 1216 can be any suitable reflector including, but not limited to, a mirror, reflective filter, reflective polarizer, beamsplitter, or the like, which redirects at least a portion of the light to the wearer's eye. The reflector 1216 may also include one or more diffusing elements, such as light scattering features, that diffuse the redirected light.

Figure 12B:
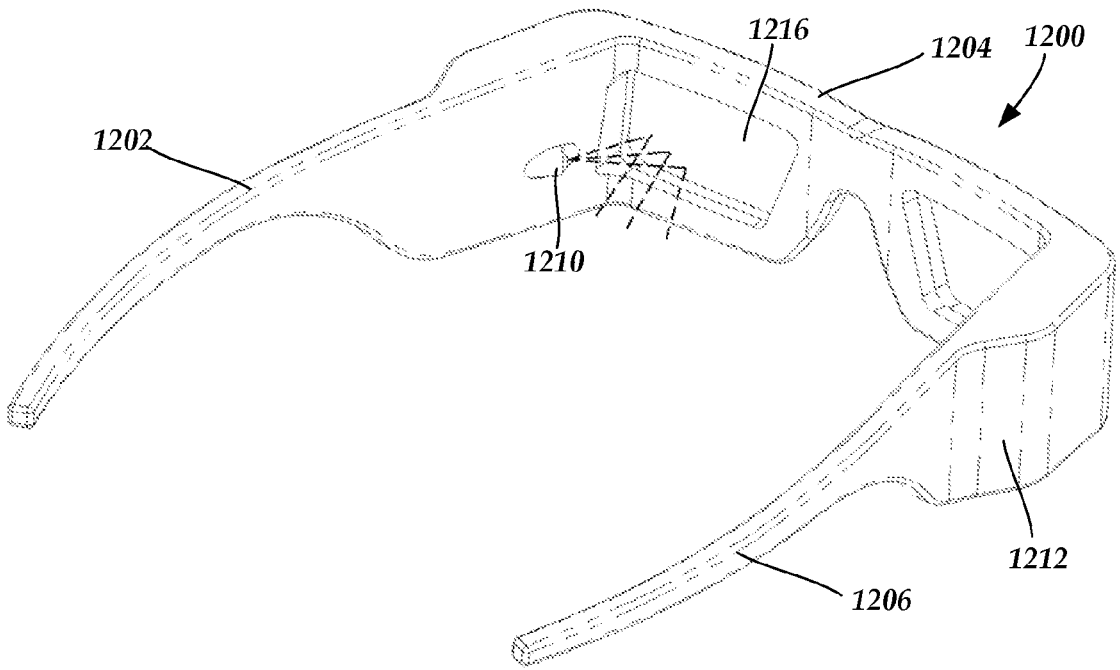
FIG. 12B is a perspective back/side view of a fifth embodiment of a wearable opthalmic phototherapy device, according to the present disclosure.
Figure 12C:
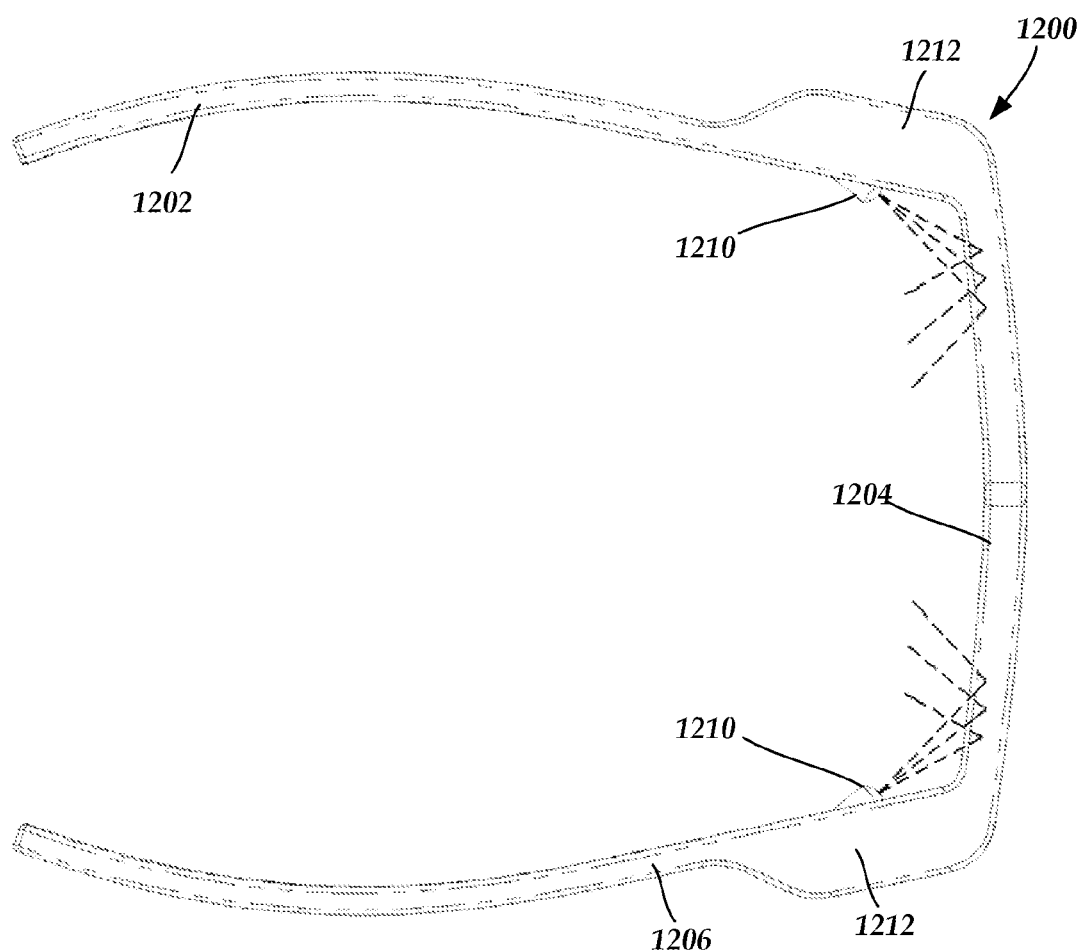
FIG. 12C is a top view of the opthalmic phototherapy device of either FIG. 12A or FIG. 12B showing the direction of light travel to the eye of the wearer, according to the present disclosure.

FIG. 12B illustrates a similar embodiment of a wearable light therapy device 1200 that includes a frame 1202, earpieces 1206, light source 1210 and one or more frame casings 1212 in which electronics or a battery can be stored. All of the design considerations, properties, and description provided for similarly named elements of other embodiments is also applicable to the elements of device 1200, unless indicated otherwise.

In the embodiment of FIG. 12B, the reflector 1216 is partially transparent so that it partially reflects light and partially transmits light. For example, this reflector 1216 can be a partial mirror, a reflective polarizer, or a reflective filter that reflects light of a particular wavelength or band of wavelengths and transmits light of other wavelengths, or the like. The reflector 1216 redirects at least a portion of the light from the light source to the wearer's eye. The reflector 1216 may be part of, or disposed on, a lens. The reflector 1216 may also include one or more diffusing elements, such as light scattering features, that diffuse the redirected light.

FIGS. 13A-13D illustrate yet another embodiment of a wearable light therapy device 1300 that includes a frame 1302, front piece 1304, earpieces 1306, light source 1310 and one or more frame casings 1312 in which electronics or a battery can be stored. All of the design considerations, properties, and description provided for similarly named elements of other embodiments is also applicable to the elements of device 1300, unless indicated otherwise. The light source 1310 can provide different wavelengths of light using separate light generating elements (for example, LEDs, laser diodes, or the like) within the light source 1310.

Figure 13A:
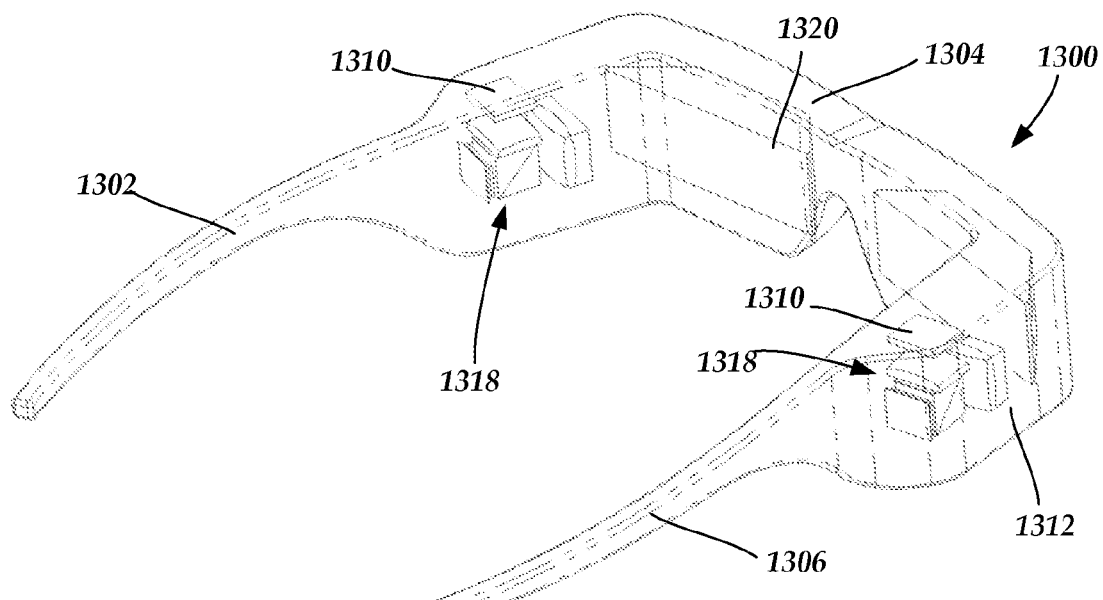
FIG. 13A is a perspective back/side view of a sixth embodiment of a wearable opthalmic phototherapy device, according to the present disclosure.
Figure 13B:
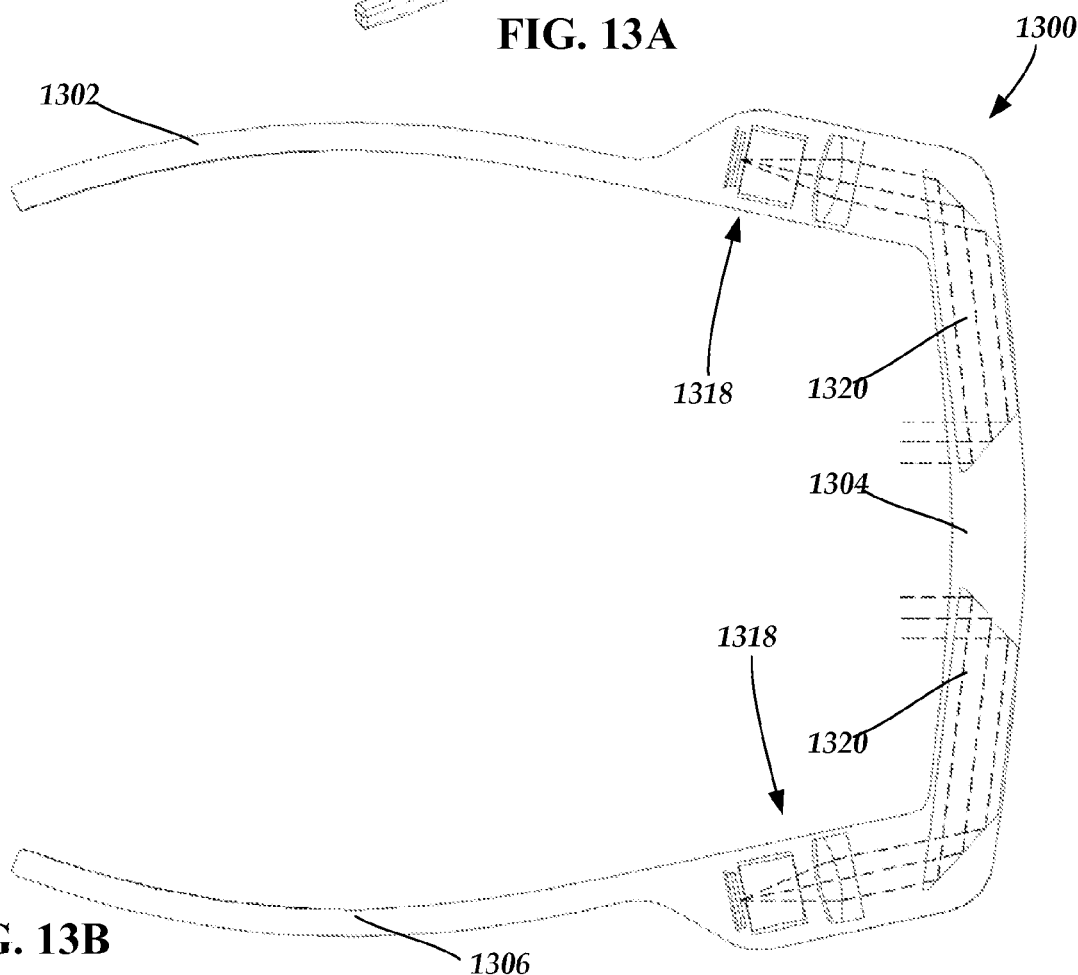
FIG. 13B is a top view of the opthalmic phototherapy device of FIG. 13A, according to the present disclosure.
Figure 13C:
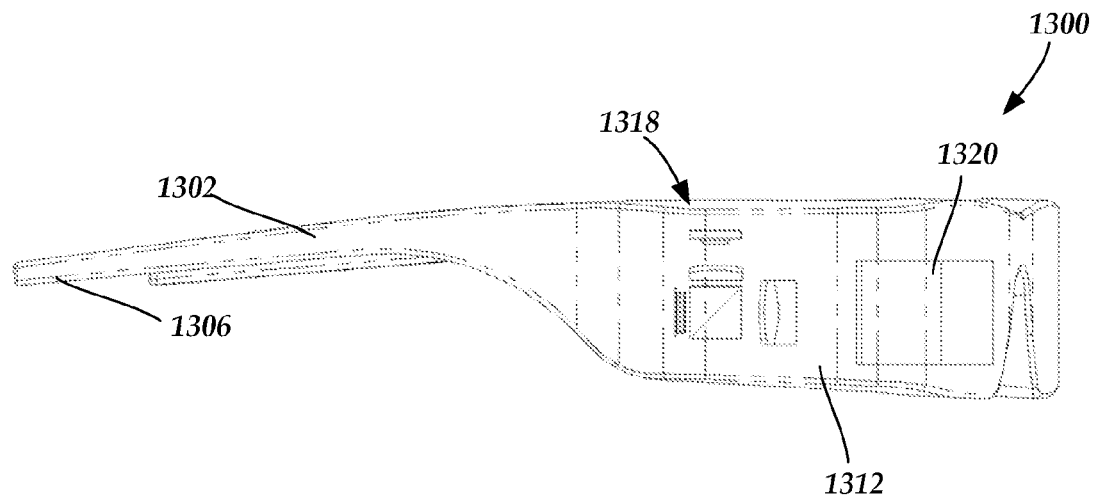
FIG. 13C is a side view of the opthalmic phototherapy device of FIG. 13A, according to the present disclosure.
Figure 13D:
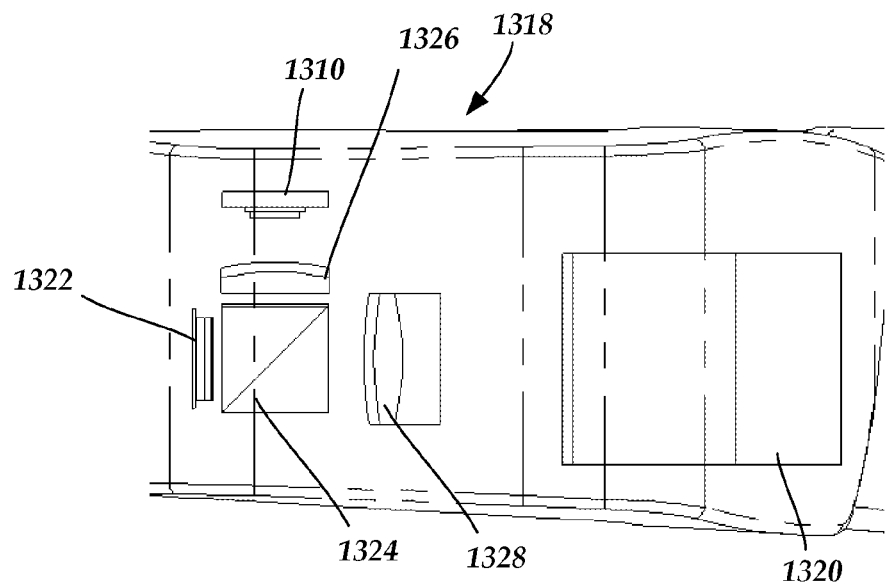
FIG. 13D is a close-up view of the projection system of the opthalmic phototherapy device of FIG. 13A, according to the present disclosure.

This device 1300 includes projection systems 1318 and a reflective prisms 1320 to provide light therapy in the form of light beams or even images to the wearer. FIG. 13D illustrates the projection system 1318 in more detail including the light source 1310, a spatial light modulator (SLM) 1322, a beamsplitter 1324, illumination optics 1326, and projection optics 1328. The spatial light modulator 1322 can be, for example, a liquid crystal on silicon (LCOS) display, a liquid crystal display (LCD), a micromirror array such as a digital light processor (DLP), a scan mirror, or any other suitable device that can reflect light and optionally can be used to form an image. The illumination optics 1326 and projection optics 1328 can include, for example, one or more lenses, diffusers, polarizers, filters, or the like.

At least a portion of the light generated from the light source 1310 is transmitted through the illumination optics 1326 redirected by the beamsplitter 1324 to the spatial light modulator 1322. The light is reflected by the spatial light modulator, which may form an image using the light or otherwise modulate the received light, back through the beamsplitter 1324 and the projection optics 1328 to the prism 1320. As illustrated in FIG. 5B, at least a portion of the light entering the prism 1320 is redirected to the wearer's eye.

Figure 14A:
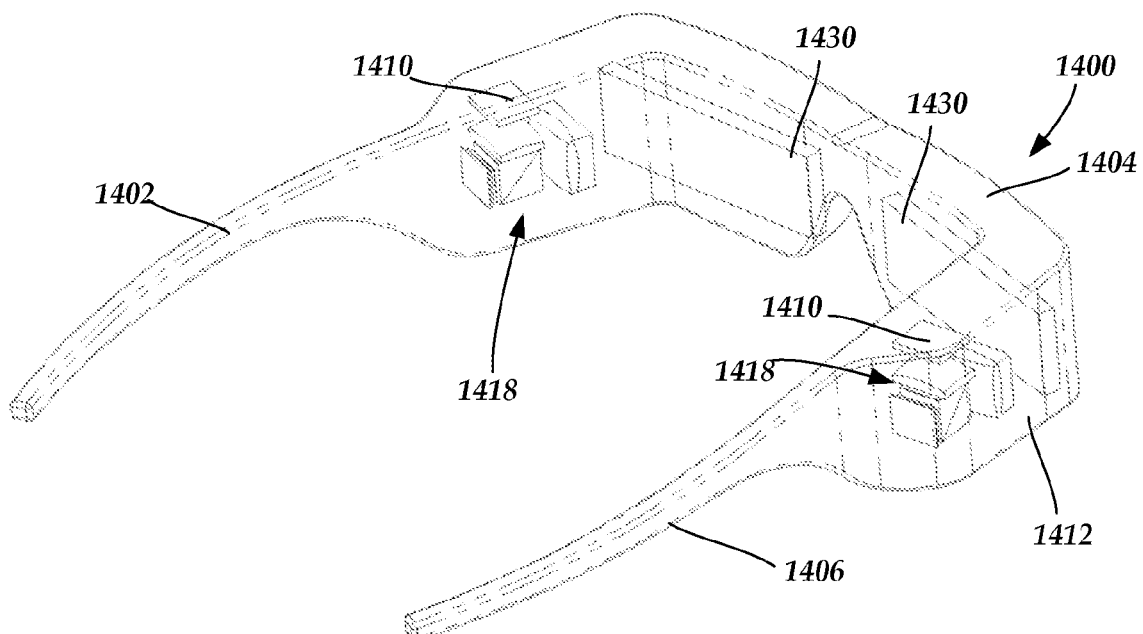
FIG. 14A is a perspective back/side view of a seventh embodiment of a wearable opthalmic phototherapy device, according to the present disclosure.
Figure 14B:
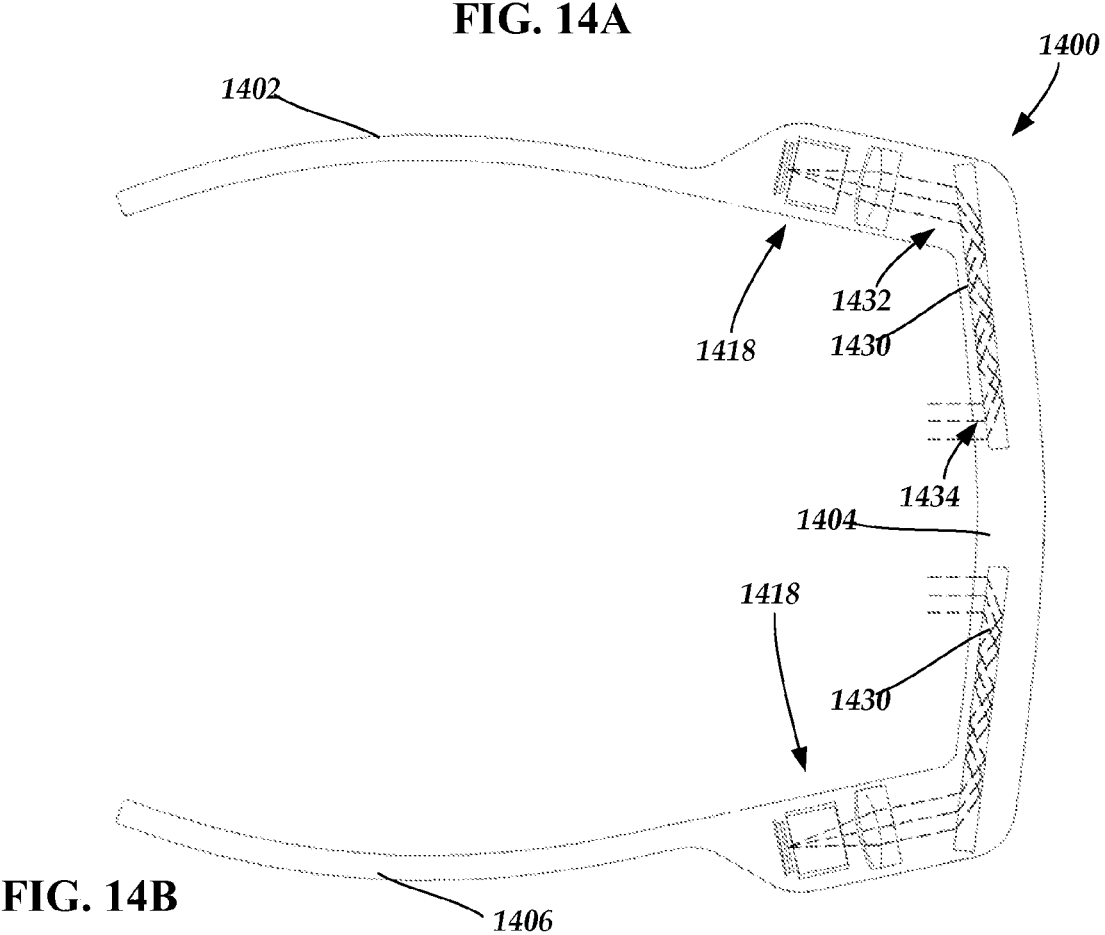
FIG. 14B is a top view of the opthalmic phototherapy device of FIG. 14A, according to the present disclosure.
Figure 14C:
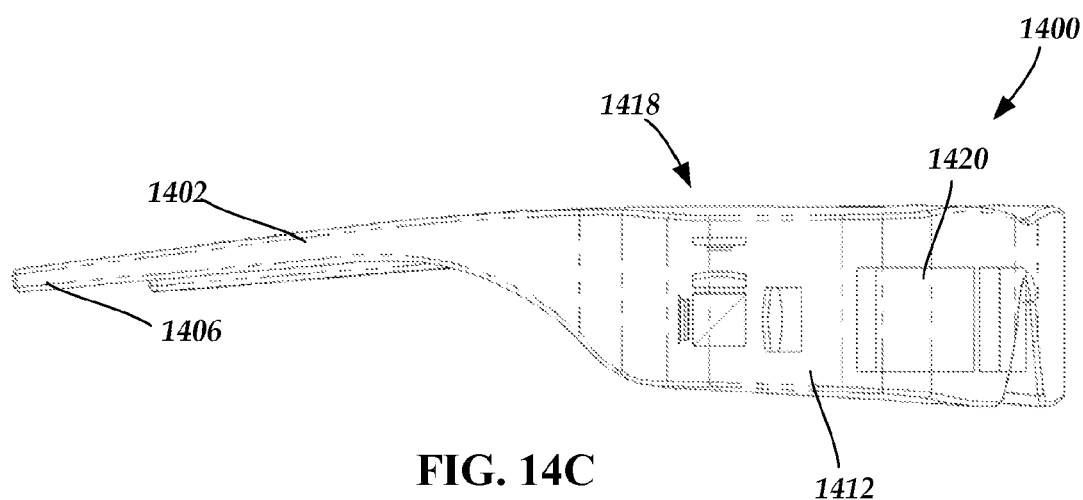
FIG. 14C is a side view of the opthalmic phototherapy device of FIG. 14A, according to the present disclosure.
Figure 14D:
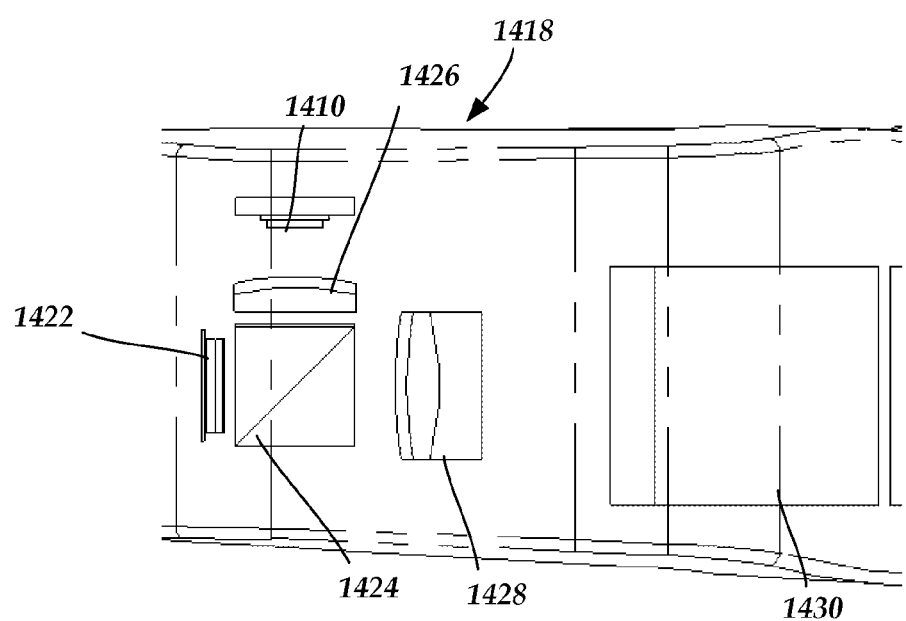
FIG. 14D is a close-up view of the projection system of the opthalmic phototherapy device of FIG. 14A, according to the present disclosure.

FIGS. 14A-14D illustrate yet another embodiment of a wearable light therapy device 1400 that includes a frame 1402, front piece 1404, earpieces 1406, light source 1410 and one or more frame casings 1412 in which electronics or a battery can be stored. This device 1400 also includes projection systems 1418 and a waveguides 1430 to provide light therapy in the form of light beams or even images to the wearer. FIG. 14D illustrates the projection system 1418 in more detail including the light source 1410, a spatial light modulator (SLM) 1422, a beamsplitter 1424, illumination optics 1426, and projection optics 1428. All of the design considerations, properties, and description provided for similarly named elements of other embodiments is also applicable to the elements of device 1400, unless indicated otherwise. The light source 1410 can provide different wavelengths of light using separate light generating elements (for example, LEDs, laser diodes, or the like) within the light source 1410.

In contrast to the embodiment of FIGS. 13A-13D, the embodiment of FIGS. 14A-14D uses a waveguide 1430 to deliver at least a portion of the light to the wearer's eye, as illustrated in FIG. 14B. The waveguide 630 may include an in-coupling diffractive optic 1432 or other arrangement to receive light from the projection system 1418 and may include an out-coupling diffractive optic 1434 or other arrangement to direct light from the waveguide to the wearer's eye. The waveguide 1430 and the prism 1320 are examples of light directing elements that receive a modulated light beam from the spatial light modulator 1322, 1422 and direct the light to the wearer's eye.

Figure 15:
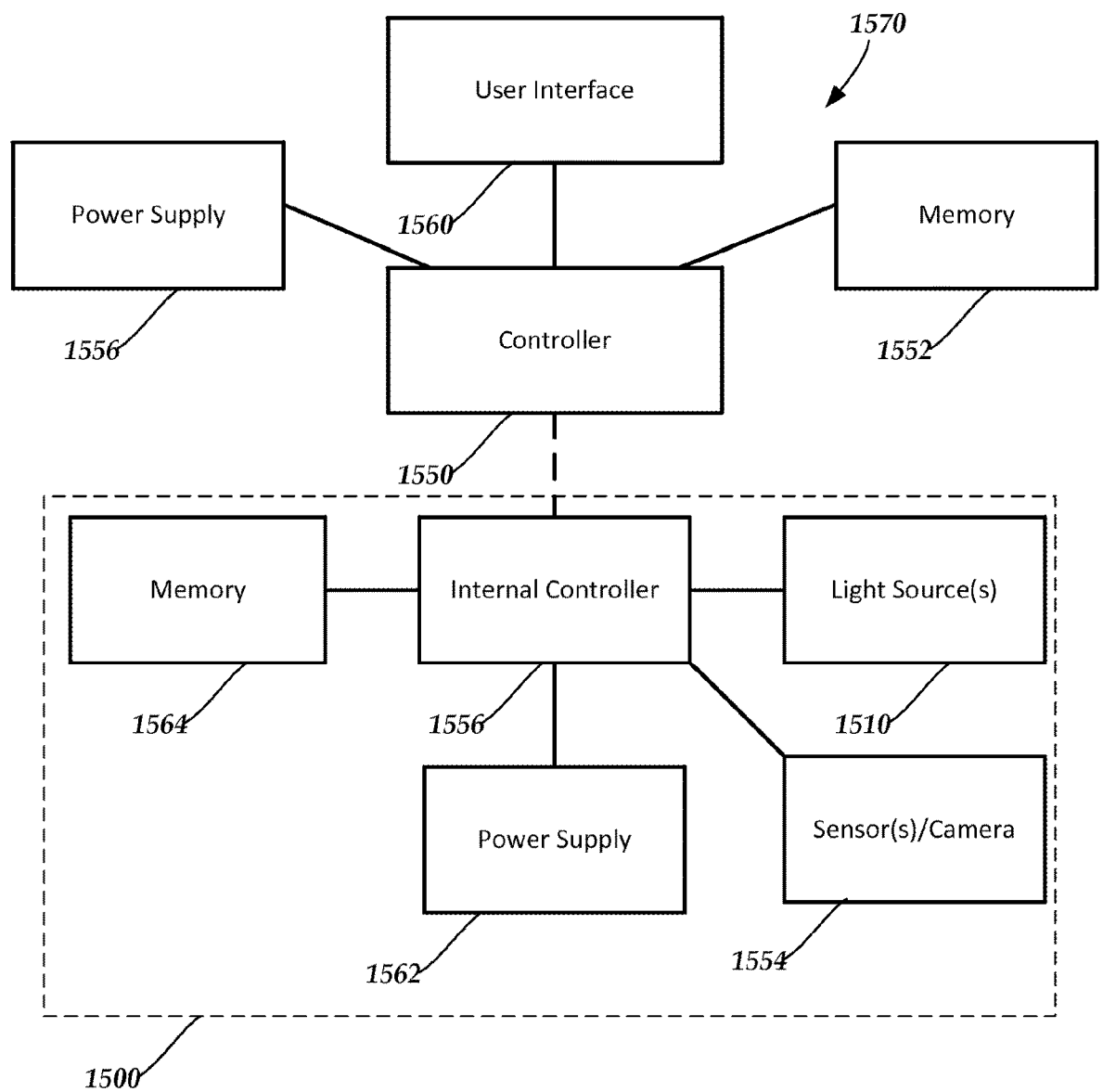
FIG. 15 is a schematic block diagram of components of one embodiment of a system for providing light therapy, according to the present disclosure.

FIG. 15 illustrates another embodiment of a system 1570 for operating the devices for treatment of ocular disease, disorders, degeneration, and the like. The system 1570 includes a controller 1550, a user interface 1560, a power supply 1556, a memory 1552, and one or more wearable devices 1500 (for example, any of the wearable devices 900, 1000, 1100, 1200, 1300, 1400 described above). The wearable device 1500 includes the light source(s) 1510 (for example, light sources 910*a*, 910*b*, 910*c*, 1010*a*, 1010*b*, 1010*c*, 1110*a*, 1110*b*, 1110*c*, 1210, 1310, 1410 described above), an optional internal controller 1556, one or more optional sensor(s)/camera 1554, memory 1564, and a power supply 1562. Alternatively or additionally, the sensor(s)/camera 1554 can be external to the device 1500, but provide information to either external controller 1550 or internal controller 1556. These components are described in more detail below. It will be recognized that other systems can include more or fewer components and that the components may be linked together in arrangements different from those illustrated in FIG. 15. In addition, any linkage between components can be through wired or wireless communication or any combination thereof.

The illustrated system 1570 includes an external controller 1550 that can communicate wirelessly or through a wired connection (or any combination thereof) with an internal controller 1556 in the wearable device 1500 to program the internal controller. In at least some embodiments, the external controller 1550 is used only to program the internal controller 1556 that operates the device 1500. In some embodiments, a medical professional may only have access to the external controller 1550. In other embodiments, the user may also have access to the external controller or to another external controller to modify, initiate, or terminate the therapy. It will be understood that the functions described herein as being performed by one of the external or internal controllers can, in other embodiments, be performed by the other one of the external or internal controller.

It will be recognized that in other systems, the wearable device may include a user interface on the device, attachable to the device, or capable of wireless communication with the device so that an external controller is unnecessary. A medical profession or, optionally, the user may employ this user interface to directly program the internal controller 1556.

In some embodiments, the device may also include one or more non-light energy sources or the device may be used in conjunction with another device that produces one or more non-light energy sources, such as magnetic energy sources, radio frequency sources, DC electric field sources, ultrasonic energy sources, microwave energy sources, mechanical energy sources, electromagnetic energy sources, and the like. For example, the phototherapy could be combined with OCT, PET, MM, femtosensors, or the like to provide instruments with therapeutic, diagnostic, tracking or enhanced targeting capabilities.

Programmable Controller

To tailor one or more of the light energy emission, light energy intensity, light energy duration, frequency, area or sequence of application of light energy to a subject's ocular tissue, or other treatment parameters, at least some embodiments include a programmable controller (for example, controller 750 of FIG. 7 or internal controller 1550 of FIG. 15 that may be part of user interface 708 or user interface 1560 directly or through an external controller 1550) or may be coupled to the user interface or may be separately coupled to the device. The programmable controller executes a set of program instructions that are stored in memory to accomplish tasks or operations such as, but not limited to, operating the one or more light sources according to a particular therapeutic regimen, communicating with external devices, monitoring the condition of elements such as the light sources and the power source, storing parameters or program instructions in the memory, and the like.

For example, the programmable controller can be used to transmit light to specific target regions of the eye according to a therapeutic regimen. For example, the programmable controller can execute a treatment program that includes a set of activation times or periods during which each of the light sources is in an emitting state and a set of inactivation times or periods during which the light source is in a non-emitting state. In certain embodiments, the programmable controller comprises a general or a special purpose microprocessor. In at least some embodiments, the programmable controller can include an application-specific integrated circuit (ASIC) or Field Programmable Gate Array (FPGA).

In at least some embodiments, the programmable controller can communicate with internal memory (for example, memory 752 of FIG. 7 or memory 1564 of FIG. 15) to retrieve or store data or program instructions for software or hardware. In at least some embodiments, the programmable controller can communicate with internal memory (for example, memory 1564 of FIG. 15) to retrieve or store data or program instructions for software or hardware. In at least some embodiments, the programmable controller comprises a central processing unit (CPU). The programmable controller can further include memory, such as random access memory (RAM) for temporary storage of information or flash memory, read only memory (ROM), EPROM memory, or EEPROM memory for permanent storage of information.

In at least some embodiments, the memory can be reprogrammable after the initial programming. Additionally, the programmable controller can include a real time clock, one or more timers, an analog to digital (A/D) converter, a digital to analog (D/A) converter, a serial communications interface, such as $I^2C$ or Serial Peripheral Interface, a communications interface, or a pulse width modulation (PWM) generator. The power source can provide power to the programmable controller, which in turn can drive the one or more light sources. In at least some embodiments, the programmable controller drives the one or more light sources through a light source driver. The light source driver can provide an appropriate current or voltage level to energize the one or more light sources. When the programmable controller generates a control signal to drive a light source, light is emitted from the emission surface. In contrast, when the light source is not receiving a control signal from the programmable controller to generate light, the emission surface is in a non-emitting state. The light sources can be configured to emit light continuously or periodically in accordance with various therapeutic regimens.

In at least some embodiments, the programmable controller is preprogrammed (e.g., prior to implantation) with a desired set of treatment parameters for a given subject (e.g., patient). For example, a desired frequency of light energy emission (e.g., every 24 hours), duration of light energy emission (e.g., for 5 minutes), irradiance of light energy emission (e.g., from 1 mW to 10 mW), irradiation pattern or order of light source activity (e.g., a sequence of emission of light energy in those embodiments comprising more than one light source), and other parameters can be preprogrammed into the programmable controller. For pulsed light dosimetry, the treatment parameters can also include duty cycle, pulse shape, repetition rate, pulse width or irradiance per pulse for pulsed light dosimetry.

In at least some embodiments utilizing multiple light sources, the programmable controller can be programmed to activate a subset of the light sources to focus on a particular target region. In at least some embodiments, the programmable controller can be programmed to activate the light sources according to a predetermined treatment regimen, order, template, or sequence. For example, the treatment regimen can follow a pattern similar to the sequences described in paragraphs [0203]-[0228] of U.S. Patent Application Publication No. 2009/0254154, incorporated by reference herein. The treatment regimen can also be adjustable by a physician (e.g., via telemetry or a wireless or wired network interface).

In at least some embodiments, the programmable controller can be reprogrammed dynamically via a communications interface. The communications interface can comprise an antenna configured to receive RF communication from an external telemetry unit. The communications interface can also be configured to transmit information to the external telemetry unit. Other types of wireless communication links can also be used. In at least some embodiments, a physician can adjust treatment parameters in response to an alarm or warning generated by the light therapy apparatus. The physician can reprogram the programmable controller wirelessly via the communications interface.

In at least some embodiments, the programmable controller can automatically reprogram itself or recalibrate its treatment parameters in response to control signals received from feedback sensors (for example, sensor 754 of FIG. 7). The sensors can provide feedback regarding the parameters of the light treatment or the physiological parameters of the subject (e.g., patient). The sensors (for example, sensor 754 of FIG. 7) can include biomedical sensors, biochemical sensors, temperature sensors, and the like. In at least some embodiments, the sensors can be invasive sensors and can be implanted within the body, or attached to the body, at least temporarily. In at least some embodiments, the sensors can comprise noninvasive or minimally invasive sensors.

The sensors can be used to measure, for example, adenosine triphosphate (ATP) levels or activity, optic nerve outputs waves (e.g., using an ERG sensor system), mitochondrial activity (e.g., by measuring NADH or NADPH levels), nitric oxide (NO) production or consumption, cytokines (such as IL-6 interleukins and tumor necrosis factors (TNF)), apoptotic markers (such as Bax and Bcl-2), evoked response optical scanning (EROS) responses, oxygen consumption levels, membrane potential, glycolysis activity, or pH levels. For example, increases in cellular ATP concentration and a more reduced state within the cell are both related to cellular metabolism and are considered to be indications that the cell is viable and healthy. The increased concentration of NADH within the targeted ocular tissue and a corresponding improvement in the redox state of the targeted ocular tissue reflects both the metabolic activities and the health of cells.

Diffusion

In at least some embodiments, the light source or the device includes one or more diffusers adapted to diffuse the light prior to reaching the eye or ocular tissue to advantageously homogenize the light beam. Generally, intervening tissues of the cornea are highly scattering which can reduce the impact of non-uniform beam intensity distributions on the illumination of the subject's retina. However, non-uniform beam intensity distributions with substantial inhomogeneities non-homogeneities could result in some portions of the subject's eye being heated more than others (e.g., localized heating where a "hot spot" of the light beam impinges the subject's eye).

In at least some embodiments, the light source, or other components within the device, advantageously homogenizes the light beam to reduce non-uniformities. An example energy density profile of the light prior to being transmitted through the light source, is peaked at a particular emission angle. In at least some embodiments, after being diffused by the light source or other components in the device, the energy density profile of the light does not have a substantial peak at any particular emission angle, but is substantially evenly distributed among a range of emission angles. By diffusing the light, the light source or other components within the device distribute the light energy substantially evenly over the area to be illuminated, thereby controlling, inhibiting, preventing, minimizing, or reducing "hot spots" which would otherwise create temperature increases at the eye. Thus, by virtue of diffusing the light, the temperature of the irradiated portion of the subject's eye is lower than it would otherwise be if the device did not diffuse the light. For example, by diffusing the light, the temperature of the irradiated portion of the subject's eye can be higher than the temperature of the portion of the subject's eye if it were not irradiated, but lower than the temperature of the portion of the subject's eye if it were irradiated but the light were not diffused. In addition, by diffusing the light prior to reaching the eye, the device can effectively increase the spot size of the light impinging the eye, thereby advantageously lowering the irradiance at the eye.

In at least some embodiments, the light source or other components in the device provide sufficient diffusion of the light such that the irradiance of the light is less than a maximum tolerable level of the eye, or other ocular tissue. For example, the maximum tolerable level of certain embodiments is a level at which the subject experiences discomfort or pain, while in certain other embodiments, the maximum level is a level at which the subject's eye or ocular tissue is damaged (e.g., thermal damage or burned). In at least some embodiments, the device provides sufficient diffusion of the light such that the irradiance of the light equals a therapeutic value at the target tissue. The device can include diffusers such as, but are not limited to, holographic diffusers such as those available from Physical Optics Corp. of Torrance, California and Display Optics P/N SN1333 from Reflexite Corp. of Avon, Connecticut Targeting Light therapy may be administered through a closed eyelid, in which much of the light can be expected to scatter over a relatively broad area of the retina, or it may be administered to the open eye. In the case of the open eye, it is expected that the majority of the therapeutic light will be delivered to the retina through the lens and pupil of the eye with minimal scattering. In certain embodiments, the device includes the ability to target specific areas of the retina through the pupil. This can be accomplished through the inclusion of a Spatial Light Modulator (SLM) to precisely shape and control the exposed area on the retina. The SLM may be an LCOS panel, scanning mirror, deformable mirror array, or other modulation device.

In at least some embodiments, the SLM, in combination with illumination and imaging optics, provides static or moving images to the patient. The images may be used to aid in the control of the treated eye's focus and orientation during therapy by directing the patient's gaze, or they may function to increase the usability of the device by providing visual entertainment to the patient during therapy. In certain embodiments, the illumination source of the SLM is used only for image display, while therapy is provided via a secondary light source or sources. In other embodiments, the SLM illumination source, or sources, provides the therapy.

Feedback

In at least some embodiments, the programmable controller includes a logic circuit, a clock coupled to the logic circuit, and an interface coupled to the logic circuit. The clock of at least some embodiments provides a timing signal to the logic circuit so that the logic circuit can monitor and control timing intervals of the applied light. Examples of timing intervals include, but are not limited to, total treatment times, pulse width times for pulses of applied light, and time intervals between pulses of applied light. In at least some embodiments, the light source can be selectively turned on and off to reduce the thermal load on the eye or ocular tissue and to deliver a selected irradiance to particular areas of the eye or other ocular tissue.

The interface of at least some embodiments provides signals to the logic circuit, which the logic circuit uses to control the applied light. The interface can comprise a user interface or an interface to a sensor (for example, sensor 754 of FIG. 7 or sensor 1554 of FIG. 15) monitoring at least one parameter of the treatment. In at least some embodiments, the programmable controller is responsive to signals from the sensor to preferably adjust the treatment parameters to optimize the measured response. The programmable controller can thus provide closed-loop monitoring and adjustment of various treatment parameters to enhance or optimize the phototherapy. The signals provided by the interface from a user are indicative of parameters that may include, but are not limited to, individual subject characteristics (e.g., eye lid skin type, fat percentage), selected applied irradiances, target time intervals, and irradiance/timing profiles for the applied light.

In at least some embodiments, the logic circuit is coupled to a light source driver and the light source driver is coupled to a power supply (for example, power supply 756 of FIG. 7 or power supply 1562 of FIG. 15), which in at least some embodiments is a battery or capacitive energy storage device and in other embodiments includes an alternating current source. The light source driver is also coupled to the light source. The logic circuit is responsive to the signal from the clock and to user input from the user interface to transmit a control signal to the light source driver. In response to the control signal from the logic circuit, the light source driver adjusts and controls the power applied to the light source. In at least some embodiments, the control circuit can be used to provide real-time positive or negative feedback.

In at least some embodiments, the logic circuit is responsive to signals from a sensor monitoring at least one parameter of the treatment to control the applied light. For example, at least some embodiments include a temperature sensor in thermal communication with the skin or eyelid to provide information regarding the temperature of the skin to the logic circuit. In at least some embodiments, the logic circuit is responsive to the information from the temperature sensor to transmit a control signal to the light source driver so as to adjust the parameters of the applied light to maintain the skin or eyelid temperature below a predetermined level. Other examples of suitable sensors include other biomedical sensors including, but not limited to, a blood flow sensor, a blood gas (e.g., oxygenation, femtosensor) sensor, an ATP production sensor, or a cellular activity sensor. Such biomedical sensors can provide real-time feedback information to the logic circuit.

For example, if ATP production or mitochondrial activity levels are below a certain threshold level, the logic circuit can generate a control signal to the light source(s) to adjust a treatment parameter of the applied light, such as a treatment time, wavelength, irradiance level, or other parameter. In at least some embodiments, the logic circuit is responsive to signals from a sensor or sensors to preferably adjust the parameters of the applied light to enhance or optimize the measured response. The logic circuit can thus provide automatic real-time closed-loop monitoring and adjustment of various parameters of the applied light to enhance or optimize the phototherapy. In other embodiments, the control circuit can be configured to provide manual closed-loop feedback. The sensors (for example, sensor 754 of FIG. 7 or sensor 1554 of FIG. 15) can also include biochemical sensors, EEG sensors, EROS sensors, photosensors, or other sensors. Any sensor or combination of sensors can be used.

In at least some embodiments, the device provides a method for imaging the patient's sclera, cornea, retina, or other portion of the eye. Such an image may be obtained by directing a patient's gaze toward a specified point or other region, and then viewing or capturing an image of the desired area of the eye. In at least some embodiments, this is performed in an automated fashion, with the device automatically adjusting the focus, exposure, size, or location for the image. In at least some embodiments, the user manually determines one or more of the image capturing parameters. In at least some embodiments, information from the image is then used by the user of the device to identify and establish specific treatment or target areas of the eye. In at least some embodiments, the user manually adjusts the device output such that the desired dosage is delivered to the target areas. In at least some embodiments, the target areas are programmed into the device, and the logic circuit may then dynamically adjust the device output to deliver the desired therapy to the identified regions.

In at least some embodiments, the logic circuit is responsive to signals indicating the spatial position or orientation of the patient's eye (e.g., where the patient is looking). This may be accomplished through the use of one or more cameras (for example, camera 754 of FIG. 7 or camera 1554 of FIG. 15) and associated software algorithms. Supplementary emitters in infrared or other wavelengths may be used as illumination sources to facilitate the eye-tracking. Alternatively, commercially available eye-tracking components or algorithms may be incorporated into the device, partially or in entirety. In at least some embodiments, the logic circuit may utilize the eye-orientation signal to adjust the device output spatially to maintain the appropriate exposure on previously identified target areas. In at least some embodiments, it may use the signal to adjust the intensity of the device output. Such intensity modulation may include increasing or decreasing the device output to maintain the appropriate exposure to a given area, or it may include the temporary cessation of therapy.

In at least some embodiments, the device actively monitors the state of the patient's eyelid (e.g., open or closed) during therapy. In at least some embodiments, the signal is used as an interlock in the logic circuit, temporarily stopping output of the device if a particular eyelid state is detected. In at least some embodiments, the signal is used by the logic circuit to increase or decrease the power output of the device. The logic circuit may include a measurement of the cumulative time that a particular eyelid state exists over the course of a treatment. The total treatment time may then be automatically adjusted to deliver the total desired dosage. In at least some embodiments in which the therapy is nominally delivered through the closed eye, the logic circuit may halt therapy whenever an open-eye state is detected, or it may temporarily reduce the device output to maintain a constant irradiance on the retina or other portion of the eye. In at least some embodiments in which therapy is nominally delivered to an open eye, the logic circuit may halt therapy whenever a closed-eye state is detected, or it may temporarily increase the device output to maintain a constant irradiance on the retina or other portion of the eye.

In at least some embodiments, the device contains one or more cameras (for example, camera 754 of FIG. 7 or camera 1554 of FIG. 15) and associated software algorithms for measuring the diameter of a patient's pupil. Alternatively, the one or more cameras may be external to the device, but provide information to the device directly or indirectly. This measurement may be performed once, periodically, or continually. The logic circuit may then use the pupil diameter measurement signal to adjust treatment parameters to achieve the desired dosage on the retina.

In at least some embodiments, the device contains sensors (for example, sensor 754 of FIG. 7 or sensor 1554 of FIG. 15) to monitor the spatial or temporal irradiance pattern delivered to the patient. Within some embodiments, such as in the presently disclosed wearable devices, the one or more sensors may be external to the device, but provide information to the device directly or indirectly.

The sensor may include an array of one or more photodiodes, a camera of appropriate wavelength and time sensitivity, or another sensor capable of measuring the spatial and temporal irradiance profile of the delivered therapy. The resulting "beam profile" may then be analyzed through software within the device to determine specific characteristics of the delivered therapy, including one or more of the following: diameter (as defined by a relative encircled energy metric, or a relative intensity metric), uniformity, pulse frequency, total power, maximum intensity, etc. In at least some embodiments, the logic circuit periodically or continuously monitors the beam profile as a method to validate of the delivered therapy. In at least some embodiments, the logic circuit uses the beam profile data as feedback to modulate the output of the device to achieve the desired dosage.

In at least some embodiments, the device contains one or more cameras (for example, camera 1554 of FIG. 15) and associated software algorithms for measuring the diameter of a patient's pupil or the one or more cameras may be external to the device, but provide information to the device directly or indirectly. This measurement may be performed once, periodically, or continually. The logic circuit may then use the pupil diameter measurement signal to adjust treatment parameters to achieve the desired dosage on the retina.

In other embodiments, the device contains one or more sensors (for example, sensor 1554 of FIG. 15) to monitor the spatial or temporal irradiance pattern delivered to the patient or the one or more sensors may be external to the device, but provide information to the device directly or indirectly. The sensor may include an array of one or more photodiodes, a camera of appropriate wavelength and time sensitivity, or another sensor capable of measuring the spatial and temporal irradiance profile of the delivered therapy. The resulting "beam profile" may then be analyzed through software within the device to determine specific characteristics of the delivered therapy, including one or more of the following: diameter (as defined by a relative encircled energy metric, or a relative intensity metric), uniformity, pulse frequency, total power, maximum intensity, etc. In at least some embodiments, the logic circuit periodically or continuously monitors the beam profile as a method to validate of the delivered therapy. In at least some embodiments, the logic circuit uses the beam profile data as feedback to modulate the output of the device to achieve the desired dosage.

Pupil Dilation Monitoring

In addition to tracking the eye movement, targeting the retina, aiming the beam, and confirming eyelid position, monitoring the pupil diameter may be used to ensure the chosen beam diameter is not clipped by the pupil during therapy. If the pupil diameter were to constrict, the expected dose may not reach the target tissue. Applying pupil dilation solutions may not be desired for this therapy. Controlling pupil diameter via ambient light intensity may not be reliable or practical for this application since visible light of a defined intensity is part of the therapy. Estimating a single value for minimum pupil diameter across all patient populations may not be practical or allow all targeted tissues to be accessed through the pupil.

Light Intensity Sensors to Map Application of Light to Target Surface

In at least some embodiments, the device may include complex measurements and algorithms for monitoring light intensity. Confirmatory measurements may be prudent risk mitigations. For example, the beam profile exiting the device may be measured to confirm select parameters are being applied to the subject as intended (beam diameter, beam intensity map). In at least some embodiments, the device may reflect the beam off a 'leaky' mirror prior to exiting the device. The small amount of light penetrating the 'leaky' mirror can be sampled by a sensor array (for example, sensor 754 of FIG. 7 or 1554 of FIG. 15) to measure the selected parameters. In at least some embodiments, a camera (for example, camera 754 of FIG. 7 or 1554 of FIG. 15) can monitor light reflected from the patient. The reflected light could be sampled to identify the beam profile applied to the patient.

The various parameters of the light beam emitted from the emission surface are selected to provide treatment while controlling, inhibiting, preventing, minimizing, or reducing injury or discomfort to the subject due to heating of the skin or eye tissue by the light. While discussed separately, these various parameters below can be combined with one another within the disclosed values in accordance with embodiments described herein.

Wavelength

In at least some embodiments, light in the visible to near-infrared wavelength range is used to irradiate the subject's skin or eye tissue. In at least some embodiments, the light from a particular light source is substantially monochromatic (i.e., light having one wavelength, or light having a narrow band of wavelengths). In at least some embodiments, the desired beneficial or therapeutic biological response is established with the use of one or more selected wavelengths. In at least some embodiments, the light includes one or more wavelengths between 550 nanometers and 1064 nanometers, or between 590 nanometers and 980 nanometers. In at least some embodiments, multiple wavelengths are used (e.g. applied concurrently or sequentially). In at least some embodiments, the light of a particular desired wavelength has a wavelength distribution peaked at a peak wavelength and has a line width less than ±10 nanometers from the peak wavelength. In at least some embodiments, the light of a particular desired wavelength has a line width less than 4 nanometers, full width at 90% of energy. In at least some embodiments, the one or more chosen wavelength are selected from 590 nm±10%, 670 nm±10%, 810 nm±10%, and 1064 nm±10%, with a spectral line width less than 4 nanometers, full width at 90% of energy. In at least some embodiments, the light of a particular desired wavelength has a wavelength distribution peaked at a peak wavelength and has a line width less than ±40 nanometers from the peak wavelength at 50% of energy. In at least some embodiments, the one or more chosen wavelength are selected from 590 nm±10%, 670 nm 10%, 810 nm±10%, and 1064 nm±10%, with a spectral line width less than 40 nanometers, full width at 50% of energy.

In at least some embodiments, the selected wavelength is in a range from 800 to 900 nm including, for example, a range of 850 nm±10, 15, or 30 nm. In at least some embodiments, the selected wavelength is in a range from 600 to 700 nm including, for example, a range of 660±10, 15, or 30 nm. In at least some embodiments, the selected wavelength is in a range from 550 to 650 nm including, for example, a range of 590±10, 15, or 30 nm. In at least some embodiments, the device produces multiple wavelengths of light including, but not limited to, any combination of the wavelengths or wavelength ranges identified in this or the preceding paragraph.

In at least some embodiments, each preselected wavelength of the light is selected to be at or near a transmission peak (or at or near an absorption minimum) for the intervening tissue. In at least some embodiments, one wavelength corresponds to a peak in the transmission spectrum of tissue at or 820 nanometers (NIR). In at least some embodiments, one wavelength corresponds to a peak in the transmission spectrum of tissue at or 670 nanometers (red visible).

In at least some embodiments, the light source includes at least one continuously emitting GaAlAs laser diode having a wavelength chosen from the previous list. In at least some embodiments, the light source includes at least one LED, which each provide non-coherent light, having a wavelength chosen from the previous list.

In at least some embodiments, the one or more wavelengths are selected so as to work with one or more photoacceptors within the target tissue. Without being bound by theory or by a specific mechanism, it is believed that irradiation of one or more CCO photoacceptors for example, increases the production of ATP in the target tissue or controls, inhibits, prevents, minimizes, or reduces apoptosis of the injured tissues, thereby producing beneficial effects, as described more fully elsewhere. Other wavelengths may be chosen to work with photoacceptors to control, inhibit, or stimulate distinct biological responses in the target tissue.

Some photoacceptors, such as water or hemoglobin, are ubiquitous and absorb light to such a degree that little or no penetration of light energy into a tissue occurs. For example, water absorbs light above approximately 1300 nanometers. Thus, energy in this range has little ability to penetrate tissue due to the water content. However, water is transparent or nearly transparent in wavelengths between 300 and 1300 nanometers. Another example is hemoglobin, which absorbs heavily in the region between 300 and 670 nanometers, but is reasonably transparent above 670 nanometers. Based on these broad assumptions, one can define an "IR window" into the body. Within the window, there are certain wavelengths that are more or less likely to penetrate.

Irradiance or Power Density

In at least some embodiments, the light sources emit a light beam having a time-averaged irradiance, or power density, at the emission surface of the light sources (e.g., at the retinal surface) between 0.005 mW/cm$^2$ to 10 W/cm$^2$, 0.01 mW/cm$^2$ to 5 W/cm$^2$, 0.01 mW/cm$^2$ to 1 W/cm$^2$, 1 mW/cm$^2$ to 500 mW/cm$^2$, 500 mW/cm$^2$ to 1 W/cm$^2$, or overlapping ranges thereof, across the cross-sectional area of the light beam. In at least some embodiments, the time-averaged irradiance at the target tissue is at least 0.001 mW/cm$^2$ and up to 1 W/cm$^2$ at the level of the targeted tissue. In at least some embodiments, the time-averaged subsurface irradiance at the target tissue is at least 0.001, 0.005, 0.01, 0.05, 0.1, 0.5, 1, 5, 10, 15, 20, 30, 40, 50, 60, 70, 80, 90, 100, 200, 300, 400, 500, 600, 700, 800, 900, or 1000 mW/cm$^2$, or greater, depending on the desired clinical performance.

For a pulsed light beam, the time-averaged irradiance is averaged over a long time period compared to the temporal pulse widths of the pulses (e.g., averaged over a fraction of a second longer than the temporal pulse width, over 1 second, or over multiple seconds). For a continuous-wave (CW) light beam with time-varying irradiance, the time-averaged irradiance can be an average of the instantaneous irradiance averaged over a time period longer than a characteristic time period of fluctuations of the light beam. In at least some embodiments, a duty cycle in a range between 1% and 80%, between 10% and 30%, or 20% can be used with a peak irradiance at the target tissue of 0.001 mW/cm$^2$ to 1 W/cm$^2$, 0.01 mW/cm$^2$ to 500 mW/cm$^2$, 10 mW/cm$^2$ to 100 mW/cm$^2$, or 25 mW/cm$^2$ to 125 mW/cm$^2$. For example, in at least some embodiments, a pulsed dosimetry having a 20% duty cycle and a 50 mW/cm$^2$ is used. In at least some embodiments, the pulsed light beam has an energy or fluence per pulse (e.g., peak irradiance multiplied by the temporal pulse width) at the emission surface of the light source between 0.001 μJ/cm$^2$ to 150 J/cm$^2$, between 0.01 μJ/cm$^2$ to 5 J/cm$^2$, between 0.1 μJ/cm$^2$ to 1 J/cm$^2$, between 0.01 mJ/cm$^2$ to 100 mJ/cm$^2$, between 100 mJ/cm$^2$ to 1 J/cm$^2$, or overlapping ranges thereof.

The cross-sectional area of the light beam of at least some embodiments (e.g., multimode beams) can be approximated using an approximation of the beam intensity distribution. For example, as described more fully below, measurements of the beam intensity distribution can be approximated by a Gaussian (1/e$^2$ measurements) or by a "top hat" distribution and a selected perimeter of the beam intensity distribution can be used to define a bound of the area of the light beam. In at least some embodiments, the irradiance at the emission surface is selected to provide the desired irradiances at the target tissue.

The irradiance of the light beam is preferably controllably variable so that the emitted light energy can be adjusted to provide a selected irradiance at the tissue being treated. In at least some embodiments, the light beam emitted from the emission surface is continuous with a total radiant power in a range of 4 Watts to 6 Watts. In at least some embodiments, the radiant power of the light beam is 5 Watts±20% (CW). In certain embodiments, the peak power for pulsed light is in a range of 10 Watts to 30 Watts (e.g., 20 Watts). In at least some embodiments, the peak power for pulsed light multiplied by the duty cycle of the pulsed light yields an average radiant power in a range of 4 Watts to 6 Watts (e.g., 5 Watts).

In at least some embodiments, the irradiance of the light beam is selected to provide a predetermined irradiance at the target tissue (e.g., at a depth of the retinal pigmented epithelial layer). The selection of the appropriate irradiance of the light beam emitted from the emission surface to use to achieve a desired target tissue irradiance preferably includes consideration of scattering by other intervening tissues. Further information regarding the scattering of light by tissue is provided by U.S. Pat. No. 7,303,578 and V. Tuchin in "Tissue Optics: Light Scattering Methods and Instruments for Medical Diagnosis," SPIE Press (2000), Bellingham, WA, pp. 3-11, which are incorporated herein by reference.

Phototherapy for the treatment of ocular conditions (e.g., glaucoma, AMD, diabetic retinopathy, retinitis pigmentosa, CRS, NAION, Leber's disease, ocular surgery, and uveitis) may depend, at least in part, on the irradiance or power density (i.e., power per unit area or number of photons per unit area per unit time) and energy density (i.e., energy per unit area or number of photons per unit area) of the light energy applied to tissue in determining the relative efficacy of phototherapy. This may be particularly applicable with respect to treating and saving surviving but endangered cells in a zone of danger surrounding the primary injury. In at least some embodiments, given a selected wavelength of light energy, it is the irradiance or the energy density of the light delivered to tissue (as opposed to the total power or total energy delivered to the tissue) that may determine the relative efficacy of phototherapy.

Without being bound by theory or by a specific mechanism, it is believed that light energy delivered within a certain range of irradiances and energy densities provides the desired biostimulative effect on the intracellular environment, such that proper function is returned to previously nonfunctioning or poorly functioning mitochondria in at-risk cells. The biostimulative effect may include interactions with targeted photoacceptors within the target tissue, some which facilitate production of ATP or controls, inhibits, prevents, minimizes, or reduces apoptosis of the injured cells which have experienced disease, ageing or decreased blood flow (e.g., due to the ischemia).

In at least some embodiments, delivering the cytoprotective amount of light energy includes selecting a surface irradiance of the light energy at the eyelid or corneal surface corresponding to the predetermined irradiance at the target area of the eye (e.g. retina). As described above, light propagating through tissue is scattered and absorbed by the tissue. Calculations of the irradiance to be applied to the eyelid or corneal surface so as to deliver a predetermined irradiance to the selected target area of the eye may take into account the attenuation of the light energy as it propagates through intervening tissue. Factors known to affect the attenuation of light propagating to the eye from the skin include, but are not limited to, skin thickness, subject's age and gender, and the location of the target area of the eye, particularly the depth of the area relative to the surface of the skin or cornea.

The irradiance selected to be applied to the target area of the subject's eye may depend on a number of factors, including, but not limited to, the wavelength of the applied light, heating considerations, and the subject's clinical condition, including the extent of the affected tissue area. The irradiance or power density of light energy to be delivered to the target area of the subject's eye may also be adjusted to be combined with any other therapeutic agent or agents, especially pharmaceutical neuroprotective agents, to achieve the desired biological effect. In such embodiments, the selected wavelengths and irradiance may also depend on the additional therapeutic agent or agents chosen.

Temporal Pulse Width, Temporal Pulse Shape, Duty Cycle, Repetition Rate, and Irradiance Per Pulse A generalized temporal profile of a pulsed light beam in accordance with at least some embodiments is described herein. The temporal profile includes multiple pulses ($P_1$, $P_2$, . . . , $P_i$), each pulse having a temporal pulse width during which the instantaneous intensity or irradiance $I(t)$ of the pulse is substantially non-zero. For example, for the pulsed light beam, pulse $P_1$ has a temporal pulse width from time $t=0$ to time $t=T_1$, pulse $P_2$ has a temporal pulse width from time $t=T_2$ to time $t=T_3$, and pulse $P_i$ has a temporal pulse width from time $t=T_i$ to time $t=T_{i+1}$. The temporal pulse width can also be referred to as the "pulse ON time." The pulses are temporally spaced from one another by periods of time during which the intensity or irradiance of the beam is substantially zero. For example, pulse $P_1$ is spaced in time from pulse $P_2$ by a time $t=T_2-T_1$. The time between pulses can also be referred to as the "pulse OFF time." In at least some embodiments, the pulse ON times of the pulses are substantially equal to one another, while in other embodiments, the pulse ON times differ from one another. In at least some embodiments, the pulse OFF times between the pulses are substantially equal to one another, while in other embodiments, the pulse OFF times between the pulses differ from one another. As used herein, the term "duty cycle" has its broadest reasonable interpretation, including but not limited to, the pulse ON time divided by the sum of the pulse ON time and the pulse OFF time. For a pulsed light beam, the duty cycle is less than one. The values of the duty cycle and the temporal pulse width fully define the repetition rate of the pulsed light beam.

Each of the pulses can have a temporal pulse shape which describes the instantaneous intensity or irradiance of the pulse $I(t)$ as a function of time. For example, the temporal pulse shapes of the pulsed light beam are irregular, and are not the same among the various pulses. In at least some embodiments, the temporal pulse shapes of the pulsed light beam are substantially the same among the various pulses. For example, the pulses can have a square temporal pulse shape, with each pulse having a substantially constant instantaneous irradiance over the pulse ON time. In at least some embodiments, the peak irradiances of the pulses differ from one another, while in other embodiments, the peak irradiances of the pulses are substantially equal to one another. Various other temporal pulse shapes (e.g., triangular, trapezoidal) are also compatible with at least some embodiments. In at least some embodiments, the rise time and the fall time can be expressed relative to a specified fraction of the peak irradiance of the pulse (e.g., time to rise/fall to 50% of the peak irradiance of the pulse).

In at least some embodiments, the peak irradiance of a pulse $P_i$ can be the maximum value of the instantaneous irradiance I(t) during the temporal pulse width of the pulse. In at least some embodiments, the instantaneous irradiance is changing during the temporal pulse width of the pulse, while in other embodiments, the instantaneous irradiance is substantially constant during the temporal pulse width of the pulse.

In at least some embodiments, pulse irradiance $I_{P_i}$ of a pulse $P_i$ can be the integral of the instantaneous irradiance I(t) of the pulse $P_i$ over the temporal pulse width of the pulse:

$$I_{P_i} = \int_{T_i}^{T_{i+1}} I(t) \cdot dt/(T_{i+1} - T_i).$$

In at least some embodiments, total irradiance $I_{TOTAL}$ can be the sum of the pulse irradiances of the pulses:

$$I_{TOTAL} = \sum_{i=0}^{N} I_{P_i}.$$

In at least some embodiments, time-averaged irradiance $I_{AVE}$ can be the integral of the instantaneous irradiance I(t) over a period of time T large compared to the temporal pulse widths of the pulses:

$$I_{AVE} = \int_{0}^{T} I(t) \cdot dt/T.$$

The Integral $$\int_{0}^{T} I(t) \cdot dt$$

provides the energy of the pulsed light beam.

For example, for a plurality of square pulses with different pulse irradiances $I_{P_j}$ and different temporal pulse widths $\Delta T_j$, the time-averaged irradiance over a time T equals $$I_{AVE} = \frac{1}{T} \sum_{i} I_{P_i} \cdot \Delta T_i.$$

For another example, for a plurality of square pulses with equal pulse irradiances $I_P$, with equal temporal pulse widths, and equal pulse OFF times (having a duty cycle D), the time-averaged irradiance equals $I_{AVE}=I_P \cdot D$.

The pulse irradiances and the duty cycle can be selected to provide a predetermined time-averaged irradiance. In at least some embodiments in which the time-averaged irradiance is equal to the irradiance of a continuous-wave (CW) light beam, the pulsed light beam and the CW light beam have the same number of photons or flux as one another. For example, a pulsed light beam with a pulse irradiance of 5 mW/cm² and a duty cycle of 20% provides the same number of photons as a CW light beam having an irradiance of 1 mW/cm². However, in contrast to a CW light beam, the parameters of the pulsed light beam can be selected to deliver the photons in a manner which achieve results which are not obtainable using CW light beams.

In at least some embodiments, one or more of the temporal pulse width, temporal pulse shape, duty cycle, repetition rate, and pulse irradiance of the pulsed light beam are selected such that no portion of tissue is heated to a temperature greater than 60 degrees Celsius, greater than 55 degrees Celsius, greater than 50 degrees Celsius, or greater than 45 degrees Celsius. In at least some embodiments, one or more of the temporal pulse width, temporal pulse shape, duty cycle, repetition rate, and pulse irradiance of the pulsed light beam are selected such that no portion of tissue is heated to a temperature greater than 30 degrees Celsius above its baseline temperature, greater than 20 degrees Celsius above its baseline temperature, or greater than 10 degrees Celsius above its baseline temperature. In at least some embodiments, one or more of the temporal pulse width, temporal pulse shape, duty cycle, repetition rate, and pulse irradiance of the pulsed light beam are selected such that no portion of the tissue is heated to a temperature greater than 5 degrees Celsius above its baseline temperature, greater than 3 degrees Celsius above its baseline temperature, or greater than 1 degree Celsius above its baseline temperature. In at least some embodiments, the baseline temperature is the temperature at which the tissue would have if it were not irradiated by the light. In contrast to previous low-light level therapies, the pulsed light beam has an average radiant power in the range of 1 Watt to 10 Watts or in a range of 4 Watts to 6 Watts.

In at least some embodiments, pulsed irradiation may provide a more efficacious treatment. The pulsed irradiation can provide higher peak irradiances for shorter times, thereby providing more power to propagate to the target tissue while allowing thermal relaxation of the intervening tissue and blood between pulses to avoid unduly heating the intervening tissue. The time scale for the thermal relaxation is typically in the range of a few milliseconds. For example, the thermal relaxation time constant (e.g., the time for tissue to cool from an elevated temperature to one-half the elevated temperature) of human skin is about 3-10 milliseconds, while the thermal relaxation time constant of human hair follicles is about 40-100 milliseconds.

However, while pulsed light of this time scale advantageously reduces the heating of intervening tissue and blood, it does not provide an optimum amount of efficaciousness as compared to other time scales. In at least some embodiments, the subject's eye or ocular tissue is irradiated with pulsed light having parameters which are not optimized to reduce thermal effects, but instead are selected to stimulate, to excite, to induce, or to otherwise support one or more intercellular or intracellular biological processes which are involved in the survival, regeneration, or restoration of performance or viability of cells.

Thus, in at least some embodiments, the selected temporal profile can result in temperatures of the irradiated tissue which are higher than those resulting from other temporal profiles, but which are more efficacious than these other temporal profiles. In at least some embodiments, the pulsing parameters are selected to utilize the kinetics of the biological processes rather than optimizing the thermal relaxation of the tissue. In at least some embodiments, the pulsed light beam has a temporal profile (e.g., peak irradiance per pulse, a temporal pulse width, and a pulse duty cycle) selected to modulate membrane potentials in order to enhance, restore, or promote cell survival, cell function, or both of the irradiated cells following the ocular disease or injury.

For example, in at least some embodiments, the pulsed light has a temporal profile which supports one or more intercellular or intracellular biological processes involved in the survival or regeneration of retinal cells, but does not optimize the thermal relaxation of the irradiated tissue. In at least some embodiments, the cells survive longer after the irradiation as compared to their survival if the irradiation did not occur. For example, the light of at least some embodiments can have a protective effect on the cells, or can cause a regeneration process in the cells.

In at least some embodiments, the temporal profile (e.g., peak irradiance, temporal pulse width, and duty cycle) is selected to utilize the kinetics of the biological processes while maintaining the irradiated portion of the tissue at or below a predetermined temperature. This predetermined temperature is higher than the temperature which could be achieved for other temporal profiles (e.g., other values of the peak irradiance, temporal pulse width, and duty cycle) which limit or minimize the temperature increase of surrounding tissue due to the irradiation.

For example, a temporal profile having a peak irradiance of 10 W/cm$^2$ and a duty cycle of 20% has a time-averaged irradiance of 2 W/cm$^2$. Such a pulsed light beam provides the same number of photons to the irradiated surface as does a continuous-wave (CW) light beam with an irradiance of 2 W/cm$^2$. However, because of the "dark time" between pulses, the pulsed light beam can result in a lower temperature increase than does the CW light beam.

To reduce or minimize the temperature increase of the irradiated portion of the tissue, the temporal pulse width and the duty cycle can be selected to allow a significant portion of the heat generated per pulse to dissipate before the next pulse reaches the irradiated portion. In at least some embodiments, rather than optimizing the beam temporal parameters to minimize the temperature increase, the temporal parameters are selected to effectively correspond to or to be sufficiently close to the timing of the biomolecular processes involved in the absorption of the photons to provide an increased efficacy. Rather than having a temporal pulse width on the order of hundreds of microseconds, at least some embodiments utilize a temporal pulse width, which does not optimize the thermal relaxation of the irradiated tissue (e.g., milliseconds, tens of milliseconds, hundreds of milliseconds). Since these pulse widths are significantly longer than the thermal relaxation time scale, the resulting temperature increases are larger than those of smaller pulse widths, but still less than that of CW light beams due to the heat dissipation the time between the pulses.

A number of studies have investigated the effects of in vitro irradiation of cells using pulsed light on various aspects of the cells. A study of the action mechanisms of incoherent pulsed radiation at a wavelength of 820 nanometers (pulse repetition frequency of 10 Hz, pulse width of 20 milliseconds, dark period between pulses of 80 milliseconds, and duty factor (pulse duration to pulse period ratio) of 20%) on in vitro cellular adhesion has found that pulsed infrared radiation at 820 nanometers increases the cell-matrix attachment. (Karu, *Lasers in Surgery and Medicine* 29:274-281 (2001) which is incorporated in its entirety by reference herein.) It was hypothesized in this study that the modulation of the monovalent ion fluxes through the plasma membrane, and not the release of arachidonic acid, is involved in the cellular signaling pathways activated by irradiation at 820 nanometers. A study of light-induced changes to the membrane conductance of ventral photoreceptor cells found behavior which was dependent on the pulse parameters, indicative of two light-induced membrane processes. Lisman et al., *J. Gen. Physiology* 58:544-561 (1971), which is incorporated in its entirety by reference herein. Studies of laser-activated electron injection into oxidized cytochrome c oxidase which establishes the reaction sequence of the proton pump mechanism and some of its thermodynamic properties have time constants on the order of a few milliseconds. Belevich et al., *Proc. Nat'l Acad. Sci. USA* 104:2685-2690 (2007) and Belevich et al., *Nature* 440:829-832 (2006), each of which is incorporated in its entirety by reference herein. An in vivo study of neural activation based on pulsed infrared light proposed a photothermal effect from transient tissue temperature changes resulting in direct or indirect activation of transmembrane ion channels causing propagation of the action potential. Wells et al., *Proc. SPIE* 6084:60840X (2006), which is incorporated in its entirety by reference herein.

In at least some embodiments, the temporal profile of the pulsed light beam has a peak irradiance, a temporal pulse width, a temporal pulse shape, a duty cycle, and a pulse repetition rate or frequency. In at least some embodiments in which the pulsed light beam is transmitted through a region of the eye, at least one of the peak irradiance, temporal pulse width, temporal pulse shape, duty cycle, and pulse repetition rate or frequency is selected to provide a time-averaged irradiance (averaged over a time period including a plurality of pulses) at the emission surface of the light source between 0.01 mW/cm$^2$ to 1 W/cm$^2$, between 10 mW/cm$^2$ to 10 W/cm$^2$, between 100 mW/cm$^2$ to 1000 mW/cm$^2$, between 500 mW/cm$^2$ to 1 W/cm$^2$, or between 650 mW/cm$^2$ to 750 mW/cm$^2$ across the cross-sectional area of the light beam. In at least some embodiments, the time-averaged irradiance at the retinal tissue being treated is greater than 0.01 mW/cm$^2$.

In at least some embodiments, the temporal pulse shape is generally rectangular, generally triangular, or any other shape. In at least some embodiments, the pulses have a rise time (e.g., from 10% of the peak irradiance to 90% of the peak irradiance) less than 1% of the pulse ON time, or a fall time (e.g., from 90% of the peak irradiance to 10% of the peak irradiance) less than 1% of the pulse ON time.

In at least some embodiments, the pulses have a temporal pulse width (e.g., pulse ON time) in a range between 0.001 millisecond and 150 seconds, between 0.01 millisecond and 10 seconds, between 0.1 millisecond and 1 second, between 0.5 millisecond and 100 milliseconds, between 2 milliseconds and 20 milliseconds, or between 1 millisecond and 10 milliseconds. In at least some embodiments, the pulse width is 0.5, 1, 2, 4, 6, 8, 10, 15, 20, 30, 40, 50, 60, 70, 80, 90, 100, 120, 140, 160, 180, 200, 220, 240, 260, 280, or 300 milliseconds. In at least some embodiments, the temporal pulse width is in a range between 0.1 milliseconds and 150 seconds.

In at least some embodiments, the time between pulses (e.g., pulse OFF time) is in a range between 0.01 millisecond and 150 seconds, between 0.1 millisecond and 100 milliseconds, between 4 milliseconds and 1 second, between 8 milliseconds and 500 milliseconds, between 8 milliseconds and 80 milliseconds, or between 10 milliseconds and 200 milliseconds. In at least some embodiments, the time between pulses is 4, 8, 10, 20, 50, 100, 200, 500, 700, or 1000 milliseconds.

In at least some embodiments, the pulse duty cycle is in a range between 1% and 80% or in a range between 10% and 30%. In at least some embodiments, the pulse duty cycle is 10%, 20%, 30%, 40%, 50%, 60%, 70%, 80%, or 90%.

In at least some embodiments, the peak irradiance per pulse, or pulse energy density, across the cross-sectional area of the light beam at the emission surface of the light source is in a range between 0.01 mW/cm$^2$ to 1 W/cm$^2$, between 10 mW/cm$^2$ to 10 W/cm$^2$, between 100 mW/cm$^2$ to 1000 mW/cm$^2$, between 500 mW/cm$^2$ to 1 W/cm$^2$, between 650 mW/cm$^2$ to 750 mW/cm$^2$, between 20 mW/cm$^2$ to 20 W/cm$^2$, between 200 mW/cm$^2$ to 2000 mW/cm$^2$, between 1 W/cm$^2$ to 2 W/cm$^2$, between 1300 mW/cm$^2$ to 1500 mW/cm$^2$, between 1 W/cm$^2$ to 1000 W/cm$^2$, between 10 W/cm$^2$ to 100 W/cm$^2$, between 50 W/cm$^2$ to 100 W/cm$^2$, or between 65 W/cm$^2$ to 75 W/cm$^2$.

In at least some embodiments, the pulse energy density, or energy density per pulse, can be calculated as the time-averaged power density divided by pulse repetition rate, or frequency. For example, the smallest pulse energy density will happen at the smallest average power density and fastest pulse repetition rate, where the pulse repetition rate is duty cycle divided by the temporal pulse width, and the largest pulse energy density will happen at the largest average power density and slowest pulse repetition rate. For example, at a time-averaged power density of 0.01 mW/cm$^2$ and a frequency of 100 kHz, the pulse energy density is 0.1 nJ/cm$^2$ and at a time-averaged power density of 10 W/cm$^2$ and a frequency of 1 Hz, the pulse energy density is 10 J/cm$^2$. As another example, at a time-averaged power density of 10 mW/cm$^2$ and a frequency of 10 kHz, the pulse energy density is 1 µJ/cm$^2$ As yet another example, at a time-averaged power density of 700 mW/cm$^2$ and a frequency of 100 Hz, the pulse energy density is 7 mJ/cm$^2$.

Beam Size and Beam Profile

In at least some embodiments, the light beam emitted from the light source has a nominal diameter in a range of 10 millimeters to 40 millimeters, in a range of 20 millimeters to 35 millimeters, or equal to 30 millimeters. In at least some embodiments, the cross-sectional area is generally circular with a radius in a range of 1 centimeter to 2 centimeters. In at least some embodiments, the light beam emitted from the emission surface has a cross-sectional area greater than 2 cm$^2$ or in a range of 2 cm$^2$ to 20 cm$^2$ at the emission surface of the light source.

Eyebox or Eyepiece

The beam diameter can be defined as the largest chord of the perimeter of the area of the eye irradiated by the light beam at an intensity of at least 1/e$^2$ of the maximum intensity of the light beam. In at least some embodiments, the perimeter of the light beam used to determine the diameter of the beam can be defined to be those points at which the intensity of the light beam is 1/e$^2$ of the maximum intensity of the light beam. In at least some embodiments, the maximum-useful diameter is limited by the size of the subject's orbital area and by the heating of the subject's orbital area by the irradiation. In at least some embodiments, the minimum-useful diameter is limited by heating and by the total number of treatment sites that could be practically implemented. For example, to cover the subject's eye with a beam having a small beam diameter would correspondingly use a large number of treatment sites. In at least some embodiments, the time of irradiation per treatment site can be adjusted accordingly to achieve a desired exposure dose.

Specifying the total flux inside a circular aperture with a specified radius centered on the exit aperture ("encircled energy") is a method of specifying the power (irradiance) distribution over the light beam emitted from the emission surface. The "encircled energy" can be used to ensure that the light beam is not too concentrated, too large, or too small. In at least some embodiments, the light beam emitted from the emission surface has a total radiant power, and the light beam has a total flux inside a 20-millimeter diameter cross-sectional circle centered on the light beam at the emission surface which is no more than 75% of the total radiant power. In at least some embodiments, the light beam has a total flux inside a 26-millimeter diameter cross-sectional circle centered on the light beam at the emission surface, which is no less than 50% of the total radiant power.

In at least some embodiments, the beam intensity profile has a semi-Gaussian profile, while in at least some embodiments, the beam intensity profile has a "top hat" profile. In at least some embodiments, the light beam is substantially without high flux regions or "hot spots" in the beam intensity profile in which the local flux, averaged over a 3 millimeter by 3 millimeter area, is more than 10% larger than the average flux. In at least some embodiments, the device advantageously generate a light beam substantially without hot spots, thereby avoiding large temperature gradients, which would otherwise cause discomfort to the subject.

Divergence

In at least some embodiments, the beam divergence emitted from the emission surface is significantly less than the scattering angle of light inside the body tissue being irradiated, which is typically several degrees. In at least some embodiments, the light beam has a divergence angle greater than zero and less than 35 degrees.

Total Treatment Time

The total treatment time can be controlled by the programmable controller. The real time clock and the timers of the programmable controller can be used to control the timing of a particular therapeutic regimen and to allow for scheduled treatment (such as daily, twice a day, or every other day). In at least some embodiments, the treatment proceeds continuously for a period of 10 seconds to 2 hours, for a period of 1 to 20 minutes, or for a period of 1 to 5 minutes. For example, the total treatment time in at least some embodiments is two minutes. In at least some embodiments, the light energy is delivered for at least one total treatment period of at least five minutes per eye, or for at least one total treatment period of at least ten minutes for both eyes.

The minimum treatment time of at least some embodiments is limited by the biological response time (which is on the order of microseconds). The maximum treatment time of at least some embodiments can be limited by heating and by practical treatment times (e.g., completing treatment within about 24 hours of injury). The light energy can be pulsed during the treatment period or the light energy can be continuously applied during the treatment period. If the light is pulsed, the pulses can be 2 milliseconds long and occur at a frequency of 100 Hz or at least 10 nanoseconds long and occur at a frequency of up to 100 kHz, although shorter or longer pulse widths or lower or higher frequencies can be used. For example, the light can be pulsed at a frequency of 1 Hz to 100 Hz, from 100 Hz to 1 kHz, from 1 kHz to 100 kHz, less than 1 Hz, or greater than 100 kHz.

In at least some embodiments, the treatment may be terminated after one treatment period, while in other embodiments, the treatment may be repeated for at multiple treatment periods. The time between subsequent treatment periods can be at least five minutes, at least two in a 24-hour period, at least 1 to 2 days, or at least one week. The treatment can be repeated multiple times per day or multiple times per week. The length of treatment time and frequency of treatment periods can depend on several factors, including the functional recovery of the subject and the results of imaging analysis of the injury, the disease or condition being treated, the use of pulsed or continuous light, the irradiance of the light, the number of light sources used, or the sequence or pattern of the treatment. In at least some embodiments, the timing parameters can be adjusted in response to a feedback signal from a sensor or other device (e.g., biomedical sensor, magnetic resonance imaging device) monitoring the subject.

Transmission in Human Eye

In at least some embodiments, fluences of red or NIR as low as 3 to 5 J/cm$^2$ will be beneficial in vivo, but a large dose like 50 to 100 J/cm$^2$ may lose the beneficial effect.

The explanations and illustrations presented herein are intended to acquaint others skilled in the art with the present disclosure, its principles, and its practical application. Those skilled in the art may adapt and apply the present disclosure in its numerous forms, as may be best suited to the requirements of a particular use. Accordingly, the specific embodiments of the present present disclosure as set forth are not intended as being exhaustive or limiting of the present disclosure.

While the present disclosure has been discussed in the context of certain embodiments and examples, it should be appreciated that the present present disclosure extends beyond the specifically disclosed embodiments to other alternative embodiments or uses of the present disclosures and obvious modifications and equivalents thereof. Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, or rearranged. Additionally, the skilled artisan will recognize that any of the above-described methods can be carried out using any appropriate apparatus. Further, the disclosure herein of any particular feature, aspect, method, property, characteristic, quality, attribute, element, or the like in connection with various embodiments can be used in all other embodiments set forth herein. Additionally, processing steps may be added, removed, or reordered. A wide variety of designs and approaches are possible.

For purposes of this disclosure, certain aspects, advantages, and novel features of the present disclosure are described herein. It is to be understood that not necessarily all such advantages may be achieved in accordance with any particular embodiment of the present disclosure. Thus, for example, those skilled in the art will recognize that the present disclosure may be embodied or carried out in a manner that achieves one advantage or group of advantages as taught herein without necessarily achieving other advantages as may be taught or suggested herein.

Multi-Wavelength Phototherapy Systems and Methods

As described in further detail herein, it was discovered as part of the present disclosure that the coordinated and targeted delivery to a cell or tissue of light having two or more specified and distinct wavelengths (or ranges of wavelengths) can be advantageously employed: (a) to improve intracellular mitochondrial function via increased cytochrome C oxidase ("CCO") activity, (b) to restore an intracellular mitochondrial membrane potential ("MMP"), and (c) to up-regulate intracellular ATP synthesis. Moreover, such enhanced intracellular activities may be further exploited to promote a localized cellular response including, e.g., a cellular response that is absent from or present at an insufficient level in a damaged and/or diseased tissue as compared to a corresponding normal, undamaged, and/or healthy tissue.

Thus, within certain embodiments, the present disclosure provides multi-wavelength phototherapy systems and methods for promoting a desired cellular response, which methods include the coordinated and targeted delivery to a cell of two or more doses of light, wherein a first dose of light has a first wavelength or range of wavelengths that can stimulate a first intracellular activity and a second dose of light has a second wavelength or range of wavelengths that can stimulate a second intracellular activity, wherein the coordinated and targeted delivery of the first and second doses of light promotes the desired cellular response.

Within related embodiments, the present disclosure provides multi-wavelength phototherapy systems and methods for the treatment of damaged and/or diseased tissue, which methods include the coordinated and targeted delivery to a damaged and/or diseased tissue of two or more doses of light wherein a first dose of light has a first wavelength or range of wavelengths that can stimulate a first intracellular activity and a second dose of light has a second wavelength or range of wavelengths that can stimulate a second intracellular activity, wherein the coordinated and targeted delivery of the first and second doses of light can promote a desired cellular response within the damaged and/or diseased tissue thereby promoting the healing of the damaged tissue and/or reversing or slowing the progression of disease in the diseased tissue.

Within certain aspects of these embodiments, the present disclosure is exemplified by multi-wavelength phototherapy systems and methods for the treatment of damaged and/or diseased ocular tissue, which methods include the coordinated and targeted delivery to damaged and/or diseased ocular tissue within an eye of two or more doses of light, wherein a first dose of light has a first wavelength or range of wavelengths that can stimulate a first intracellular activity within the damaged and/or diseased ocular tissue, wherein a second dose of light has a second wavelength or range of wavelengths that can stimulate a second intracellular activity within the damaged and/or diseased ocular tissue, and wherein the coordinated and targeted delivery of the first and second doses of light can promote a desired cellular response within the damaged and/or diseased ocular tissue thereby promoting the healing of the damaged ocular tissue and/or reversing or slowing the progression of disease in the diseased ocular tissue.

Figure 24:
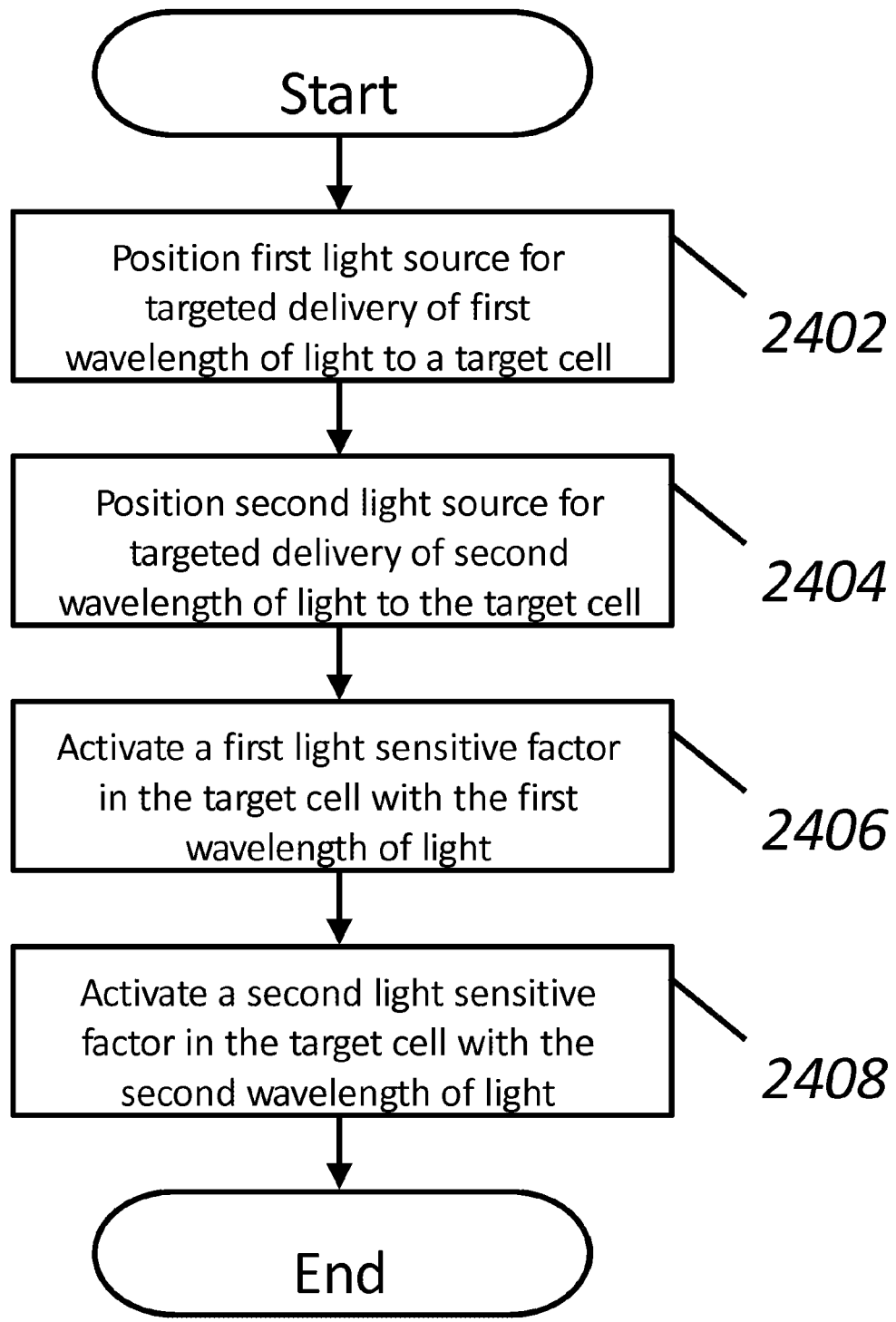
FIG. 24 is a schematic flowchart of one embodiment of a multi-wavelength phototherapy system and method for improving or restoring a functionality of a target cell, through the coordinated and targeted delivery to a cell of two or more distinct wavelengths of light to stimulate the activity of two or more light sensitive factors thereby improving or restoring target cell functionality.

FIG. 24 illustrates one embodiment of a multi-wavelength phototherapy system and method for improving or restoring a functionality of a target cell or tissue through the coordinated and targeted delivery to a cell or tissue of two or more distinct wavelengths of light to stimulate the activity of two or more light sensitive factors thereby improving or restoring target cell functionality. By these systems and methods, a first light source is positioned for targeted delivery of a first wavelength of light to a target cell 2402; a second light source is positioned for targeted delivery of a second wavelength of light to the target cell 2404; a first light sensitive factor in the target cell is activated with the first wavelength of light 2406; and a second light sensitive factor is activated in the target cell with the second wavelength of light 2408.

Figure 25:
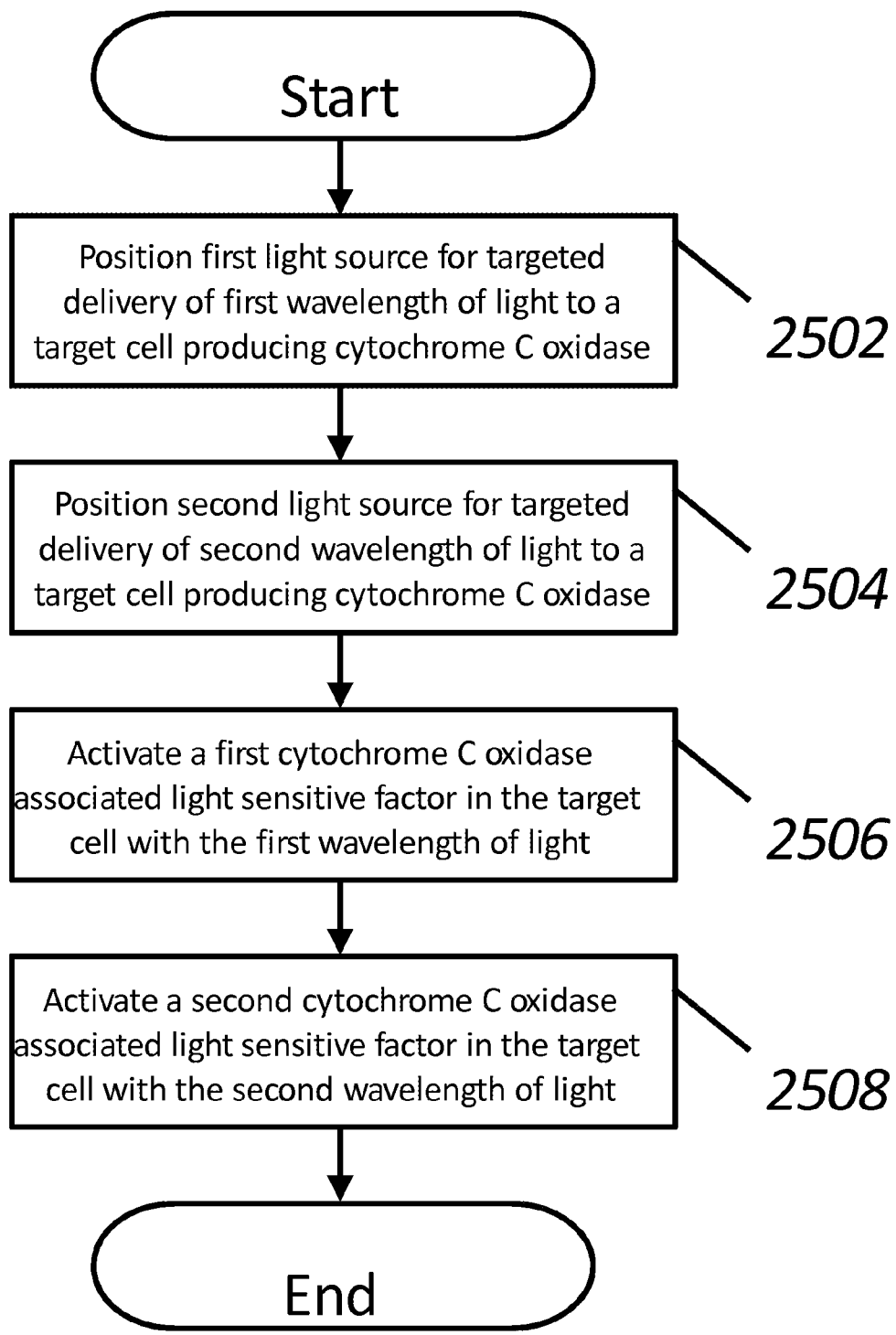
FIG. 25 is a schematic flowchart of one embodiment of a multi-wavelength phototherapy system and method for stimulating cytochrome c oxidase (CCO) activity in a cell through the coordinated and targeted delivery of two or more doses of light to a cell having two or more light sensitive factors that are associated with, and necessary for, CCO activity, wherein a first light dose has a first wavelength that can activate a first light sensitive factor in CCO and a second light dose has a second wavelength that can activate a second light sensitive factor in CCO thereby stimulating CCO activity.

FIG. 25 illustrates one embodiment of a multi-wavelength phototherapy system and method for stimulating cytochrome c oxidase (CCO) activity in a cell through the coordinated and targeted delivery of two or more doses of light to a cell having two or more light sensitive factors that are associated with, and necessary for, CCO activity, wherein a first light dose has a first wavelength that can activate a first light sensitive factor in CCO and a second light dose has a second wavelength that can activate a second light sensitive factor in CCO thereby stimulating CCO activity. By these systems and methods, a first light source is positioned for targeted delivery of a first wavelength of light to a target cell that is producing cytochrome C oxidase 2502; a second light source is positioned for targeted delivery of a second wavelength of light to the target cell that is producing cytochrome C oxidase 2504; a first cytochrome C oxidase associated light sensitive factor in the target cell is activated with the first wavelength of light 2506; and a second cytochrome C oxidase associated light sensitive factor is activated in the target cell with the second wavelength of light 2508.

Figure 26:
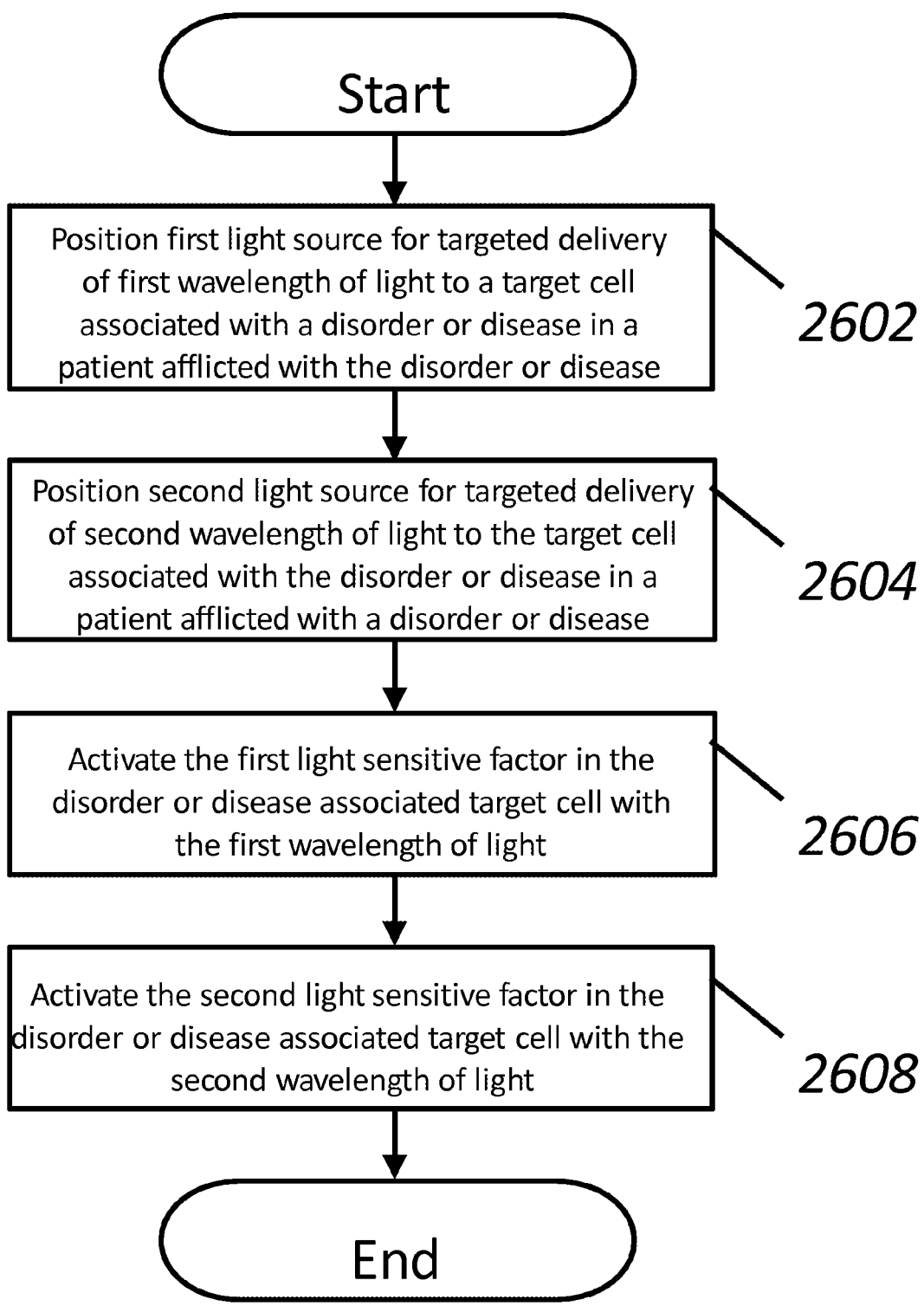
FIG. 26 is a schematic flowchart of one embodiment of a multi-wavelength phototherapy system and method for the treatment of a patient afflicted with a disorder or disease that is associated with one or more absent or diminished cellular functionality through the coordinated and targeted delivery of two or more distinct wavelengths of light to one or more cells in the patient to restore the absent cellular functionality or enhance the diminished cellular functionality thereby treating the disorder or disease.

FIG. 26 illustrates one embodiment of a multi-wavelength phototherapy system and method for the treatment of a patient afflicted with a disorder or disease that is associated with one or more absent or diminished cellular functionality through the coordinated and targeted delivery of two or more distinct wavelengths of light to one or more cells in the patient to restore the absent cellular functionality or enhance the diminished cellular functionality thereby treating the disorder or disease. By these systems and methods, a first light source is positioned for targeted delivery of a first wavelength of light to a target cell that is associated with a disorder or disease in a patient afflicted with the disorder or disease 2602; a second light source is positioned for targeted delivery of a second wavelength of light to the target cell that is associated with a disorder or disease in a patient afflicted with the disorder or disease 2604; a first light sensitive factor in the disorder or disease associated target cell is activated with the first wavelength of light 2606; and a second light sensitive factor in the disorder or disease associated cell is activated with the second wavelength of light 2608.

Figure 27:
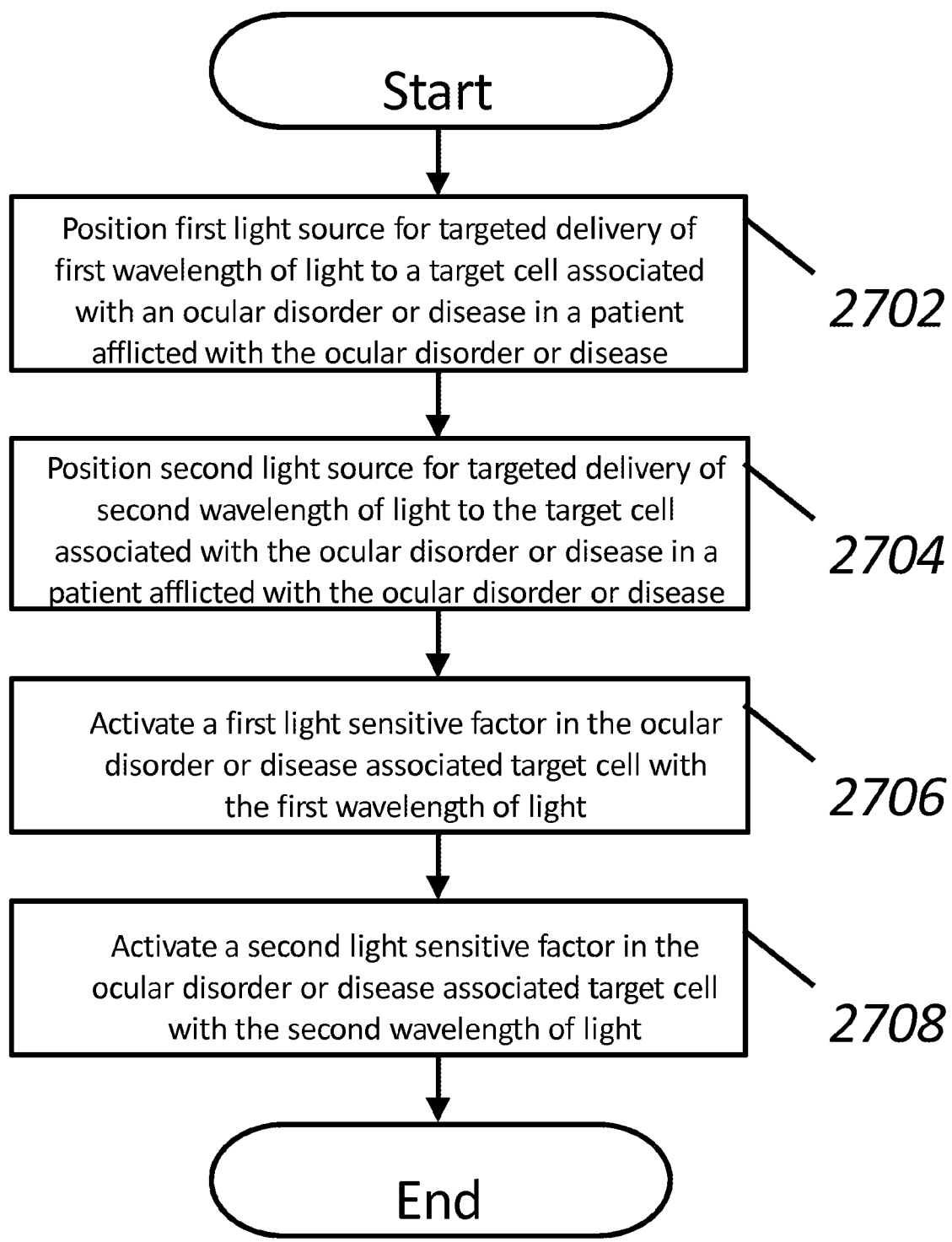
FIG. 27 is a schematic flowchart of one embodiment of a multi-wavelength phototherapy system and method for the treatment of a patient afflicted with an ocular disorder or disease that is associated with one or more absent or diminished functionality in an ocular cell, the systems and methods including the coordinated and targeted delivery of two or more distinct wavelengths of light to an eye in the patient to restore and or enhance the absent or diminished functionality to the ocular cell thereby treating the ocular disorder or disease.

FIG. 27 illustrates one embodiment of a multi-wavelength phototherapy system and method for the treatment of a patient afflicted with an ocular disorder or disease that is associated with one or more absent or diminished functionality in an ocular cell, the systems and methods including the coordinated and targeted delivery of two or more distinct wavelengths of light to an eye in the patient to restore and or enhance the absent or diminished functionality to the ocular cell thereby treating the ocular disorder or disease. By these systems and methods, a first light source is positioned for targeted delivery of a first wavelength of light to a target cell that is associated with an ocular disorder or disease in a patient afflicted with the ocular disorder or disease 2702; a second light source is positioned for targeted delivery of a second wavelength of light to the target cell that is associated with the ocular disorder or disease in a patient afflicted with the ocular disorder or disease 2704; a first light sensitive factor in the ocular disorder or disease associated target cell is activated with the first wavelength of light 2706; and a second light sensitive factor in the ocular disorder or disease associated cell is activated with the second wavelength of light 2708.

Multi-wavelength phototherapy systems and methods for the treatment of damaged and/or diseased ocular tissue are exemplified herein by multi-wavelength phototherapy systems and methods for the treatment of an ocular disorder and/or an ocular disease, treatments restore and/or enhance one or more symptom of an ocular disorder and/or disease including glaucoma, age-related macular degeneration, diabetic retinopathy, retinitis pigmentosa, CRS, NAION, Leber's disease, ocular damage resulting from a surgical procedure, and/or uveitis.

In certain aspects of these embodiments, light may be delivered through a closed eyelid, in which much of the light can be expected to scatter over a relatively broad area of the retina, or it may be administered to the open eye. In the case of the open eye, the majority of the therapeutic light can be delivered to the retina through the lens and pupil of the eye with minimal scattering. This can be accomplished, for example, through a Spatial Light Modulator (SLM) that precisely shapes and controls the exposed area on the retina. The SLM may be an LCOS panel, scanning mirror, deformable mirror array, or other modulation device.

1. Light Parameters for Achieving Therapeutic Efficacy

The various parameters of a light beam that is emitted from a light source can be advantageously selected to provide therapeutic benefit while controlling, inhibiting, preventing, minimizing, or reducing injury and/or discomfort to a patient, which can result from the light-induced heating of a target tissue, such as skin or eye tissue. These various parameters can be selected by those having skill in the art and can be combined within the range of values that are disclosed herein to achieve suitable conditions for the treatment of tissue damage or disease in accordance with the present systems and methods.

These light beam parameters can include, but are not limited to: (1) the wavelength of each of the two or more sources of light, (2) the irradiance or power density of each of the two or more sources of light, (3) the temporal pulse width and shape, duty cycle, repetition rate, and irradiance per pulse for each of the two or more sources of light, and (4) the total treatment time with each of the two or more sources of light. Following is a description of each of these parameters and guidance on the selection of those parameters for use in the multi-wavelength systems and methods disclosed herein.

a. Wavelengths or Ranges of Wavelengths

In certain embodiments, light in the visible to near-infrared wavelength range can be delivered to a target cell or tissue, such as a patient's skin or eye tissue. The light can be substantially monochromatic (i.e., having a single wavelength or a narrow band of wavelengths) wherein the desired cellular response can be established with the use of two or more selected wavelengths of light.

For example, one source of light can have a wavelength of from about 550 nanometers to about 1064 nanometers or from about 590 nanometers to about 980 nanometers. A plurality of wavelengths of light can be employed wherein a first wavelength of light is delivered concurrently with a second wavelength of light or wherein a first wavelength of light is delivered independently from and sequentially to a second wavelength of light.

In certain aspects of the present phototherapy systems and methods, the light can have a wavelength distribution that exhibits a peak wavelength wherein the wavelength distribution has a line width of less than ±10 nanometers from the peak wavelength, or less than ±4 nanometers from the peak wavelength, full width at 90% of energy. In related aspects, each wavelength of light can be selected independently from 590 nm±10%, 670 nm±10%, 810 nm±10%, and 1064 nm±10%, with a spectral line width of less than 4 nanometers, full width at 90% of energy. In further aspects, each wavelength of light can be selected independently from a wavelength distribution peaked at a peak wavelength and having a line width of less than ±40 nanometers from the peak wavelength at 50% of energy. In yet other aspects, each wavelength of light can be selected independently from 590 nm±10%, 670 nm±10%, 810 nm±10%, and 1064 nm±10%, with a spectral line width of less than 40 nanometers, full width at 50% of energy.

To ensure that the amount of light transmitted to the treated cell or tissue is maximized, each preselected wavelength of light can be selected to be at or near a transmission peak (or at or near an absorption minimum) for the intervening tissue. For example, a first wavelength can correspond to a peak in the transmission spectrum of tissue at about 820 nanometers (NIR) and a second wavelength can correspond to a peak in the transmission spectrum of tissue at about 670 nanometers (red visible).

The present phototherapy systems and methods can be performed with a light source having one or more continuously-emitting GaAlAs laser diodes each having a wavelength as described herein. Alternatively, the present methods can be performed with a light source having one or more LED(s), each of which providing non-coherent light having a wavelength as described herein.

Each of the two or more wavelengths of light can be selected to stimulate or activate one or more photoacceptors within a target cell or tissue. Without being bound by theory or specific mechanism of action, it is believed that delivery of light to one or more CCO photoacceptors, for example, will increase the production of ATP in the target cell or tissue to, thereby, control, inhibit, prevent, minimize, or reduce apoptosis of a damaged tissue, thus producing a beneficial therapeutic effect as described in detail herein. Wavelengths may also be chosen to activate one or more photoacceptors to control, inhibit, or stimulate distinct biological responses in a target cell or tissue.

Some photoacceptors, such as water or hemoglobin, are ubiquitous and absorb light to such a degree that light energy cannot reach a target tissue. It is known, for example, that water absorbs light at wavelengths above approximately 1300 nanometers. Thus, light at those wavelengths cannot penetrate effectively a target tissue due to the water content. Water is, however, transparent or nearly transparent to light at wavelengths of from about 300 nanometers to about 1300 nanometers. Similarly, hemoglobin, which absorbs light from about 300 nanometers to about 670 nanometers, is reasonably transparent to light above about 670 nanometers. Based upon these known factors that restrict the effective delivery of light, an "IR window" can be defined for the penetration of light that is delivered to a target tissue. Within this IR window, certain wavelengths of light can penetrate with less restriction by light absorbing molecules such as, for example, water and hemoglobin.

b. Irradiances and Power Densities

Within certain aspects of the present phototherapy systems and methods, light sources may be employed that emit a light beam having a time-averaged irradiance, or power density, at the emission surface of the light sources (e.g., at the tissue surface, such as a retinal surface) of from about 0.005 mW/cm$^2$ to about 10 W/cm$^2$, or from about 0.01 mW/cm$^2$ to about 5 W/cm$^2$, of from about 0.01 mW/cm$^2$ to about 1 W/cm$^2$, or from about 1 mW/cm$^2$ to about 500 mW/cm$^2$, or from about 500 mW/cm$^2$ to about 1 W/cm$^2$ across the cross-sectional area of the light beam.

Within other aspects of the present phototherapy systems and methods, light sources may be employed that emit a light beam having a time-averaged irradiance, or power density, that can be reduced generally by a factor of 1/e from the values that would be used if the light sources were applied to a closed eyelid versus directly to the retina. For example, the time-averaged irradiance at the target tissue (e.g., at a depth of approximately two centimeters below the eyelid) can be from about 0.001 mW/cm$^2$ to about 1 W/cm$^2$ at the level of the tissue or at least about 0.001, 0.005, 0.01, 0.05, 0.1, 0.5, 1, 5, 10, 15, 20, 30, 40, 50, 60, 70, 80, 90, 100, 200, 300, 400, 500, 600, 700, 800, 900, or 1000 mW/cm$^2$, or greater at the level of the tissue depending upon the desired therapeutic application.

For a pulsed light beam, the time-averaged irradiance can be averaged over a long time period as compared to a temporal pulse width of the pulses (e.g., averaged over a fraction of a second longer than the temporal pulse width, over 1 second, or over multiple seconds). For a continuous-wave (CW) light beam with time-varying irradiance, the time-averaged irradiance can be an average of the instantaneous irradiance averaged over a time period longer than a characteristic time period of fluctuations of the light beam.

In certain aspects of the present phototherapy systems and methods, a duty cycle can be from about 1% to about 80%, or from about 10% to about 30%, or about 20% with a peak irradiance at the target tissue of from about 0.001 mW/cm$^2$ to about 1 W/cm$^2$, about 0.01 mW/cm$^2$ to about 500 mW/cm$^2$, about 10 mW/cm$^2$ to about 100 mW/cm$^2$, or about 25 mW/cm$^2$ to about 125 mW/cm$^2$. For example, a pulsed dosimetry having a 20% duty cycle, a peak irradiance at the target tissue of about 50 mW/cm$^2$ can be used. In certain embodiments, the pulsed light beam has an energy or fluence per pulse (e.g., peak irradiance multiplied by the temporal pulse width) at the emission surface of the light source of from about 0.001 µJ/cm$^2$ to about 150 J/cm$^2$, or from about 0.01 µJ/cm$^2$ to about 5 J/cm$^2$, or from about 0.1 µJ/cm$^2$ to about 1 J/cm$^2$, or from about 0.01 mJ/cm$^2$ to about 100 mJ/cm$^2$, or from about 100 mJ/cm$^2$ to about 1 J/cm$^2$.

The cross-sectional area of a light beam (e.g., a multi-mode beam) can be determined by using an approximation of beam intensity distribution. For example, the beam intensity distribution can be approximated by a Gaussian ($1/e^2$ measurements) or "top hat" distribution and a selected perimeter of beam intensity distribution can be used to define a boundary for the area of a light beam.

The irradiance at an emission surface can be selected to provide the desired irradiances at the target tissue. The irradiance of a light beam can be variably controlled so that the emitted light energy can be adjusted to provide a selected irradiance at the target tissue. The light beam emitted from the emission surface can be continuous, with a total radiant power of from about 4 Watts to about 6 Watts. For example, the radiant power of a light beam can be 5 Watts±20% (CW).

The peak power for pulsed light can be from about 10 Watts to about 30 Watts, such as about 20 Watts. The peak power for pulsed light multiplied by the duty cycle of the pulsed light yields an average radiant power of from about 4 Watts to about 6 Watts, such as about 5 Watts.

The irradiance of a light beam can be selected to provide a predetermined irradiance at a target tissue (e.g., at a depth of the retinal pigmented epithelial layer). The selection of an appropriate irradiance of a light beam emitted from an emission surface to achieve a desired target tissue irradiance generally takes into consideration light scattering caused by non-target intervening tissues. Further information regarding the scattering of light by tissue is provided by U.S. Pat. No. 7,303,578 and Tuchin, *SPIE Press* 3-11 (2000), each of which is incorporated in its entirety by reference herein.

Phototherapy for the treatment of ocular conditions (e.g., glaucoma, AMD, diabetic retinopathy, retinitis pigmentosa, CRS, NAION, Leber's disease, ocular surgery, and uveitis) is based in part on the presently disclosed discovery that irradiance or power density (i.e., power per unit area or number of photons per unit area per unit time) and energy density (i.e., energy per unit area or number of photons per unit area) of light energy applied to a target tissue substantially influence the efficacy of given phototherapy regimen. These factors are particularly relevant when designing phototherapy regimen for preserving the efficacy of surviving, but endangered, cells within a "zone of danger" that is in the region surrounding a site of primary injury.

It was further discovered, and is presented herein as part of the present disclosure, that for a given wavelength of light energy, the irradiance and/or energy density of the light delivered to a target tissue—as opposed to the total power or total energy delivered to that tissue—that is determinative of the relative therapeutic efficacy of a given phototherapy regimen.

Without being bound by theory or by any specific mechanism of action, it is believed that the light energy that is delivered within a certain range of irradiances and energy densities provides a photobiomodulatory effect on an intracellular environment, such that one or more normal mitochondrial functionality is restored in a previously non- or poorly-functioning mitochondrion, such as a mitochondrion in an at-risk cell. Such a photobiomodulatory effect may include, for example, one or more interactions with one or more photoacceptors within a target tissue, which facilitates the production of ATP and/or controls, inhibits, prevents, minimizes, or reduces apoptosis in a diseased or ageing cell or increases blood flow in an ischemic tissue or modulates release of NO, ROS or other intracellular mediators to modify gene and protein expression in the at-risk cell. The role of irradiance and exposure times is discussed, for example, in Hans et al., *Lasers in Surgery and Medicine* 12:528-537 (1992), which is incorporated in its entirety by reference herein.

The delivery of a cytoprotective amount of light energy can also include the selection of a surface irradiance of light energy at a tissue surface, such as the surface of an eyelid or cornea, which surface irradiance corresponds to a predetermined irradiance at a target area of the tissue (e.g., the cornea or retina of an eye). As discussed in further detail herein, light propagating through a tissue can be both scattered and absorbed by that tissue. Calculations of the irradiance to be applied to a tissue surface, such as an eyelid or corneal surface, may, therefore, take into account the attenuation of light energy as it propagates through one or more intervening, non-target tissue, to ensure that a predetermined and intended irradiance is delivered to a selected area of a target tissue, such as an ocular tissue. Factors that affect the degree of attenuation of light propagating through the skin to a tissue can include, for example, the skin thickness, the patient's age and/or gender, and the location of the target area of the tissue, particularly the depth of the target area relative to the surface of the skin or, in the case of an eye, the cornea.

Factors influencing the selection of an irradiance for delivery to a target area of a given tissue include the wavelength of the light to be applied, considerations of light-induced heating of a tissue, and a patient's clinical condition and area of the damaged and/or diseased tissue. The irradiance or power density of light energy to be delivered to a tissue target area may also be influenced by, and adjusted accordingly, if the desired phototherapy regimen is delivered in combination and/or in conjunction with one or more additional therapeutic agents such as, for example, one or more neuroprotective agents, to achieve a desired biological effect. It will be understood that the selection of light parameters such as wavelength and irradiance will be influence by the specific therapeutic agents chosen.

c. Temporal Pulse Widths and Shapes, Duty Cycles, Repetition Rates, and Irradiances Per Pulse The systems and methods of the present disclosure further contemplate various temporal profiles of pulsed light beams that may be advantageously employed to enhance the therapeutic efficacy of a given phototherapy regimen. A temporal profile includes a plurality of pulses ($P_1, P_2, \ldots, P_i$), wherein each pulse exhibits a temporal pulse width during which time period an instantaneous pulse intensity or irradiance $I(t)$ is substantially non-zero. For example, for a pulsed light beam, pulse $P_1$ has a temporal pulse width (a/k/a "pulse ON time") from time $t=0$ to time $t=T_1$, pulse $P_2$ has a temporal pulse width from time $t=T_2$ to time $t=T_3$, and pulse $P_i$ has a temporal pulse width from time $t=T_i$ to time $t=T_{i+1}$. Pulses are temporally spaced from one another by periods of time during which the intensity or irradiance of a beam is substantially zero. For example, pulse $P_1$ is spaced in time from pulse $P_2$ by a time $t=T_2-T_1$ (a/k/a "pulse OFF time"). Pulse ON and pulse OFF times can be substantially equal to one another or can differ from one another.

As used herein, the term "duty cycle" refers, generally, to a pulse ON time divided by the sum of a pulse ON and a pulse OFF. Thus, a pulsed light beam has a duty cycle of less than one. A duty cycle and a temporal pulse width, together, fully define a repetition rate of a given pulsed light beam.

A pulse can have a temporal pulse shape that describes the instantaneous intensity or irradiance of the pulse $I(t)$ as a function of time. For example, the temporal pulse shape of a pulsed light beam can be irregular and need not be the same among various pulses or the temporal pulse shape of a pulsed light beam can be substantially the same among various pulses. For example, a pulse can have a square temporal pulse shape with a substantially constant instantaneous irradiance over a pulse ON time. Peak irradiances of pulses can differ from one another or can be substantially equal to one another. Various other temporal pulse shapes (e.g., triangular and trapezoidal) are also contemplated for use in the presently disclosed systems and methods.

A rise time and a fall time can be expressed relative to a specified fraction of a peak irradiance of a pulse (e.g., time to rise/fall to 50% of the peak irradiance of a pulse). As used herein, the term "peak irradiance" of a pulse $P_i$ refers, generally, to the maximum value of an instantaneous irradiance $I(t)$ during a temporal pulse width of a pulse. The instantaneous irradiance can change or can remain substantially constant during a temporal pulse width of a pulse.

As used herein, the term "pulse irradiance" $I_{P_i}$ of a pulse $P_i$ refers, generally, to an integral of an instantaneous irradiance $I(t)$ of a pulse $P_i$ over a temporal pulse width of a pulse:

$$I_{P_i} = \int_{T_i}^{T_{i+1}} I(t) \cdot dt / (T_{i+1} - T_i)$$

As used herein, the term "total irradiance" $I_{TOTAL}$ refers, generally, to the sum of a pulse irradiance of pulses:

$$I_{TOTAL} = \sum_{i=0}^{N} I_{P_i}$$

As used herein, the term "time-averaged irradiance" $I_{AVE}$ refers, generally, to the integral of an instantaneous irradiance $I(t)$ over a period of time T that is large compared to a temporal pulse width of a pulse:

$$I_{AVE} = \int_0^T I(t) \cdot dt / T,$$

wherein the integral $$\int_0^T I(t) \cdot dt$$

represents the energy of a pulsed light beam.

For a plurality of square pulses with different pulse irradiances, $I_{P_i}$, and different temporal pulse widths, $\Delta T_i$, the time-averaged irradiance over time T is defined as follows:

$$I_{AVE} = \frac{1}{T} \sum_i I_{P_i} \cdot \Delta T_i$$

For a plurality or square pulses warn equal pulse irradiances $I_P$, equal temporal pulse widths, and equal pulse OFF times (having a duty cycle D), the time-averaged irradiance is defined as follows:

$$I_{AVE} = I_P \cdot D$$

Pulse irradiances and duty cycles can be selected to provide a predetermined time-averaged irradiance. In certain applications of the present systems and methods in which the time-averaged irradiance is equal to the irradiance of a continuous-wave (CW) light beam, the pulsed light beam and the CW light beam have equivalent photon and/or flux numbers. For example, a pulsed light beam having a pulse irradiance of 5 mW/cm$^2$ and a duty cycle of 20% provides the same number of photons as a CW light beam having an irradiance of 1 mW/cm$^2$. In contrast to a CW light beam, however, the parameters of a pulsed light beam can be selected such that photons are delivered in a manner that achieves an intracellular and/or therapeutic benefit that is not obtainable with a CW light beam.

One or more of a pulsed light beam's temporal pulse width, temporal pulse shape, duty cycle, repetition rate, and/or pulse irradiance can be independently selected such that no portion of a target tissue is heated to greater than about 60° C., of greater than about 55° C., or greater than about 50° C., or greater than about 45° C.

One or more of a pulsed light beam's temporal pulse width, temporal pulse shape, duty cycle, repetition rate, and pulse irradiance can be independently selected such that no portion of a target tissue is heated to greater than about 30° C. above its baseline temperature, or greater than about 20° C. above its baseline temperature, or greater than about 10° C. above its baseline temperature.

One or more of a pulsed light beam's temporal pulse width, temporal pulse shape, duty cycle, repetition rate, and pulse irradiance can be independently selected such that no portion of a target tissue is heated to greater than about 5° C. above its baseline temperature, or greater than about 3° C. above its baseline temperature, or greater than about 1° C. above its "baseline temperature," which, as used herein, refers, generally, to the temperature of a target tissue prior to irradiation by a light beam. Pulse light beams that may be suitably employed in the systems and methods disclosed herein can have an average radiant power of from about 1 Watt to about 10 Watts or from about 4 Watts to about 6 Watts.

Depending upon the precise phototherapy regimen contemplated, a pulsed irradiation may provide one or more enhancements to cellular functionality and/or therapeutic efficacy. Pulsed irradiation can, for example, provide higher peak irradiances for shorter times, thereby providing more power to deliver to a target tissue while allowing thermal relaxation of the intervening tissue and blood between pulses thereby reducing extent to which an intervening tissue is heated. The time scale for thermal relaxation is typically in the range of a few milliseconds. For example, a thermal relaxation time constant (e.g., the time for tissue to cool from an elevated temperature to one-half the difference between an elevated temperature and a baseline temperature) of human skin is from about 3 milliseconds to about 10 milliseconds, while the thermal relaxation time constant of a human hair follicles is from about 40 milliseconds to about 100 milliseconds. Thus, previous applications of pulsed light to the body for hair removal have optimized temporal pulse widths of greater than 40 milliseconds with time between pulses of hundreds of milliseconds.

While pulsed light within this time scale advantageously reduces the heating of intervening tissue and blood, it does not, however, exhibit optimal efficacy as compared to other time scales. A target tissue, such as an eye or ocular tissue, can be irradiated with pulsed light having parameters that are not optimized to reduce thermal effects but, instead, are optimized to stimulate, excite, induce, and/or otherwise support one or more intercellular or intracellular biological processes that enhance the survival, regeneration, performance, or viability of cells within the target tissue. Thus, the selected temporal profile can result in temperatures of the irradiated tissue that are higher than those resulting from other temporal profiles yet provide improved therapeutic efficacy as compared to those temporal profiles that maintain a target tissue temperature at or near its baseline temperature.

In other aspects of the present systems and methods, pulsing parameters can be selected to favor the kinetics of a biological processes rather than to optimize a tissue's thermal relaxation. The pulsed light beam can, for example, be selected that has a temporal profile (e.g., peak irradiance per pulse, a temporal pulse width, and a pulse duty cycle) that modulates a membrane potential thereby enhancing, restoring, and/or promoting one or more of survival and/or functionality of an irradiated cell, such as a cell that is associated with an ocular disorder, injury, and/or disease. In these aspects of the present systems and methods, a pulsed light can have a temporal profile that supports one or more intercellular or intracellular biological process that is involved in the survival or regeneration of a cell or tissue, such as a retinal cell or tissue, but is not optimized to achieve the thermal relaxation of the irradiated cell or tissue. In such aspects, the cell and/or tissue survives longer after irradiation as compared to a like cell and/or tissue without irradiation. For example, the light can have a protective effect and/or cause a regenerative process in a target cell or tissue.

A temporal profile (e.g., peak irradiance, temporal pulse width, and duty cycle) can be selected to favor the kinetics of a biological process while maintaining an irradiated cell or portion of a tissue at or below a predetermined temperature. This predetermined temperature can be higher than the optimized temperature that can be achieved with other temporal profiles (e.g., other values of the peak irradiance, temporal pulse width, and duty cycle) that minimize the temperature increase of a neighboring cell and/or surrounding tissue due to the irradiation.

A temporal profile having a peak irradiance of 10 W/cm² and a duty cycle of 20% has a time-averaged irradiance of 2 W/cm². Such a pulsed light beam provides the same number of photons to an irradiated surface as does a continuous-wave (CW) light beam having an irradiance of 2 W/cm². Because of the "dark time" between pulses, the pulsed light beam can, however, yield a lower temperature increase than a CW light beam providing the same number of photons to the irradiated surface.

To minimize the temperature increase of the irradiated portion of a tissue, a temporal pulse width and duty cycle can be selected to allow a significant portion of the heat generated per pulse to dissipate before the next pulse reaches the irradiated portion. Thus, rather than optimizing a light beam's temporal parameters to minimize a temperature increase in a target tissue, a temporal parameter can be selected to effectively correspond to and/or to be sufficiently aligned with the timing of a biomolecular processes that is involved in the absorption of a photon thereby increasing therapeutic efficacy. Rather than having a temporal pulse width on the order of hundreds of microseconds, a temporal pulse width can be employed that is not optimized for thermal relaxation of an irradiated tissue (e.g., milliseconds, tens of milliseconds, hundreds of milliseconds). Since such pulse widths are significantly longer than the thermal relaxation time scale, the resulting temperature increases are larger than those of smaller pulse widths but, because of the heat dissipation the time between the pulses, are less than temperature increases resulting from irradiation with a CW light beam.

Various effects of in vitro irradiation of cells using pulsed light have been described in the literature. Incoherent pulsed radiation at a wavelength of 820 nanometers (pulse repetition frequency of 10 Hz, pulse width of 20 milliseconds, dark period between pulses of 80 milliseconds, and duty factor (pulse duration to pulse period ratio) of 20%) on in vitro cellular adhesion has been shown to promote cell-matrix attachment. Karu et al., *Lasers in Surgery and Medicine* 29:274-281 (2001), which is incorporated in its entirety by reference herein. The modulation of monovalent ion fluxes through a plasma membrane, and not the release of arachidonic acid, was hypothesized to be involved in cellular signaling pathways activated by irradiation at 820 nanometers.

Light-induced changes to the membrane conductance of ventral photoreceptor cells has been found to be dependent upon pulse parameters suggest that two or more processes are involved in light-induced membrane functionalities. Lisman et al., *J. Gen. Physiology* 58:544-561 (1971), which is incorporated in its entirety by reference herein. Laser-activated electron injection into oxidized cytochrome c oxidase yielded kinetics that establish a reaction sequence of a proton pump mechanism and some of its thermodynamic properties exhibit time constants on the order of a few milliseconds. Belevich et al., *Proc. Nat'l Acad. Sci. U.S.A.* 104:2685-2690 (2007) and Belevich et al., *Nature* 440:829-832 (2006), each of which is incorporated in its entirety by reference herein. An in vivo study of neural activation based on pulsed infrared light proposed a photo-thermal effect from transient tissue temperature changes resulting in direct or indirect activation of transmembrane ion channels causing propagation of the action potential. Wells et al., *Proc. SPIE* 6084:60840X (2006), which is incorporated in its entirety by reference herein.

A temporal profile of a pulsed light beam can include a peak irradiance, a temporal pulse width, a temporal pulse shape, a duty cycle, and a pulse repetition rate or frequency. In those aspects of the presently disclosed systems and methods in which a pulsed light beam is transmitted through a region of a tissues, such as an ocular tissue, at least one of peak irradiance, temporal pulse width, temporal pulse shape, duty cycle, and/or pulse repetition rate or frequency can be selected to provide a time-averaged irradiance (averaged over a time period including a plurality of pulses) at the emission surface of the light source of from about 0.01 mW/cm² to about 1 W/cm², or from about 10 mW/cm² to about 10 W/cm², or from about 100 mW/cm² to about 1000 mW/cm², or from about 500 mW/cm² to about 1 W/cm², or from about 650 mW/cm² to about 750 mW/cm² across the cross-sectional area of the light beam. For example, in certain aspects of these systems and methods, the time-averaged irradiance at a tissue, such as a retinal tissue, is greater than 0.01 mW/cm².

A temporal pulse shape can be generally rectangular, generally triangular, or any one of a wide range of shapes. Pulses can have a rise time (e.g., from 10% of the peak irradiance to 90% of the peak irradiance) of less than 1% of a pulse ON time, or a fall time (e.g., from 90% of the peak irradiance to 10% of the peak irradiance) of less than 1% of a pulse ON time.

Pulses can have a temporal pulse width (e.g., pulse ON time) of from about 0.001 millisecond and about 150 seconds, or from about 0.1 milliseconds to about 150 seconds, or from about 0.01 millisecond to about 10 seconds, or from about 0.1 millisecond to about 1 second, or from about 0.5 millisecond to about 100 milliseconds, or from about 2 milliseconds to about 20 milliseconds, or from about 1 millisecond to about 10 milliseconds. For example, the pulse width can be about 0.5, 1, 2, 4, 6, 8, 10, 15, 20, 30, 40, 50, 60, 70, 80, 90, 100, 120, 140, 160, 180, 200, 220, 240, 260, 280, or 300 milliseconds.

A time between pulses (e.g., pulse OFF time) can be from about 0.01 millisecond to about 150 seconds, or from about 0.1 millisecond to about 100 seconds, or from about 4 milliseconds to about 1 second, or from about 8 milliseconds to about 500 milliseconds, or from about 8 milliseconds to about 80 milliseconds, or from about 10 milliseconds to about 200 milliseconds. For example, the time between pulses can be about 4, 8, 10, 20, 50, 100, 200, 500, 700, or 1000 milliseconds.

A pulse duty cycle can be from about 1% to about 80% or from about 10% to about 30%. For example, the pulse duty cycle can be about 10%, 20%, 30%, 40%, 50%, 60%, 70%, 80%, or 90%.

A peak irradiance per pulse, or pulse energy density, across a cross-sectional area of a light beam at an emission surface of a light source can be from about 0.01 mW/cm² to about 1 W/cm², or from about 10 mW/cm² to about 10 W/cm², or from about 100 mW/cm² to about 1000 mW/cm², or from about 500 mW/cm² to about 1 W/cm², or from about 650 mW/cm² to about 750 mW/cm², or from about 20 mW/cm² to about 20 W/cm², or from about 200 mW/cm² to about 2000 mW/cm², or from about 1 W/cm² to about 2 W/cm², or from about 1300 mW/cm² to about 1500 mW/cm², or from about 1 W/cm² to about 1000 W/cm², or from about 10 W/cm² to about 100 W/cm², or from about 50 W/cm² to about 100 W/cm², or from about 65 W/cm² to about 75 W/cm².

A pulse energy density, or energy density per pulse, can be calculated as the time-averaged power density divided by pulse repetition rate, or frequency. For example, the smallest pulse energy density will occur at the smallest average power density and fastest pulse repetition rate, where the pulse repetition rate is duty cycle divided by the temporal pulse width. The largest pulse energy density will occur at the largest average power density and slowest pulse repetition rate. For example, at a time-averaged power density of 0.01 mW/cm$^2$ and a frequency of 100 kHz, the pulse energy density is 0.1 nJ/cm$^2$ and at a time-averaged power density of 10 W/cm$^2$ and a frequency of 1 Hz, the pulse energy density is 10 J/cm$^2$. As another example, at a time-averaged power density of 10 mW/cm$^2$ and a frequency of 10 kHz, the pulse energy density is 1 µJ/cm$^2$. As yet another example, at a time-averaged power density of 700 mW/cm$^2$ and a frequency of 100 Hz, the pulse energy density is 7 mJ/cm$^2$.

2. Total Treatment Times

The multi-wavelength phototherapy systems and methods of the present disclosure further provide suitable total treatment times to achieve enhanced cellular functionality and/or improved therapeutic efficacy. A treatment regimen can, for example, proceed continuously for a period of from about 10 seconds to about 2 hours, or from about 1 minute to about 20 minutes, or from about 1 minute to about 5 minutes. For example, the total treatment time can be about two minutes.

In related aspects, the light energy can be delivered for at least one total treatment period of at least about five minutes or for at least one total treatment period of at least ten minutes. The minimum treatment time can be limited by the biological response time (which is on the order of microseconds). The maximum treatment time can be limited by heating and/or to practical treatment times (e.g., completing treatment within about 24 hours of injury).

Light energy can be pulsed during a treatment period or light energy can be continuously applied during the treatment period. If light energy is pulsed, the pulses can be 2 milliseconds long and can occur at a frequency of 100 Hz or can be at least about 10 nanoseconds long and can occur at a frequency of up to about 100 kHz, although shorter or longer pulse widths and/or lower or higher frequencies can be used. For example, the light can be pulsed at a frequency of from about 1 Hz to about 100 Hz, or from about 100 Hz to about 1 kHz, or from about 1 kHz to about 100 kHz, or less than 1 Hz, or greater than 100 kHz.

The treatment may be terminated after one treatment period or the treatment may be repeated for at multiple treatment periods. The time between subsequent treatment periods can be from about five minutes, at least two in a 24-hour period, at least about 1 to 2 days, or at least about one week. The treatment can be repeated multiple times per day and/or multiple times per week. The length of treatment time and frequency of treatment periods can depend on several factors, including the functional recovery of a cell, tissue, and/or patient; the results of imaging analysis of the damaged and/or injured tissue; the disease or condition being treated; the use of pulsed or continuous light; the irradiance of the light; the number of light sources used; and/or the sequence or pattern of the treatment.

Total treatment time can be controlled by the programmable controller. The real time clock and the timers of the programmable controller can be used to control the timing of a particular therapeutic regimen and to allow for scheduled treatment (such as daily, twice a day, or every other day). Timing parameters can be adjusted in response to a feedback signal from a sensor or other device (e.g., biomedical sensor, magnetic resonance imaging device) monitoring the subject.

3. Light Sources

The multi-wavelength phototherapy systems and methods of the present disclosure employ one or more light sources to achieve the delivery of two or more doses of light each dose having a distinct wavelength or range of wavelengths. Suitable light sources include, for example, the office-based, wearable, and/or implantable devices that are described in co-pending PCT Patent Application No. PCT/US15/49261; "MULTI-WAVELENGTH PHOTOTHERAPY DEVICES, SYSTEMS, AND METHODS FOR THE NON-INVASIVE TREATMENT OF DAMAGED OR DISEASED TISSUE"), which was filed on Sep. 9, 2015, and U.S. Provisional Patent Application Nos. 62/048,182; "DEVICES AND METHODS FOR NON-INVASIVE MULTI-WAVELENGTH LOW LEVEL LIGHT THERAPY FOR OCULAR TREATMENTS") and 62/048,187; "WEARABLE DEVICES AND METHODS FOR MULTI-WAVELENGTH LOW LEVEL LIGHT THERAPY FOR OCULAR TREATMENTS"), each of which was filed on Sep. 9, 2014. PCT Patent Application No. PCT/US15/49261 and U.S. Provisional Patent Application Nos. 62/048,182 and 62/048,187 are incorporated herein by reference in their entirety. Other suitable light sources that can be adapted for use in the presently disclosed multiwavelength phototherapy systems and methods include the Warp10™ (Quantum Devices, Inc.; Barneveld, WI) and the GentleWaves® (Light Bioscience LLC; Virginia Beach, VA) instruments. Such light sources can be configured to deliver to a target tissue, such as an ocular tissue, two or more doses of a therapeutically effective amount of low level light having a combination of two or more distinct wavelengths or rages of wavelength.

Such devices for independently delivering, in a targeted fashion, multi-wavelength combinations of low level light to damaged or diseased tissue can be used in combination with sensors and/or other imaging modalities to establish the optimal spatial and tissue parameters to provide an efficacious treatment to the target tissue.

Light sources can be used in the presently disclosed systems and methods in combination with one or more non-light energy sources, such as a magnetic energy source, a radio frequency source, a DC electric field source, an ultrasonic energy source, a microwave energy source, a mechanical energy source, an electromagnetic energy source, and the like.

For example, phototherapy can be combined with OCT, PET, MM, femtosensors, etc. to provide instruments having therapeutic, diagnostic, tracking, and/or enhanced targeting capabilities for the use of optimizing phototherapy. The light source can optionally include a lens, a diffuser, a waveguides, and/or other optical element or elements.

One or more light emitting diodes (LED) and/or one or more laser diodes can be used as light sources. Laser diodes can be gallium-aluminum-arsenic (GaAlAs) laser diodes, Aluminium gallium indium phosphide (AlGaInP) laser diodes, diode-pumped solid state (DPSS) lasers, and/or vertical cavity surface-emitting laser (VCSEL) diodes. In those applications of the present systems and methods in which multiple light sources are used, the light sources can be coupled to one or more optical fibers. Other light sources that generate or emit light with an appropriate wavelength and irradiance and/or a combination of multiple types of light sources can be used.

The irradiance of the light beam can be selected to provide a predetermined irradiance at a target tissue, such as an ocular tissue. The target tissue, such as an ocular tissue, may be affected by disease or damaged by trauma that has been identified using standard medical imaging techniques. The target tissue, such as an ocular tissue, may be a portion of a tissue that is known to be affected by a particular disease or disorder. For example, the target tissue may be from a portion of an eye that is known to control certain functions and/or processes.

The selection of an appropriate irradiance of a light beam emitted from an emission surface to achieve a desired irradiance at the level of a target tissue, such as an ocular tissue, can include the wavelength of light selected; the nature of the cell and/or tissue being treated; the type of disease, trauma, and/or disorder being treated; the clinical condition of the patient; and the distance between the light source and to the target cell and/or tissue region to be treated.

In some embodiments with a plurality of light sources, certain light sources emit light at a higher or lower power as compared to other light sources. Power output of the light source can thus be tailored depending on the thickness of an intervening tissue, such as an eyelid or cornea, that is between the emission surface of the light source and the target tissue.

PBM therapy (670 nm) has been implicated in changing the gene expression pattern for multiple genes involved in cellular metabolism (Masha, 2012). Up regulation of several genes involved in electron chain transport, energy metabolism and oxidative phosphorylation were seen, thus rejuvenating the cells metabolic capacity and stimulating the increase in ATP production, which drives other pleiotropic processes, all leading to long-term improvement or normalization of cellular functions. It has been established that phototherapy may affect NFU, a major cellular regulator of inflammatory pathways and gene expression. It is not obvious as to the combined benefits of photons from one or more wavelengths to target and regulate gene expression of specific pathways, but the current present disclosure teaches the use of gene expression mapping in multi-wavelength phototherapy to identify characteristics suitable for photobiomodulation applications, which are distinct from those of light used in other applications.

In another embodiment, the use of phototherapy in combination with gene therapy may provide a unique approach to stimulate, enhance or control the regulation and expression of novel genes incorporated into the nucleus through viral vectors or other gene therapy techniques. This is distinct from using light-activated gene products, but to utilize selected wavelengths to naturally stimulate cellular gene expression profiles for newly implanted gene therapy approaches. In a further embodiment, the use of gene therapy has been considered in the regeneration of retinal tissue or to provide for gene therapy in the mitochondrial ocular disorders, such at Leber's hereditary optic neuropathy or AMD. In those cases, gene therapy in combination with PBM to stimulate specific mitochondrial electron transport protein expression may be contemplated as a better or optimized therapeutic combination approach.

Separately, RNA and protein expression patterns are used by cells to effectively regulate numerous pathways and subsequent cellular activity. The use of multiple wavelengths of light would provide a unique approach to indirectly regulate and improve RNA and protein expression and restore cellular function in damage or diseased tissue. It is unknown as to the individual benefits of photons from one or more wavelengths to regulate protein expression of a specific pathway, but the current present disclosure teaches the use of protein mapping in combination with phototherapy to identify characteristics suitable for photobiomodulation applications, which are distinct from those of light used in other applications. AMD is considered a chronic inflammatory disease wherein protein deposits further propagate the inflammatory state and disease progression. Therefore, the use of multi-wavelength PBM would have the potential to deliver a unique combination therapeutic, where in the individual wavelengths do not provide for such a therapy. In RPE cell studies, the use of 590 nm light has been shown to inhibit VEGF expression and thus the use of 590 nm PBM would be useful in one aspect of the treatment of wet AMD subtype. VEGF antibody treatment (Lucentis®) is a currently approved pharmaceutical treatment for wet AMD. Separately, the use of 810 nm PBM has been shown to improve mitochondrial function, reduce inflammatory markers and prevent β-amyloid deposits in age-related Alzheimer's mice (De Taboada et al, 2011) and could be used in another aspect of the disease. Further, the use of 670 nm PBM has been shown to reduce inflammatory markers like complement C3 expression and deposition in AMD mouse models but does not affect-amyloid deposition. Both deposition of lipofusion and β-amyloid have been implicated in the etiology of the diseased eyes in AMD patients. The combinations of multi-wavelengths PBM alone or the use of multi-wavelengths with an anti-VEGF MoaB, (e.g., Lucentis®, Avastin®), an anti-amyloid drug (e.g., β-secretase inhibitors), an anti-inflammatory drug (e.g., non-steroidal, anti-inflammatory agents, anti-complement agent (e.g., Properidin, C3, MASP-2, C5 inhibitors), antioxidants or vitamin supplements (e.g., AREDS supplements (Lipotriad Visonary™, Viteyes 2®, ICaps®, and PreserVision®, contain similar constituents but either in different proportions, or with additional ingredients,) or visual cycle disruptor (e.g., isomerase inhibitors (ACU-4429). These examples provide unique PBM therapeutic combinations which could represent one or more wavelengths with a device or pharmaceutical or two or more wavelengths of light alone.

In another embodiment, the targeted use of phototherapy to improve mitochondrial function via increased CCO activity, restoration of MMP and regulation of ATP synthesis may be best achieved by the use of multiple wavelengths of light to create the appropriate local cellular response to damage or disease.

Localized cellular conditions in trauma and disease may differ across discrete tissue or organ areas and are under dynamic local regulation. For example, multi-wavelength phototherapy of local CCO activity can lead to release of inhibitory NO from the O2 binding site. NO is a powerful vasodilator and signal transducer that can regulate the local blood flow to targeted tissue. Thus, the presently disclosed methods may be used to reverse local ischemia or restricted blood flow to damaged or diseased tissue.

The multi-wavelength phototherapy systems and methods disclosed herein provide for the discrete targeting of phototherapy to tissues, such as a retina, and associated surrounding tissue types. As an example, the present multi-wavelength phototherapy systems and methods may be adapted for the treatment of discrete local optic nerve ischemia as seen in non-arteric ischemic optic neuropathy (NAION) or to target anatomical islands of cellular deposits that may be a nidus for inflammation, ischemia, or disease in dry AMD.

In early stage AMD, discrete cellular deposits of lipofuscin can be identified on the retina by standard imaging techniques (OCT, fluorescence imaging). In such a case, the present systems and methods may employ one or more imaging modalities, such as OCT or fluorescence, to facilitate the targeting of the multi-wavelength phototherapy to slow the disease, stop or reverse the deposition of proteins such as lipofuscin or β-amyloid, and/or to reduce, slow or stop the progression of the disease. These aspects of the presently disclosed targeted phototherapy systems and methods provide a disease-modifying approach to chronic ocular disease.

The present multi-wavelength phototherapy systems and methods can, therefore, be employed alone to deliver therapeutically-effective doses of light or may be used in further combination with OCT or other imaging devices (e.g., PET, MM, Ultra-sound, Doppler, Fluroescence, Femtosensors, etc.) to identify discrete areas of interest thereby facilitating the targeting of cell or tissue boundaries with a combination of wavelengths of light to, thereby, optimize or personalize patient treatment.

Imaging modalities, such as femtosensors, may also be used in combination with the present multi-wavelength phototherapy systems and methods to monitor local retinal O2 levels to identify AMD patients with local hypoxia to improve treatments and to monitor increased O2 levels to restore mitochondrial retinal function. It will be understood that the selection of wavelengths, doses, and other treatment parameters may vary depending upon the underlying disorder or disease. The coordinated targeting of multiple wavelengths of light permits the individualized treatment of a patient to restore cellular performance and slow or stop disease propagation. Thus, certain aspects of the present systems and methods can be done alone, in combination with one or more diagnostic devices, and/or with instruments that combine both phototherapy and diagnostic modalities.

In further aspects of the present systems and methods, the desired phototherapy regimen can include selecting appropriate wavelengths and dosing parameters to achieve a desired therapeutic benefit. It will be understood that distinct wavelengths of light exhibit tissue-specific absorption properties, which impact depth of light penetration and, therefore, influence the appropriate dose that is required to achieve therapeutic efficacy.

Additional instrument functionalities, such cameras or other sensors can be employed in the present systems and methods to capture patient-specific features, including orbital features, such as depth, size, skin color, and distances, which permits the dose for each wavelength to be established separately or in combination to optimize treatment parameters. Sensors may also be used to aid in dose selection through the open or closed eyelid, thereby accommodating variations in tissue color and thickness.

In certain systems and methods, including systems and methods for the treatment of a chronic disorder or disease, such as a chronic neurological or ocular condition, a patient may be required to undergo repeated, frequent (e.g., daily) doses of phototherapy. Thus, minimally-invasive phototherapy systems and methods may be employed. For example, in systems and methods for the treatment of intraocular pressure in patients with glaucoma, daily or constant monitoring and phototherapy treatments may be performed at regular intervals. In another example, patients suffering from optic nerve disorders may have limited capacity to institute treatment or may not be physically able to administer treatment. In such instances, minimally-invasive systems and methods of phototherapy may employ an indwelling apparatus, such as an LED.

In some instances, certain parameters of the delivered light may be employed to prevent the scattering by and/or heating of an intervening tissue that is between a light source and a target tissue to which light is delivered. Such parameters that may be varied include the wavelength and/or irradiance of the delivered light. In such instances, light may, for example, be delivered at a low, yet efficacious, irradiances of from about 100 µW/cm$^2$ to about 10 W/cm$^2$ at a target tissue site. The temporal profile of the delivered light, such as the temporal pulse width, temporal pulse shape, duty cycle, and/or pulse frequency as well as the time period over which the light is delivered can be limited to hundreds of microseconds to minutes thereby achieving an efficacious energy density at the target tissue site being treated.

The target area of a targeted tissue, such as, for example, an optic nerve and surrounding ocular tissue, can include an area of damage, which is referred to herein as a "zone of danger." The target area of a target tissue can also include a portion of a tissue, such as an ocular tissue, that is outside of a zone of danger. Biomedical mechanisms and reactions that are involved in phototherapy are described in Karu, *Proc. SPIE* 4159:1-17 (2000) and Hamblin et al., *Proc. SPIE* 6140:614001 (2006), each of which is incorporated in its entirety by reference herein.

The multi-wavelength phototherapy systems and methods disclosed herein may be employed for the treatment of physical trauma, such as, for example, injury resulting from cataract or lens surgery; for the treatment of inflammation or degeneration of a target tissue; to provide cytoprotection to slow or prevent the irreversible degeneration and loss of a target tissue, such as an ocular tissue, following a primary destructive event; to improve target tissue function, to prevent or slow the progression of loss of target tissue function, and/or to regain previously lost target tissue function; to promote the proliferation, migration, and regenerative cellular properties of endogenous progenitor stem cells for use in the treatment of disease.

In the case of ocular tissue, the term "ocular function" refers, generally, to both visual acuity and contrast sensitivity. Diseases or conditions affecting ocular function include, but are not limited to, primary destructive events include disease processes or physical injury or insult, such as age-related macular degeneration, glaucoma, stroke, diabetic retinopathy, retinitis pigmentosa, CRS, NAION, Leber's disease, ocular surgery, uveitis, cerebral ischemia including focal optic nerve ischemia, and physical trauma such as crush or compression injury to ocular tissues, including a crush or compression injury of the optic nerves or retina, or any acute injury or insult producing ocular degeneration.

As used herein, the terms "therapeutic regimen" and "treatment regimen" refer to a protocol and associated procedures used to provide a therapeutic treatment that includes one or more periods during which light is irradiated to one or more ocular target regions. As used herein, the terms "target," "target area," and "target region" refer to a particular ocular area, region, location, structure, population, or projection (e.g., within the retina or optic nerve) to be irradiated by light in association with the treatment of a particular type of ocular condition, disease, disorder, or injury. In certain embodiments, the irradiated portion of the eye can comprise the entire eye. In other embodiments, the irradiated portion of the eye can comprise a targeted region of the eye, such as the retinal region, the macula, or the cornea.

The present multi-wavelength phototherapy systems and methods can be advantageously employed to promote the proliferation, migration, and regenerative cellular properties of endogenous progenitor retinal stem cells for use in retinal or ocular diseases. Stem cells have the capacity to both self-renew and generate postmitotic cells. The retinal pigment epithelium (RPE) is a monolayer of cells underlying and supporting the neural retina. It begins as a plastic tissue, capable, in some species, of generating lens and retina, but differentiates early in development and remains normally nonproliferative throughout life. Subpopulations of adult human RPE cells can be activated in vitro to a self-renewing cell, the retinal pigment epithelial stem cell (RPESC) that loses RPE markers, proliferates extensively, and can redifferentiate into stable cobblestone RPE monolayers. RPESCs are multipotent and, under defined conditions, can generate both neural and mesenchymal progeny, which may be used in replacement therapies and disease modeling.

The present multi-wavelength phototherapy systems and methods can also be advantageously employed to promote the proliferation, migration, and regenerative cellular properties following implantation of retinal stem cells for the treatment of retinal or ocular diseases, such as retinal degenerative disease, which treatment regimen have, historically, been hampered by the limited ability of retinal stem cells to migrate and integrate into a host retina.

The present multi-wavelength phototherapy systems and methods can also be advantageously employed in in vitro methods for preparing cell lysates and membrane enriched and soluble cell fractions thereof, from mesenchymal stem cells and/or ectodermal stem cells.

4. Combination Therapies Including Multi-Wavelength Phototherapy

Within certain embodiments, the present disclosure provides multi-wavelength phototherapy systems and methods that further include the administration and/or delivery to a human patient of one or more small molecule pharmaceutical drug, biologic molecule, or other suitable device to optimize and personalize a given phototherapy treatment regimen for a target tissue, such as an ocular tissue. Within other embodiments, the presently disclosed multi-wavelength phototherapy systems and methods may further include diagnosis and/or monitoring of target tissue damage and/or disease.

The presently disclosed multi-wavelength phototherapy systems and methods can be adapted for the treatment of AMD, which is a chronic inflammatory disease characterized by the formation of protein deposits that propagate an inflammatory state and promote disease progression. Within certain aspects, such multi-wavelength phototherapy systems and methods for the treatment of AMD can include the delivery of a combination of light doses such as, for example, a 590 nm light dose to inhibit VEGF expression; a 810 nm light dose to improve mitochondrial function, reduce inflammatory markers, and to prevent β-amyloid deposits; and a 670 nm light dose to reduce the production and deposition of inflammatory markers such as complement C3, and lipofuscin.

These multi-wavelength phototherapy systems and methods can be used in further combination with one or more anti-VEGF antibodies (e.g., Lucentis®, Avastin®); one or more anti-inflammatory drugs (e.g., non-steroidal, anti-inflammatory agents); one or more anti-amyloid drug (e.g., β-secretase inhibitors); one or more anti-complement agents (e.g., Properidin, C3, MASP-2, C5 inhibitors); one or more antioxidants or vitamin supplements (e.g., AREDS supplements such as Lipotriad Visonary™, Viteyes 2®, ICaps®, and PreserVision®); and/or one or more visual cycle disruptors (e.g., isomerase inhibitors (ACU-4429)).

The present disclosure contemplates the use of phototherapy in combination with compositions and methods applicable to cell-based or regenerative therapy for retinal diseases and disorders. In particular, the present disclosure provides multi-wavelength phototherapy systems and methods that further comprise the administration of one or more compositions or devices or that are used in combination with one or more methods for the regeneration or repair of retinal tissue using stem cells (e.g., Very Small Embryonic-Like Stem cells (VSELs) mesenchymal stem cells, ectodermal stem cells, etc.). One aspect of the disclosure is a method for treating a retinal disorder with the present phototherapy systems and methods after administering to a patient in need thereof an ectodermal stem cell population to the patient's retinal tissue, and intravenously administering to the patient a mesenchymal stem cell population. The ectodermal stem cells may be derived from fetal neural tissue.

Another aspect of the present disclosure concerns deriving the mesenchymal stem cell population from a source selected from at least one of umbilical cord blood, adult bone marrow and placenta. In still another aspect of the disclosure, the retinal disorder is one or more but not limited to macular degeneration, retinitis pigmentosa, diabetic retinopathy, glaucoma or limbal epithelial cell deficiency.

In certain embodiments, the cells can be induced in vitro to differentiate into a neural or epithelial lineage cells prior to administration and preconditioned with phototherapy. In other embodiments, the cells are administered with at least one other agent, such as a drug for ocular therapy, or another beneficial adjunctive agent such as an anti-inflammatory agent, anti-apoptotic agents, antioxidants or growth factors. In these embodiments, phototherapy treatment can be administered simultaneously with, or before, or after, the postpartum cells. The use of phototherapy systems and methods may be used stimulate the regenerative aspects of the stem cells or use to supplement beneficial adjunctive therapeutic agents or both.

While various embodiments have been disclosed herein, other embodiments will be apparent to those skilled in the art. The various embodiments disclosed herein are for purposes of illustration and are not intended to be limiting, with the true scope and spirit being indicated by the claims.

EXAMPLES

Example 1

Treatment of Dry Age Related Macular Degeneration with Photobiomodulation

This Example demonstrates that photobiomodulation (PBM) can be employed advantageously in methods for improving the vision and contrast sensitivity of patients afflicted with dry age-related macular degeneration (AMD).

The study that is presented in this Example was designed as a prospective IRB-approved study in which low powered light at near infrared (NIR), far red and yellow wavelengths was applied, in serial consecutive treatments, to the eyes of patients with dry AMD. Included in this study were patients with dry AMD who were 50 years or older and having best corrected visual acuity (BCVA) ranging from 20/20 to 20/200. Primary outcome measures included: (i) visual acuity, (ii) contrast sensitivity, and (iii) fixation stability. Excluded from the study were subjects with previous or active wet AMD, with a previous history of epilepsy, with cognitive impairment, other retinal disease, previous retinal surgery, significant media opacity, or contraindications to dilation drops.

The absence of neovascularization was ascertained prior to enrollment by examination with Ocular Coherence Tomography (OCT) and Intravenous Fluorescein Angiography (IVFA) and confirmed by a retina specialist.

All subjects were assessed for Visual Acuity with ETDRS charts at 4 meter distance (Precision Vision, USA) recorded in log MAR units, contrast sensitivity at 1.5 and 3 cycles per degree (Stereo Vision Optec 6500, USA) recorded as log contrast sensitivity and for fixation stability with the Nidek MP1 micro perimeter (Nidek Technologies, Padova, Italy). Accurate estimates of fixation stability could be obtained from raw data by calculation of a bi-curve ellipse area (BCEA) as described in Tarita et al., *Retina* 28:125-133 (2008). Calculations were based on the minor and major axes of an ellipse area covering fixational eye movements and took into account two standard deviation measures of each recorded eye movement. The results were expressed in square degrees.

Measurements took place: (i) prior to treatment; (2) immediately following the treatment protocol; (3) at 6 weeks following the treatment protocol; (4) at 4 months following the treatment protocol; (5) at 6 months following the treatment protocol; and (6) at 12 months following the treatment protocol.

The intervention included the use of low level light therapy (PBM) in the yellow, far red and near infrared (NIR) range using low energy delivery with the Warp10 (Quantum Devices) and the Gentlewaves (Light Bioscience) instruments, which are commercially available and approved by the FDA and Health Canada for use in other conditions. The treatment parameters followed for the Warp10 delivery system were 670 nm f 15 nm at 50-80 mW/cm$^2$, 4-7.68 J/cm2, for 88±8 seconds. The treatment parameters followed for the Gentlewaves delivery system were 590 nm±8 nm at 4 mW/cm$^2$, and 790 nm±60 nm at 0.6 mW/cm$^2$, for 35 seconds, pulsed at 2.5 Hz (250 milliseconds on, 150 milliseconds off) while delivering 0.1 J/cm$^2$/treatment. All subjects were treated with the two devices used sequentially at each treatment visit for a total of 18 treatments over a six-week period (3 times per week for 6 weeks).

Data analysis was based on descriptive statistics that included frequency distributions, a measure of central tendency (mean), and a measure of dispersion (standard deviation). A statistical comparison of means between populations was made by t-test and repeated measures analysis of variance (repeated measures ANOVA). Differences were considered to be statistically significant at p values of less than 0.05. The study was performed in adherence to the guidelines of the Declaration of Helsinki. The study protocol was approved by an independent Research Ethics Committee (IRB Services, Aurora, Canada). Informed consent was obtained from all participants.

Over a span of 12 months, 18 AMD study eyes (6 males and 12 females) were recruited and treated; aged 61 to 90 years (mean 74.3 years/SD 7.7).

Repeated measures ANOVA for contrast sensitivity (3 cycles/degree) yielded F (4,68)=11.44 with a p-value of less than 0.0001 and repeated measures ANOVA for contrast sensitivity (1.5 cycles/degree) yielded F (4,68)=4.39 with a p-value of less than 0.0032. Average ETDRS BCVA for the AMD group was measured at 0.25 log Mar units before the treatment and at 0.13 log Mar units 12 months after the treatment (p<0.0001). Repeated Measures ANOVA yielded F(4,68)=18.86 with a p-value of less than 0.0001.

The photobiomodulation treatment regimen disclosed in this example revitalized, rejuvenated, and improved the function of compromised retinal cells on the border of the geographic atrophy with an immediate improvement in visual acuity for a period of 6 months or less.

Figure 16:
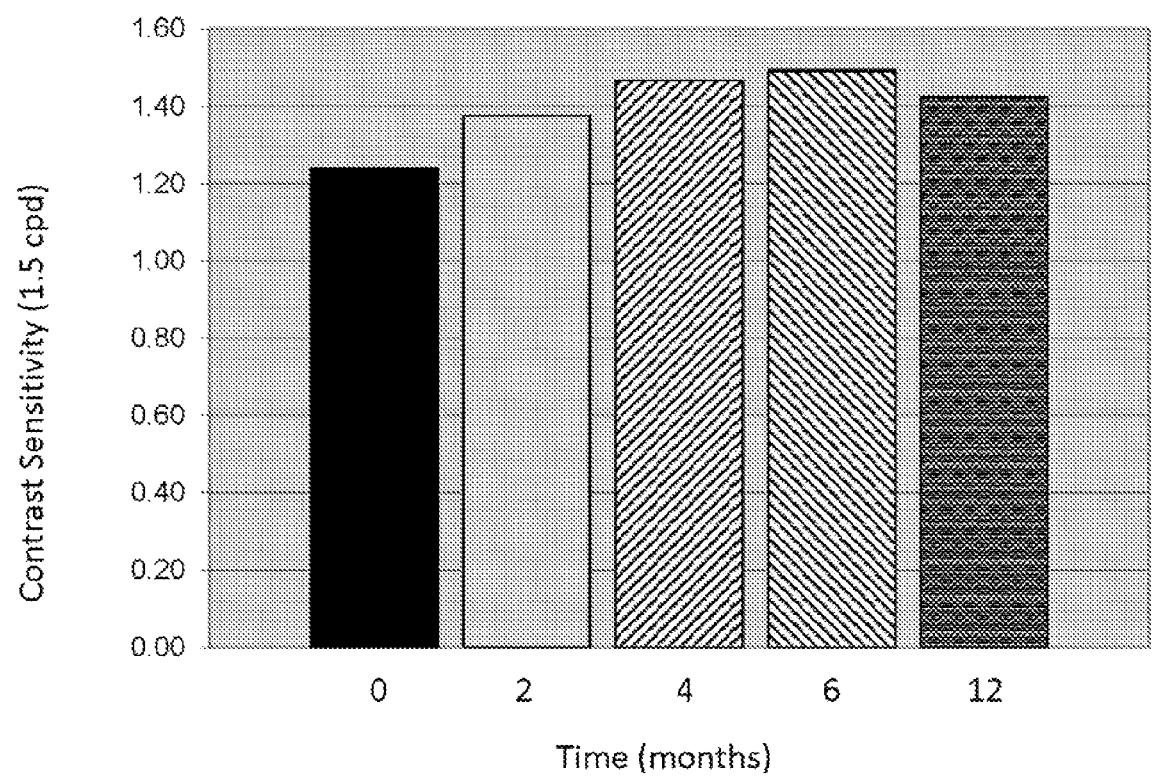
FIG. 16 is a bar graph of Contrast Sensitivity at 1.5 cycles per degree (cpd; in log units) prior to treatment (0) and at 2, 4, 6, and 12 months showing an average for all patients during a course of multi-wavelength photobiomodulation therapy according to the systems and methods of the present disclosure (described in Example 1). N=18. Repeated measures ANOVA for Contrast Sensitivity (1.5 cycles/degree): F (4,68)=4.39, p less than 0.0032. (i.e., statistically significant).
Figure 17:
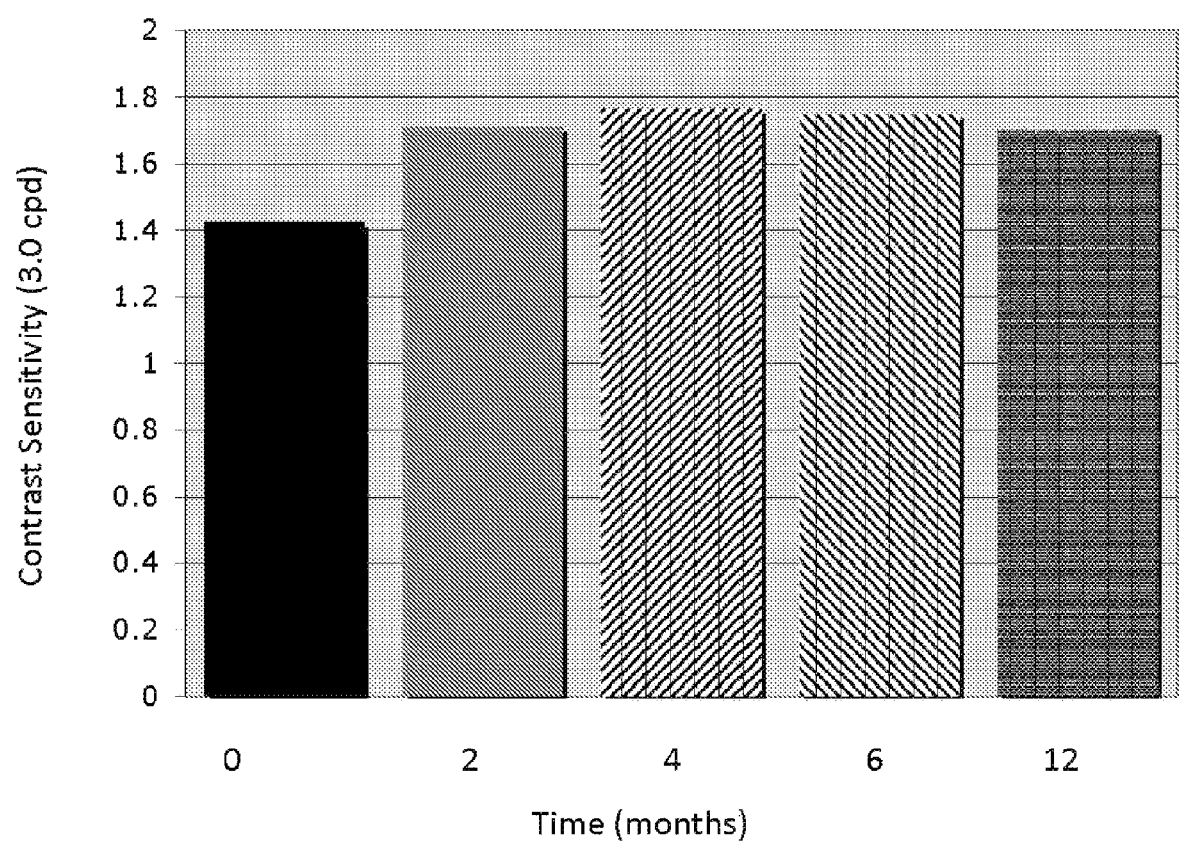
FIG. 17 is a bar graph of Contrast Sensitivity at 3 cpd (in log units), which shows an average contrast sensitivity score for all patients prior to treatment (0) and at 2, 4, 6, and 12 months post-treatment with a course of multi-wavelength photobiomodulation therapy according to the systems and methods of the present disclosure (described in Example 1). N=18. Repeated measures ANOVA for Contrast sensitivity (3 cycles/degree): F (4,68)=11.44, p less than 0.0001. (i.e., statistically significant).

Contrast sensitivity was statistically significantly improved with the presently-disclosed photobiomodulation treatment regimen. Improvement in contrast sensitivity remained at significant levels at 12 months (FIGS. 16-17).

Figure 18:
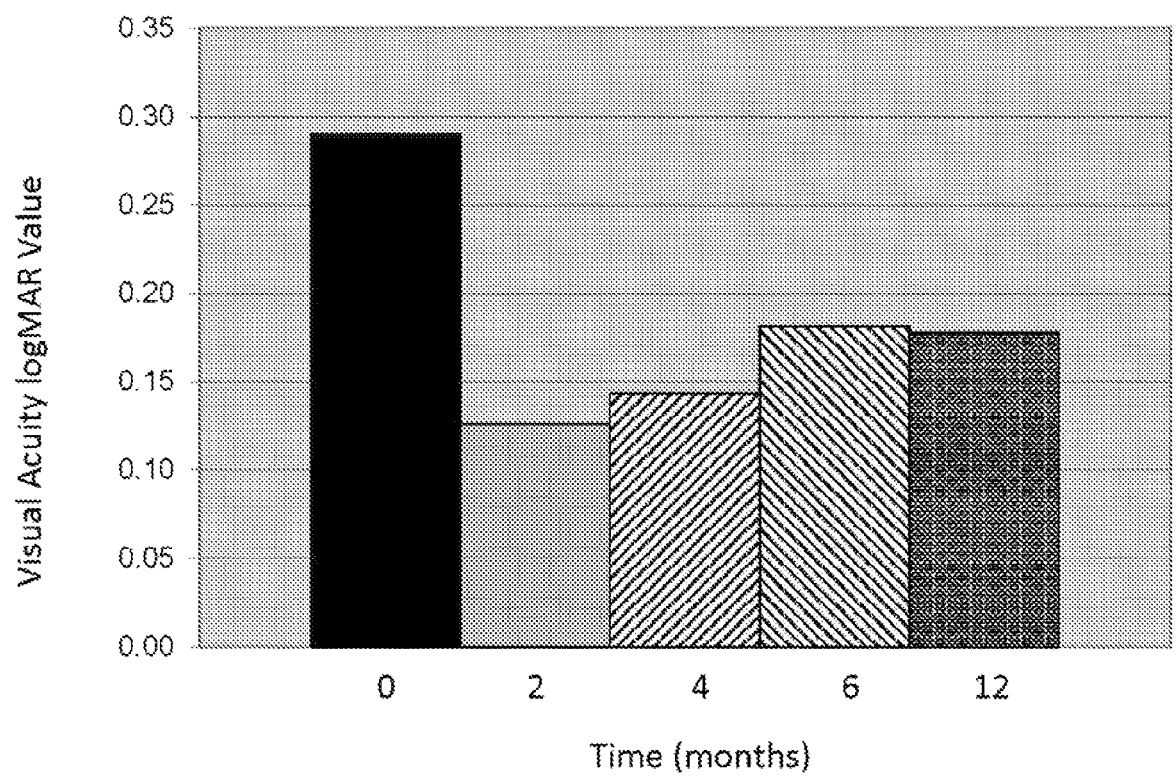
FIG. 18 is a bar graph of ETDRS Visual Acuity (in log MAR units), which shows an average Log MAR ETDRS score for all patients prior to treatment (0) and at 2, 4, 6, and 12 months post-treatment with a course of multi-wavelength photobiomodulation therapy according to the systems and methods of the present disclosure (described in Example 1). N=18. Repeated Measures ANOVA yielded F (4.68)=18.86, p less than 0.0001. (i.e., statistically significant).
Figure 19A:
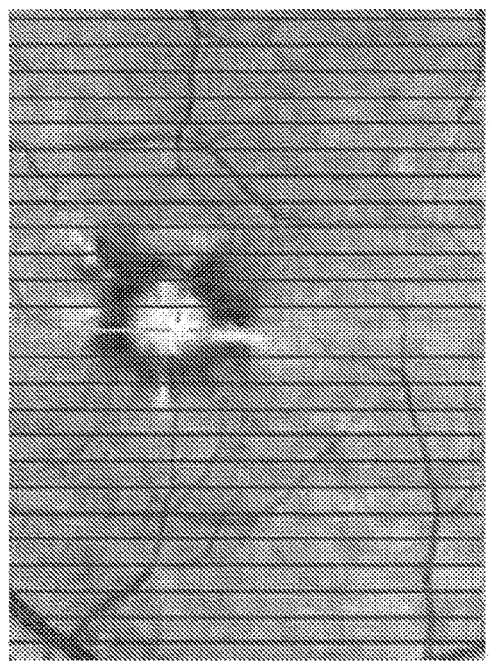
FIGS. 19A and 19B are ocular coherence tomography (OCT) data (representative of the data described in Example 2 and summarized in Table 1) that shows retinal scan and sections (FIG. 19A), retinal thickness (FIG. 19B), in particular at the central macula, in a patient afflicted with dry adult-onset macular degeneration (dry AMD) who underwent a course of multi-wavelength photobiomodulation therapy according to the systems and methods of the present disclosure.
Figure 19B:
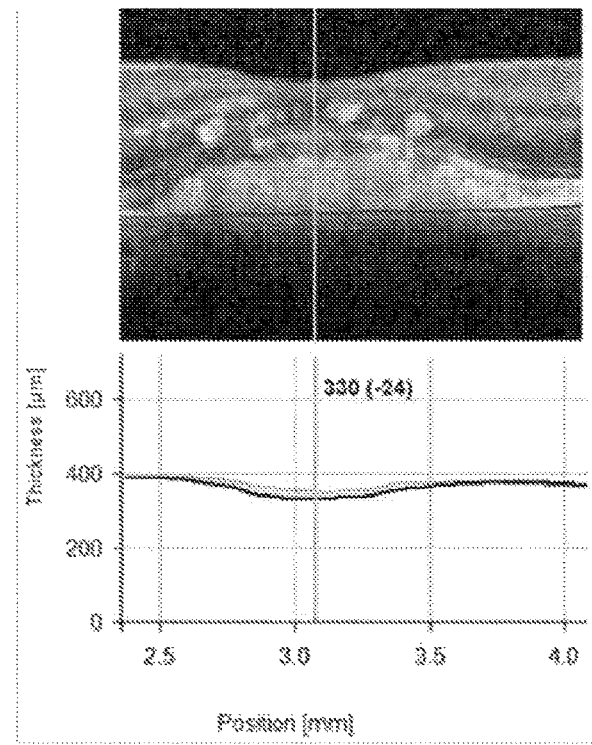

ETDRS visual acuity was statistically significantly improved immediately following the treatment and this clinical improvement remained at statistically significant levels at 12 months although some decline in the ETDRS log MAR score was evident after 4 months (FIG. 18).

Photobiomodulation is extremely well tolerated. No discomfort was reported and individual treatments were easily dispensed in less than 5 minutes per eye. No significant adverse events were noted during the course of the study described in the present example.

Example 2

Photobiomodulation (PBM) Methods for Decreasing Central Retinal Thickness in Dry Age-Related Macular Degeneration (AMD)

This Example demonstrates, through ocular coherence tomography (OCT) measurements, that photobiomodulation (PBM) can be employed advantageously in methods for decreasing central retinal thickness in the eyes of patients afflicted with dry age-related macular degeneration (AMD).

In a separate non-randomized case series, eight (8) patients afflicted with dry age-related macular degeneration (dry AMD) were treated with multi-wavelength phototherapy over three weeks. Clinical endpoints of CS and VA were conducted as in Example 1. In addition, changes in retinal thickness were determined from consecutive spectral domain ocular coherence tomography (SD-OCT) scans before and after treatment. An overall decrease in central retinal thickness was observed in dry AMD patients immediately following treatment with multi-wavelength phototherapy according to the systems and methods disclosed herein. In total, these data support the clinical and anatomical therapeutic efficacy of those multi-wavelength photobiomodulation therapy systems and methods and confirms the application of those systems and methods for the non-invasive treatment of patients with dry AMD. The results are shown in Table 1.

Patients with dry AMD (determined to have no neovascular lesions on retinal inspection, fundus photography, OCT assessment, and IVFA (in some)) that underwent PBM therapy were evaluated with SD-OCT, before and after treatment, with the SPECTRALIS SD-OCT system (Heidelberg Engineering, Carlsbad, CA), which combines high-speed image acquisition and custom TruTrack technology to actively track the eye during imaging thereby minimizing motion artifact, enabling noise reduction, and permitting precise tracking over time. The result is point-to-point anatomical correlation between fundus and OCT scans that enables accurate and repeatable alignment of OCT and fundus images, greater image detail and clarity, and more confident assessment of small changes. By integrating SD-OCT with confocal laser scanning ophthalmoscopy (cSLO), the Heidelberg SPECTRALIS platform permits precise follow-up scan placement.

Volume retinal scans were obtained prior to treatment, immediately following the treatment course, and at subsequent intervals following treatment. The same data collection methods that were used in the study presented in Example 1 were utilized for Visual Acuity with ETDRS charts at 4 meter distance (Precision Vision, USA) recorded in letter score, contrast sensitivity at 3 cycles per degree (Stereo Vision Optec 6500, USA) recorded as log contrast sensitivity. In addition, consecutive testing with the Heidelberg Spectralis SD-OCT was used in this group of patients, which revealed changes in retinal thickness.

Patients were treated three times a week for three weeks for a total of nine sessions in which they received the same total dose of PBM as the study described in Example 1, but with a shorter treatment time to facilitate patient compliance. These sessions included the use of PBM in the yellow and red to near-infrared (NIR) range using low-energy delivery with the Warp10 (Quantum Devices) and the Gentlewaves (Light Bioscience) instruments. The treatment parameters followed for the Warp10 delivery system were 670 nm 15 nm at 50-80 mW/cm$^2$, 4-7.68 J/cm$^2$, for 88±8 seconds. The treatment parameters followed for the Gentlewaves delivery system were 590 nm±8 nm at 4 mW/cm$^2$, 790 nm±60 nm at 0.6 mW/cm$^2$ for 35 seconds, pulsed at 2.5 Hz (250 milliseconds on, 150 milliseconds off) while delivering 0.1 J/cm$^2$/treatment. These three wavelengths were pre-selected to stimulate the CuA and CuB moieties of mitochondrial cytochrome C oxidase (CCO) activity and to suppress levels of VEGF protein production. All AMD patients were treated with the two devices used sequentially at each treatment visit and then repeated in the same session.

Following is a brief description of each patient and results from the SD-OCT analyses for each.

Subject 1 was a 55-year old Caucasian female who exhibited a reduction in central retinal thickness of 24 microns immediately following treatment, which further reduced to 27 microns at three months. Subject 1 elected to undergo a further 3-week treatment course. At four months the decrease in retinal thickness was 19 microns. Subject 1 had an initial letter score of 39, which increasing to 47 immediately post treatment and to 46 at three months and to 42 following the second course of treatment.

Subject 2 was a 52-year old Caucasian male who exhibited an increase in letter score from 52 to 57 immediately post treatment and a contrast sensitivity increase from log 1.76 to log 2.06. A subtraction scan showed a change of retinal thickness in a post-treatment scan as compared to the pre-treatment reference scan. The central minimum decreased by 20 microns. On this individual section there was an 18 micron decrease in retinal thickness over the highest point of Patient 2's central druse immediately following the treatment.

Subject 3 was a 68-year old Caucasian female who exhibited a 14 micron reduction in central fovea thickness following the treatment protocol. Her letter score increased from 55 to 58 and the contrast sensitivity increased from log 1.60 to log 1.90.

Subject 4 was an 85-year old Caucasian female who had a pre-treatment letter score of 51, which increased to 55 post-treatment, and at 53 one year out from treatment. The log CS score increased from 1.60 to 1.76. The OCT scan at one year showed a decrease of 18 microns. At the one year stage she elected to undergo another course of treatment and three months post treatment the central retinal thickness had decreased to 25 microns from the reference scan. At six months post second treatment the retinal thickness remained decreased at 19 microns. At one-year post second treatment the retinal thickness showed an 18 micron reduction. Three months following second treatment course (17 months from baseline) showing 25 micron reduction. A subtraction thickness map demonstrated an overall central decrease in retinal thickness 20 months from baseline following two treatment courses.

Subject 4's one-year follow-up OCT scan showed an 18 micron reduction in retinal thickness with improvement in CS and VA. Subject 4's three-month post-second treatment course (i.e., 17 months from baseline) OCT scan showed a 25 micron reduction in retinal thickness.

Subject 5 was an 80-year old Caucasian male who had a letter score of 48 prior to treatment increasing to 53 immediately post treatment and a large gain in log CS from 1.00 to 1.90. Two sections (cuts 12 and 13) of Subject 5's post treatment scan showed a decrease of 45 microns and 22 microns respectively.

Subject 6 was a 67-year old Caucasian male who had an initial letter score of 31 increasing to 36 post-treatment and a 19 micron reduction in retinal thickness. Contrast sensitivity increased from log 1.00 to log 1.18.

Subject 7 was an 86-year old Caucasian female who underwent treatment of both eyes. Subject 7 exhibited an initial letter score of 51 increasing to 54 post treatment, 54 at three months and 57 at six months. Log CS scores were 1.6 initially increasing to 1.9 post treatment, 1.76 at three months and 1.6 at six months. Initial letter score of 41 increasing to 43 and remaining at 43 for all subsequent visits. Log CS started at 1.46, remained at 1.46 post treatment, increased to 1.60 at three months and was 1.46 at six months.

The results presented in Examples 1 and 2, which are presented in FIGS. 16-19B and summarized in Table 1, demonstrated anatomical changes in central retinal thickness with a reduction in the central retinal area especially noted directly over the most diseased retina and no reduction in retinal thickness over the normal areas suggesting that the treatment is specifically reducing the retinal thickness over the diseased retina. Anatomical evidence with the resolution of the SD-OCT scans and ensuring the same retinal locations are scanned for serial measurements is unlikely to be influenced by a placebo effect and represents a significant objective end point that can be used in future clinical trials.

TABLE 1

Drusen Reduction in Patients with Dry AMD Following Photobiomodulation Treatment

| SUBJECT | DRUSEN REDUCTION (µM) | VISUAL ACUITY (ETDRS LETTER INCREASE) | CONTRAST SENSITIVITY (LOG UNIT INCREASE) |
|---|---|---|---|
| 1 | 24 | 8 | 0.3 |
| 2 | 20 | 5 | 0.3 |
| 3 | 14 | 3 | 0.3 |
| 4 | 18 | 4 | 0.16 |
| 5 | 45 | 5 | 0.9 |
| 6 | 19 | 5 | 0.18 |
| 7 (OD) | 13 | 4 | 0.3 |
| 7 (OS) | 27 | 2 | 0.0 |
| MEAN | 22.5 | 4.5 | 0.305 |
| STANDARD DEVIATION (SD) | 10.21 | 1.77 | 0.26 |
| STANDARD ERROR OF THE MEAN (SEM) | 3.61 | 0.63 | 0.09 |

The seven subjects who participated in this case series also showed improvements in vision and contrast sensitivity, which were consistent with the improvements that were observed in the dry AMD clinic pilot study that are presented in Example 1. The anatomical evidence presented herein, which resulted from high-resolution SD-OCT scans thus ensuring that the same retinal locations were scanned for serial measurements, represent a significant objective end point, which is unlikely to have been influenced by a placebo effect and can be used in future clinical trials. These objective changes in retinal anatomy following PBM therapy and their correlation with improvement in subjective parameters (i.e., ETDRS, VA, and CS) support the use of PBM for the non-invasive, low-risk treatment of patients with dry AMD.

PBM has been shown recently to cause a significant reduction in focal retinal thickening in non-central diabetic macular edema. Tang et al., *Br J Ophthalmol*, published online 28 Mar. 2014 doi:10.1136/bjophthalmol-2013-304477. While the device used in the study described by Tang et al. was identical to the device utilized in the case series presented in Example 2, the present study with AMD patients employed pulses of yellow and infrared wavelength light that was designed to affect a reduction in vascular endothelial growth factor expression to reduce the conversion of dry AMD to wet AMD. Kiire et al., *Retina Today* (January/February 2011) (sub-threshold micropulse laser therapy for retinal disorders; Barnstable et al., *Prog Ret Eye Res.* 23(5):561-577 (2004); Glaser et al., *Ophthalmology* 94:780-784 (1987); Miller et al., *Invest. Ophthalmol. Vis. Sci.* 27:1644-1652 (1986); and Ogata et al., *Am. J. Ophthalmol.* 132(3):427-429 (2001).

Example 3

Further Treatment of Dry Age-Related Macular Degeneration Patients in an Ongoing Patient Data Collection (TORPA II)

The study that is presented in Example 3 was designed as a patient data collection in which low powered light at near infrared (NIR), far red and yellow wavelengths was applied, in serial consecutive treatments, to the eyes of patients with dry AMD. This TORPA II study examined the use of photobiomodulation (PBM) as a treatment for visual outcomes as well as anatomical changes to the retina in subjects with dry AMD. This study included subjects who met the inclusion and exclusion criteria and underwent off-label PBM treatment following conclusion of the previously published TORPA study.

Included in this study were patients with dry AMD who were 50 years or older and having best corrected visual acuity (BCVA) ranging from 20/20 to 20/200. Primary outcome measures included: (i) visual acuity and (ii) contrast sensitivity. Excluded from the study were subjects with previous or active wet AMD, with a previous history of epilepsy, with cognitive impairment, other retinal disease, previous retinal surgery, significant media opacity, or contraindications to dilation drops.

The absence of neovascularization was ascertained prior to enrollment by examination with Ocular Coherence Tomography (OCT) and Intravenous Fluorescein Angiography (IVFA) and confirmed by a retina specialist. All subjects were assessed for Visual Acuity with ETDRS charts at 4 meter distance (Precision Vision, USA) recorded in log MAR units, contrast sensitivity at 1.5, 3 and 6 cycles per degree (Stereo Vision Optec 6500, USA) recorded as log contrast sensitivity. Measurements took place: (i) prior to treatment; (2) immediately following a 3-week treatment protocol; (3) at 3 months following the treatment protocol; (4) at 6 months following the treatment protocol; and (5) at 12 months following the treatment protocol. At this time, patients were still participating in the treatments so a partial listing of the data is presented.

The intervention included the use of PBM in the yellow, far red and near infrared (NIR) range using low energy delivery with the Warp10 (Quantum Devices) and the Gentlewaves (Light Bioscience) instruments, which are commercially available and approved by the FDA and Health Canada for use in other conditions. The treatment parameters followed for the Warp10 delivery system were 670 nm f 15 nm at 50-80 mW/cm$^2$, 4-7.68 J/cm2, for 88±8 seconds. The treatment parameters followed for the Gentlewaves delivery system were 590 nm±8 nm at 4 mW/cm$^2$, and 790 nm±60 nm at 0.6 mW/cm$^2$, for 35 seconds, pulsed at 2.5 Hz (250 milliseconds on, 150 milliseconds off) while delivering 0.1 J/cm$^2$/treatment.

The goal of this patient data collection was to reduce the overall number of treatments while maintaining the same total PBM dose and demonstrating safety and efficacy. All subjects were treated with the two devices used sequentially at each treatment visit for a total of 9 treatments over a three-week period (3 times per week for 3 weeks). In the 3-week treatment group, patients were give the same total PBM dose as in the 6-week treatment group, but each session had a double treatment.

Descriptive statistics for all endpoints for each treatment will include the number of subjects, mean, standard deviation, median, minimum and maximum for continuous variables, and frequencies and percentages for categorical variables. Differences were considered to be statistically significant at p values of less than 0.05. Primary analysis.

VA effect of PBM: The primary analysis will test the difference in PBM-treated subjects in mean change from BL (pre-treatment) to 3 weeks following treatment in VA. Analysis will use a linear mixed effects model. Exploratory analyses will examine the same endpoint at Months 3 and beyond depending on sample size.

Secondary analysis. CS effect of PBM: The first of the secondary analyses will test the difference in PBM-treated subjects in mean change from BL (pre-treatment) to 3 weeks following treatment in contrast sensitivity. Analysis will use a linear mixed effects model. Exploratory analyses will examine the same endpoint at Months 3 and beyond depending on sample size.

Impact on retinal imaging using fundus auto-fluorescence (FAF) and optical coherence tomography (OCT) of PBM: The OCT scan will compare reproducible scans at the exact anatomical area of the reference scan and subjects will be scanned at BL for confirmation of dry AMD pathology. Repeat FAF and OCT scans will be taken following treatment and at follow-up visits (e.g., 3, 6 and 12 months). The OCT analysis was exploratory. Descriptive statistics were generated with pre-treatment and post-treatment FAF and OCT scans. For the FAF and OCT imaging analysis, a centralized reader identified anatomic parameters to compare pre- and post-PBM anatomical changes. The OCT analysis examined change from baseline to 3 weeks following treatment. Analysis will use a linear mixed effects model. Exploratory analyses examined the same endpoint at Months 3 and beyond depending on sample size. Drusen volume, mean central 1 mm drusen thickness, and geographic atrophy lesion area after square root transformation were the main outcome measures here. Additionally CRT and retinal volume were assessed. Analyses was performed to compare efficacy in subgroups by AREDS category and by reticular pseudodrusen (RPD) presence or absence. Intact photoreceptor status pre- and post-treatment was compared using a Fisher Exact test. Variables that are not normally distributed may be analyzed using a power transform or using rank values.

Figure 20:
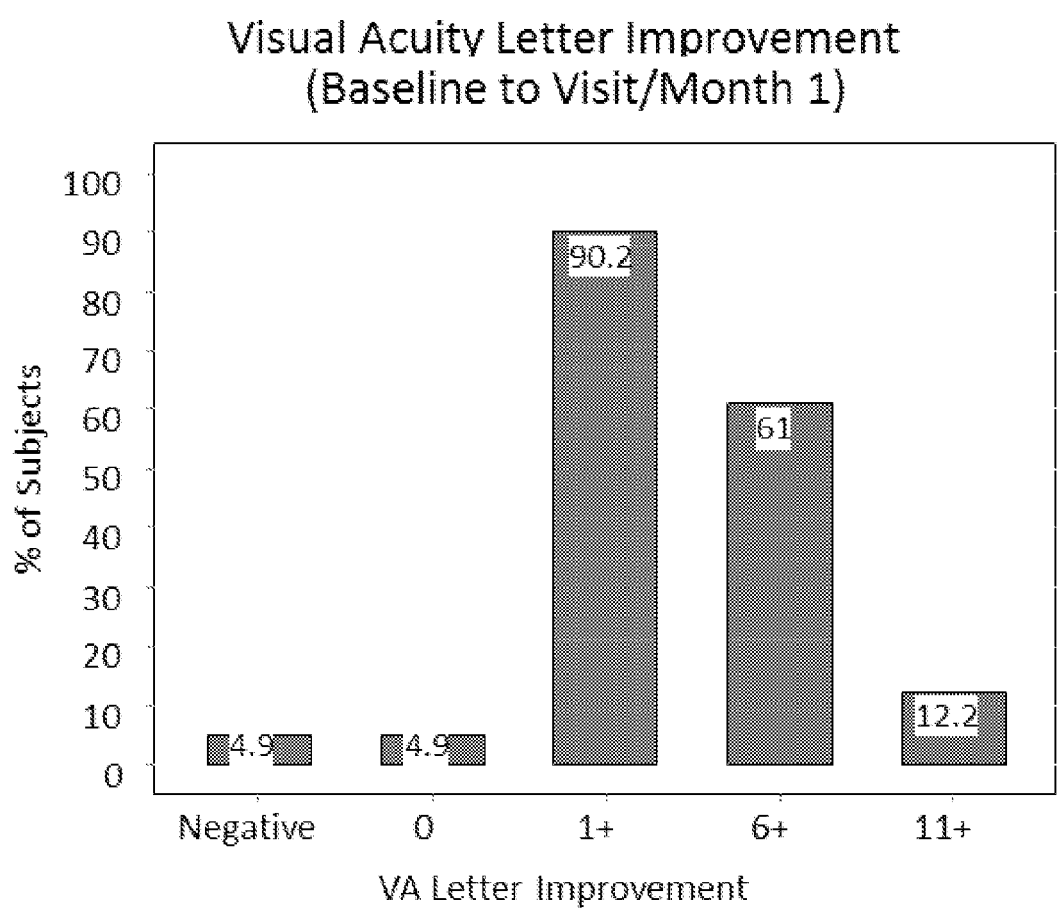
FIG. 20 is a graph showing the percentage of patient's eyes achieving visual acuity (VA) ETDRS Line improvement following a 3× per week for 3-week treatment. T-test comparison between the pretreatment baseline VA mean letter score versus the VA mean letter score following 3-week treatment was statistically significant, p<0.05. N=41 eyes.
Figure 21:
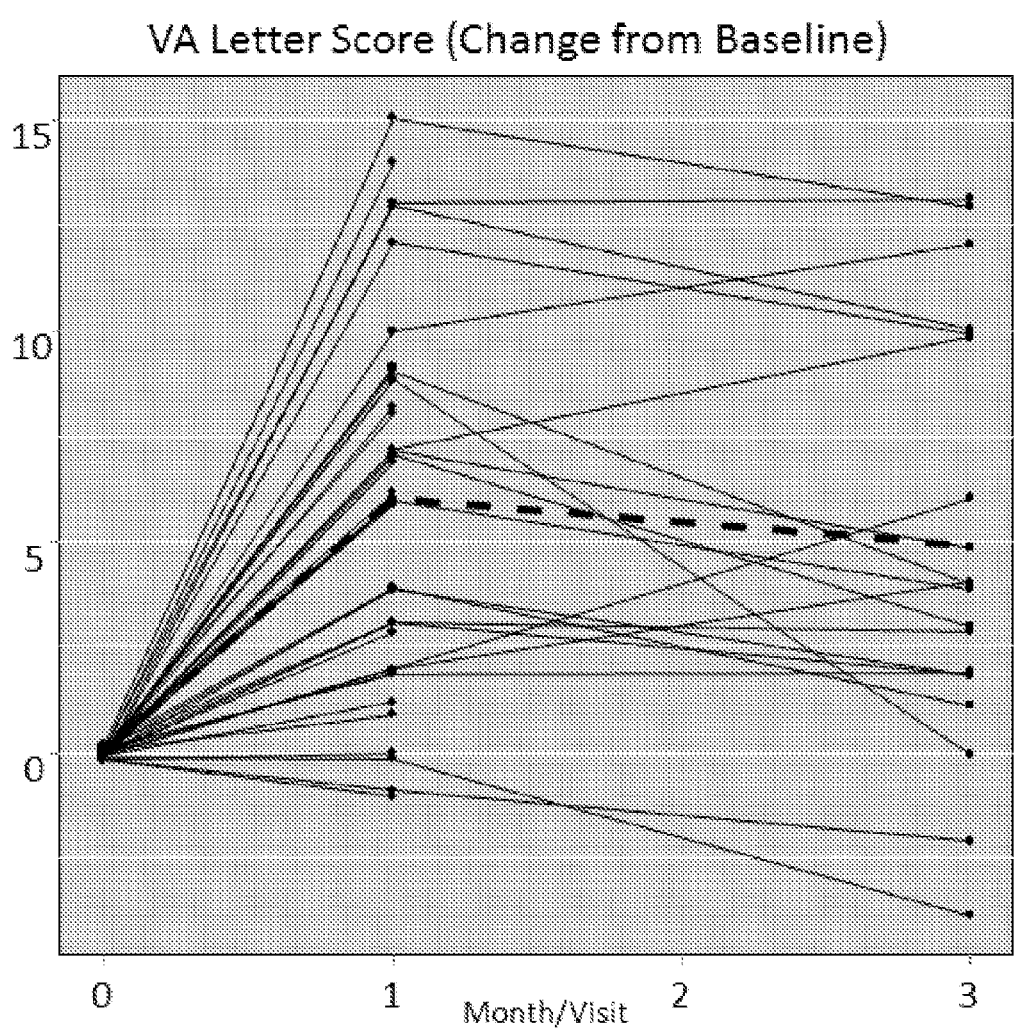
FIG. 21 is a graph showing a change in visual acuity (VA) letter score (change from background) for individual patients following a 3× per week for 3-week treatment. T-test comparison between the pretreatment baseline VA letter score versus the VA letter score following 3-week treatment was statistically significant, p<0.05. N=41 eyes.

Approximately 41 dry AMD study eyes were included in this analysis. The patients were all 3-week treatments. The preliminary data for the 3× per week for 3-week data is shown for VA (FIGS. 20 and 21).

TABLE 2

VA and CS Clinical Improvement and Central Drusen Reduction in
Patients with Dry AMD Following Photobiomodulation Treatment

| Group | Mean | S.D. (+/−) |
|---|---|---|
| Visual Acuity @ Baseline (letter score) | 41.29 | 11.36 |
| Visual Acuity @ 3 weeks (letter score) | 47.32 | 11.29 |
| Visual Acuity @ 3 months (letter score) | 50.050 | 6.353 |
| Contrast Sensitivity @ Baseline (log) | 1.503 | 0.229 |
| Contrast Sensitivity @ 3 weeks (log) | 1.605 | 0.243 |
| Contrast Sensitivity @ 3 weeks (log) | 1.664 | 0.181 |
| Central Drusen @ Baseline (volume) | 0.460 | 0.144 |
| Central Drusen @ 3 weeks (volume) | 0.445 | 0.169 |
| Central Drusen @ 3 months (volume) | 0.431 | 0.039 |

The PBM treatment regimen disclosed in this example also revitalized, rejuvenated, and improved the function of compromised retinal cells on the border of the geographic atrophy with an immediate statistically significant improvement in visual acuity (FIGS. 20 and 21) and contrast sensitivity (data not shown). The clinical benefits were still statistically significant at the 3-month interval for both clinical outcome measures.

Visual acuity was statistically significantly improved immediately following the 3-week treatment and this clinical improvement was similar in benefit to the extended 6-week treatments in the TORPA study (FIGS. 16-18). The two treatments provided the same total dose of the three wavelengths but were optimized to reduce the total number of treatment sessions. Further analysis will determine the frequency of repeated treatments to maintain the maximal benefit.

The data presented in this Example demonstrate that the PBM systems and methods disclosed herein are well-tolerated and, more specifically, that no discomfort was reported, individual treatments were easily dispensed in less than 5 minutes per eye, and no significant adverse events were noted during the course of the presently-described study.

Figure 22:
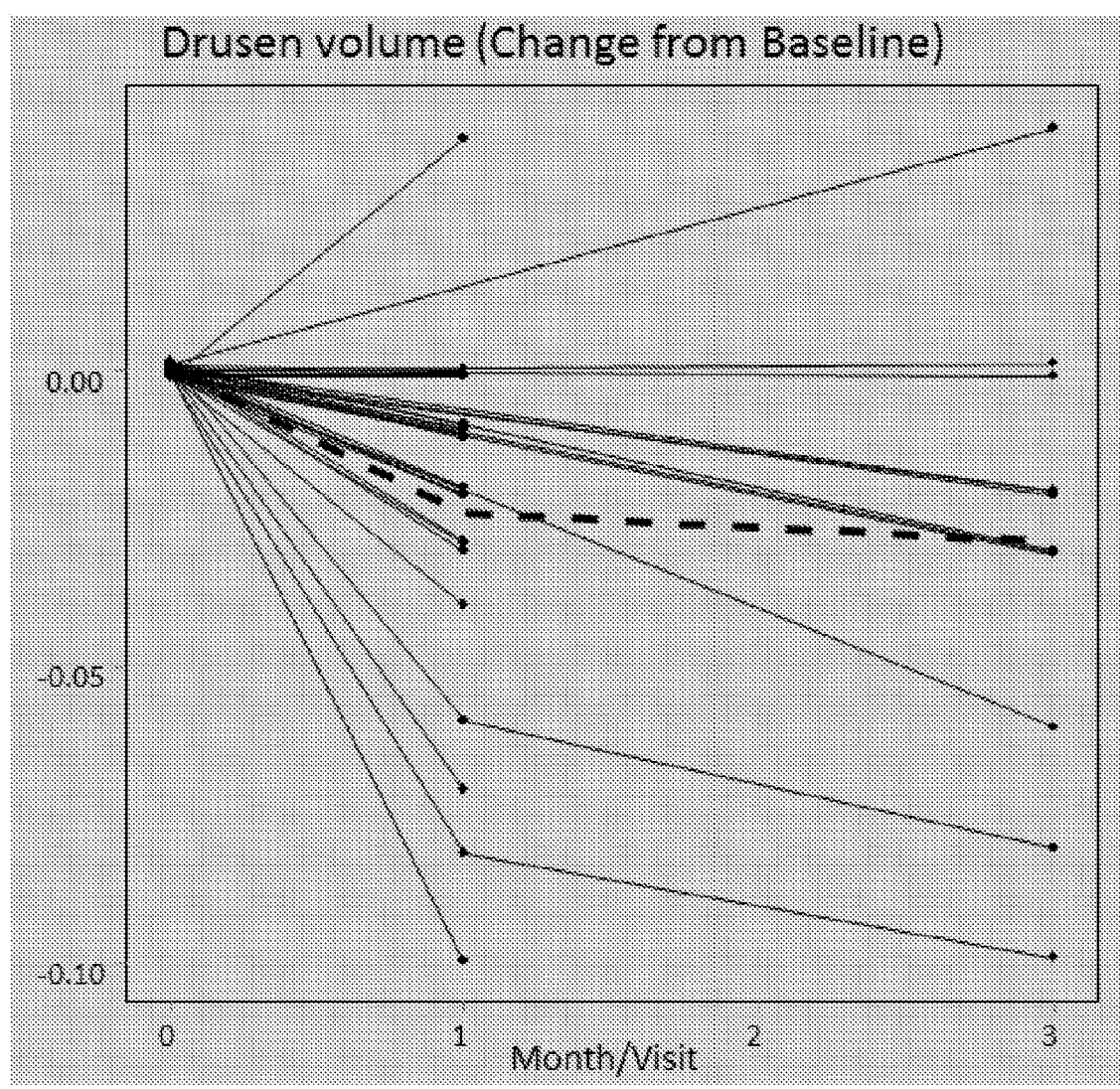
FIG. 22 is a graph showing a reduction in anatomical pathology (drusen volume) following a photobiomodulation ("PBM") therapy protocol according the methods disclosed herein. Data are from individual patients following a 3× per week for 3-week treatment. T-test comparison between the pretreatment baseline Drusen volume versus the Drusen volume following 3-week treatment was statistically significant, p<0.05. N=41 eyes. These data demonstrate a therapeutic benefit of PBM therapy according to the methods of the present disclosure.

More surprising is that the PBM treatment lead to significant reductions in central drusen volume, the hallmark pathology of the disease. The reduction was evident immediately after the 3-week treatment and was maintained at the 3-month time period following treatment by analyzing the optical coherence tomography (OCT) retinal scans in 19 patients and 33 eyes (Table 3 and FIG. 22). This is the first time that a treatment has shown both clinical as well as anatomical benefits in central drusen volume. No impact was seen on the retinal photoreceptor layer demonstrating the safety of the PBM treatment at the anatomical level with a beneficial reduction in the pathology of dry AMD disease without any local cellular damage. The visual acuity (VA), contrast sensitivity, and central drusen data obtained through the presently disclosed TORPA II study are summarized in FIG. 23.

TABLE 3

Optical Coherence Tomography Determined Reduction
in Central Drusen Volume in Dry AMD Subjects

| Group | Mean | p Value |
|---|---|---|
| Central Drusen Volume BL vs V1 (3 week) | .024 | P = 0.0008 |
| Central Drusen Volume BL vs V2 (3 month) | .029 | P = 0.02 |

Example 4

Cadaver Studies

Each wavelength has distinct tissue scatter and light penetration properties, thus to ensure the effective delivery of a known intensity of light to ocular tissue, the optical properties of intervening tissues at the wavelengths of interest were obtained through the presently-disclosed study in which light transmission was measured through a set of human cadaver eyes. The design of the experiments performed during and the data obtained from that cadaver study established the retinal fluence rates resulting from the application of light of specific wavelength and power to the ocular region. The results disclosed herein were used to determine the expected retinal fluence rates in the clinical study (TORPA) disclosed in Example 3 and, accordingly, to establish the safety limits for future therapeutic devices.

Figure 28:
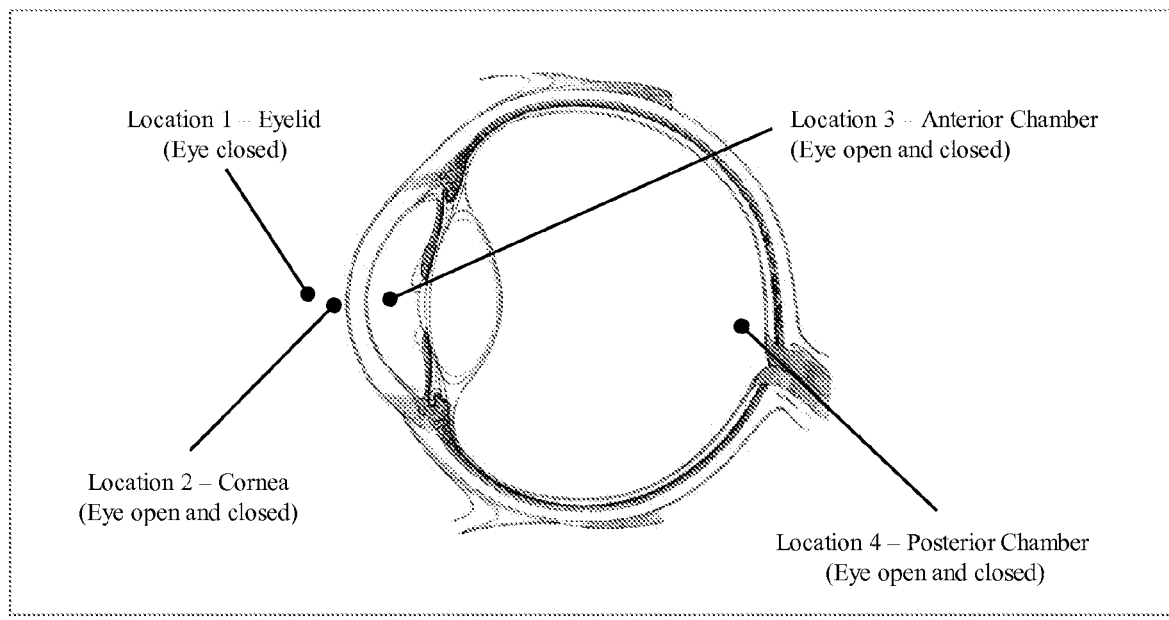
FIG. 28 is a drawing showing the principle measurement locations used in the cadaver study disclosed herein and described in detail in Example 4.

Power measurements within the eye were taken with an isotropic fiber probe from Medlight (SD200), connected to a silicon-based power detector from Opir (PD300). The detector was connected to an Ophir meter (Nova II). The full device output was measured with a large area, thermal-based power meter from Ophir (L50) 300A, which was connected to the same meter. Spectral measurements were made with an Ocean Optics spectrometer (USB2000) and saved to a laptop. The general procedure for testing each eye is outlined in Table 4, with the measurement locations shown in FIG. 28.

TABLE 4

| STEP | DESCRIPTION |
|---|---|
| 1 | A power out of the device was measured for all three sources. |
| 2 | The fiber probe was placed on the eyelid of the cadaver eye and was held in place with tape to the skin on the cheek. |
| 3 | The cadaver head was positioned in front of the device, and the device output was adjusted to such that it was centered on the eye. |
| 4 | The amber, red, and IR sources were activated sequentially and the power from the probe was recorded for each source. |
| 5 | The probe was moved to the cornea, and step 4 was repeated. |
| 6 | The spectra from all three sources was measured and recorded. |
| 7 | The eyelid was closed over the probe and step 4 was repeated. |
| 8 | The spectra from all three sources was measured and recorded. |
| 9 | The probe was removed and inserted into the anterior chamber of the eye. The eyelid was opened, and step 4 was repeated. |
| 10 | The eyelid was closed and step 4 was repeated. |
| 11 | The probe was removed and inserted into the posterior chamber of the eye. The eyelid was opened, and step 4 was repeated. |
| 12 | The spectra from all three sources was measured and recorded. |
| 13 | The eyelid was closed and step 4 was repeated. |
| 14 | The spectra from all three sources was measured and recorded. |

For each cadaver, measurements were made on both eyes. Six (twelve eyes) were used in the main study.

Subject data for each specimen in the main study is given in Table 5, along with any applicable observations. Skin color was qualitatively evaluated per the Fitzpatrick skin type classification scale.

TABLE 5

Subject Information

| Subject | Gender | Days Post-Mortem | Age | Race | Skin Color | Cause of Death | Comments |
|---|---|---|---|---|---|---|---|
| 936 | F | 70 | 99 | Caucasian | II | Alzheimer's disease | Macular degeneration since 2001 |
| 949 | M | 14 | 72 | Caucasian | III | Cardiovascular and pulmonary collapse | Cataract surgery history -unknown date |
| 950 | M | 21 | 80 | Caucasian | III | End state renal disease | Status epilepticus |
| 957 | M | 17 | 83 | Caucasian | II | Respiratory failure, septic shock, pneumonia | |
| 956 | F | 28 | 86 | Caucasian | II | Dementia | |
| 953 | F | 31 | 75 | Caucasian | II | Complications from lung cancer | MS but it did not affect the visual system |

The device output power, P3, for each source was transcribed from the data collection sheets into an electronic database. The raw measurement data were also transcribed from the collection forms. These raw data do not represent true fluence levels, but rather the power delivered from the probe to the Ophir PD300 detector, as indicated on the meter. To convert these to actual fluence rates (mW/cm$^2$), they must be multiplied by a calibration factor to account for the probe collection efficiency, the spectral response of the detector, and isotropy of illumination. Calibration factors were determined for each source though testing and are presented in Table 6.

TABLE 6

Calibration Factors

| Probe Condition | Isotropic Calibration Factors (mW/cm2 per µW) | | |
|---|---|---|---|
| | Red | Amber | IR |
| Wet | 9.878 | 13.949 | 5.967 |
| Dry | 6.315 | 8.558 | 3.703 |
| Average | 8.096 | 11.254 | 4.835 |

As seen in Table 6, the calibration value for the probe was different depending on whether the probe is wet or dry. Accordingly, the correct value to use was dependent upon the location of the probe during a particular measurement. For measurements made at the eyelid, the "dry" calibration value was used, since the probe was surrounded mostly by air. When taking measurements within the anterior and posterior chambers of the eye, the probe was immersed in fluid, so the "wet" calibration value was used for these readings. The "wet" value was used for measurements at the cornea with the eye closed, since the majority of the probe was in contact with wet tissue at that location. For measurements at the cornea with the open eye, the average value of the wet and dry calibration value was used, since the probe was only in partial contact with wet surfaces during those readings.

These calibration values were applied to the raw recorded data, and the data was then normalized to a common value of 1 W power output from the device for each source. The mean and standard error of each measurement is presented in Table 7. Those data are illustrated graphically in FIG. 29, where the mean fluence rate and standard error are plotted as function of measurement location for the open eye.

TABLE 7

Mean ± SEM of Normalized Fluence Rates for the Open Eye

| | Normalized Fluence Rates (mW/cm$^2$) per 1 W Device Power Mean ± SEM | | |
|---|---|---|---|
| Location | Amber | Red | IR |
| Eyelid | 228.10 ± 12.34 | 169.54 ± 5.64 | 183.07 ± 4.53 |
| Corneal Surface (open) | 249.46 ± 17.86 | 171.51 ± 6.68 | 188.25 ± 4.67 |
| Anterior Chamber (open) | 176.79 ± 16.94 | 133.22 ± 11.95 | 185.77 ± 12.20 |
| Posterior Chamber (open) | 15.06 ± 8.27 | 17.81 ± 5.73 | 11.02 |

The uncertainty of each measurement is a direct function of the uncertainty of the calibration value. These were calculated for each source and an additional ±3% was added to account for the uncertainty in the meter used to measure the total device power. The resulting total uncertainties were then ±7.3% for the amber, ±14.3% for the red, and ±6.9% for the IR. Uncertainties in the probe location during measurements were estimated to be ±2 mm for the eyelid, cornea, and anterior chamber, and ±5 mm for the posterior chamber. The mean fluence rate and standard error are presented as a function of measurement location for the closed eye in Table 8 and are illustrated graphically in FIG. 30, where the mean fluence rate and standard error are plotted as function of measurement location for the closed eye. The spectra collected at each location were imported into Matlab and normalized for comparison.

TABLE 8

Mean ± SEM of Normalized Fluence Rates for the Closed Eye

| | Normalized Fluence Rates (mW/cm$^2$) per 1 W Device Power Mean ± SEM | | |
|---|---|---|---|
| Location | Amber | Red | IR |
| Eyelid | 228.10 ± 12.34 | 169.54 ± 5.64 | 183.07 ± 4.53 |
| Corneal Surface (closed) | 101.21 ± 18.25 | 120.20 ± 13.89 | 143.55 ± 18.35 |

TABLE 8-continued

Mean ± SEM of Normalized Fluence Rates for the Closed Eye

| Location | Normalized Fluence Rates (mW/cm$^2$) per 1 W Device Power Mean ± SEM | | |
|---|---|---|---|
| | Amber | Red | IR |
| Anterior Chamber (closed) | 46.17 ± 9.83 | 61.70 ± 10.03 | 107.55 ± 12.56 |
| Posterior Chamber (closed) | 4.66 ± 2.19 | 11.56 ± 3.36 | 34.98 ± 6.37 |

For each curve, the peak wavelength was determined. The minimum, maximum, mean, and standard deviation of the peak for each source is presented in Table 9.

TABLE 9

Peak Wavelengths

| | Peak Wavelength (nm) | | | |
|---|---|---|---|---|
| Source | Mean | Min | Max | Standard Deviation |
| Amber | 597.4 | 594.5 | 600.1 | 2.0 |
| Red | 668.5 | 657.9 | 676.3 | 7.7 |
| IR | 858.1 | 852.6 | 861.7 | 2.9 |

Some variation in the measured spectra occurred during testing, most notably in the red source. This variation was independent of the measurement location, and was highly dependent on LED power output during the spectral readings. This was understandable and predictable, as there is a dependence of output spectra on LED temperature, which increases as power is increased. Comparing the measured spectra of all the sources to their published specifications shows the range of peak wavelengths all to be within specifications.

Figure 29:
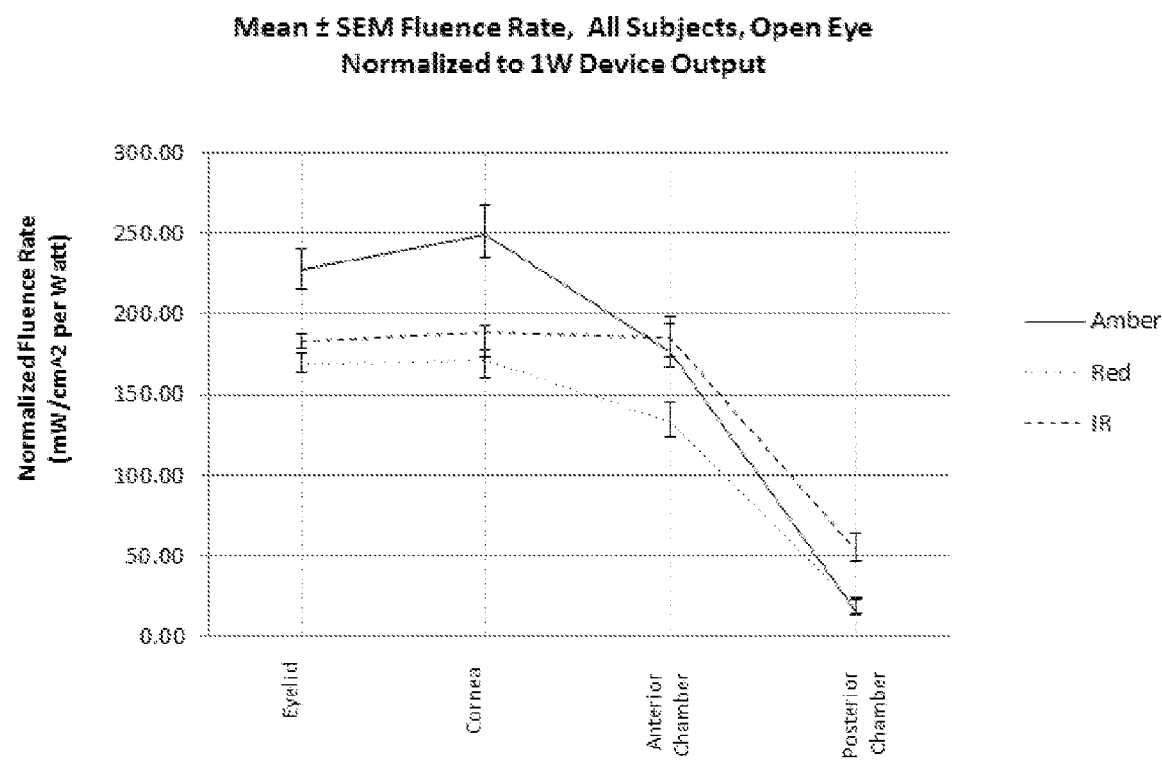
FIG. 29 is a graph showing mean fluence rates (open eye) that were obtained from the cadaver study disclosed herein and described in detail in Example 4.
Figure 30:
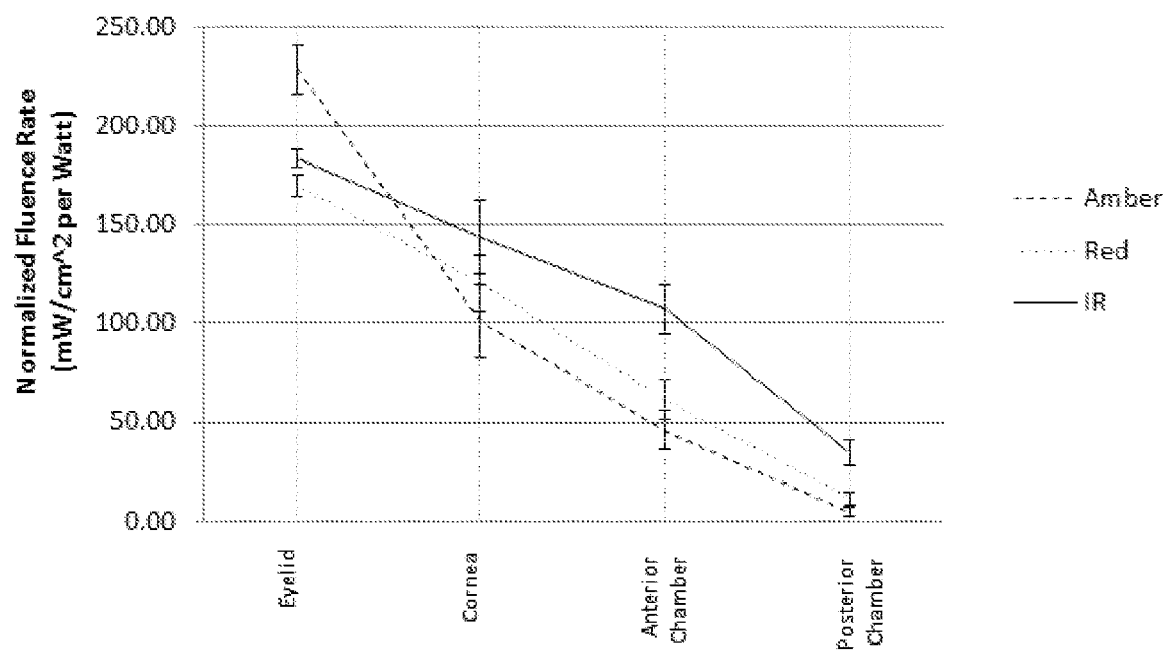
FIG. 30 is a graph showing mean fluence rates (closed eye) that were obtained from the cadaver study disclosed herein and described in detail in Example 4.

For the open and closed eye, the measured fluence rates presented in FIGS. 29 and 30 follow an expected trend, with the highest transmission in the infrared, followed by the red and amber. This is consistent with published transmission data on human tissue.

While the results presented herein are normalized to a device power of 1 W, the fluence rate at the eyelid, prior to transmission through any tissue, is significantly higher with the amber wavelength than in the other two wavelengths. This variation is potentially understood when one considers that the probe is isotropic and collects both the light that is emanating from the instrument, as well as light that is reflected back from the eyelid and surrounding tissue. The variation, then, is indicative of a spectral dependence on the diffuse reflectance of the tissue, with the amber source being reflected at a higher percentage than the red or IR. This is in general agreement with previous measurements of diffuse reflectance of human skin. Murphy et al., *J. Biomed. Opt.* 10:064020 (2005) and Lim et al., *J. Biomed. Opt.* 16:011012 (2011).

An additional factor for establishing fluence values at the corneal surface may involve the choice of calibration value at that location. Though the "dry" value was used at the eyelid, the "average" value at the open-eye cornea, and "wet" value at the close-eye cornea, the degree of probe "dryness" or "wetness" in the later two locations could lead to variation. This may result in a more uncertainty on the calculated fluence rates at this location.

The optical emission limits for ophthalmic devices are defined by IEC 15004-2. (International Organization for Standardization. Ophthalmic instruments—Fundamental requirements and test methods—Part 2: Light hazard protection. ISO 15004-2:1-37 (2007)). Emission limits for Group 1 devices, which are defined to produce no emission hazard, are given in Table 10.

TABLE 10

Group 1 irradiance limits per IEC15004-2

| Parameter | Description | Calculation | Limit |
|---|---|---|---|
| $E_{A-R}$ | Retinal photochemical aphakic light hazard | $E_{A-R} = \sum_{305}^{700} E_\lambda \times A(\lambda) \times \Delta\lambda$ | $220 \frac{\mu W}{cm^2}$ |
| $E_{IR-CL}$ | Unweighted corneal and lenticular infrared radiation irradiance | $E_{IR-CL} = \sum_{770}^{2500} E_\lambda \times \Delta\lambda$ | $20 \frac{mW}{cm^2}$ |
| $E_{VIR-R}$ | Weighted retinal visible and infrared radiation thermal irradiance | $E_{VIR-R} = \sum_{380}^{1400} E_\lambda \times R(\lambda) \times \Delta\lambda$ | $700 \frac{mW}{cm^2}$ |

Using the above calculations, the specified limits, and the measured device spectra, the maximum irradiance limit for each source at the retina and cornea may be calculated. Results are presented in Table 11. These values assume the device is operating in continuous-wave (CW) mode, and that only a single source is activated at any given time.

TABLE 11

Maximum Irradiance Values per Source, Group 1, IEC15004-2

| Location | Amber | Red | IR |
|---|---|---|---|
| Retina | $110 \frac{mW}{cm^2}$ | $220 \frac{mW}{cm^2}$ | $1360 \frac{mW}{cm^2}$ |
| Cornea (IR only) | NA | NA | $20 \frac{mW}{cm^2}$ |

Dividing the values in Table 11 by the normalized fluence rates in Tables 5 and 6 gives the maximum output power of the device such that it may be classified as Group 1 per IEC 15004-2. To be conservative, the values from Tables 7 and 8 used in this calculation are maximums (average+SEM). Results are presented in Table 12. These values provide a direct comparison to commercial instruments and establish the safety class for therapeutic interventions.

TABLE 12

Maximum safe device output, Group 1, IEC15004-2

| Source | Eye State | Maximum Safe CW Device Power (W) |
|---|---|---|
| Amber | Open Eye | 4.7 |
| | Closed Eye | 16.1 |
| Red | Open Eye | 9.3 |
| | Closed Eye | 14.7 |
| IR | Open Eye | 0.10 |
| | Closed Eye | 0.12 |

The study presented in this Example provides a definitive understanding of light scatter and penetration in the human cadaver eye and to further establish the safety and efficacy of PBM in the human medical condition. The eye being a unique optical organ requires a special consideration of the light absorption and tissue scatter properties when developing therapeutic applications using light therapy. While cadavers are not living tissue, the anatomical features and tissue properties are very amenable to measurements of tissue scatter and absorption and allow estimates of human exposure of light in the clinical situation. The studies were further undertaken to illustrate the importance of establishing individual wavelength dependent dosing curves that represent actual tissue scatter and absorption for the given wavelength.

The study results presented herein demonstrate measurable light at all levels of the eye with increasing absorption as light penetrated deeper into the eye. Absorption was dependent on the wavelength and the results obtained were consistent with and confirm other studies looking at light scatter and absorption in human tissues. The NIR wavelength of light penetrated most readily in ocular tissue with less loss at the deeper areas including the anterior and posterior chambers. Yellow<far red<NIR were the established order of tissue penetration and supports other multi-wavelength tissue studies. Murphy et al., *J. Biomed. Opt.* 10:064020 (2005) and Lim et al., *J. Biomed. Opt.* 16:011012 (2011). These studies are essential to target the retina or other areas of the eye to allow optimization of the clinical doses.

The TORPA study presented in Example 3 (see, also, Merry et al., *Association for Research in Vision and Ophthalmology* 53:2049 (2012)) utilized two commercial instruments, the Quantum WARP 10 and the Gentlewaves. The wavelengths and doses presented in Table 13 were tested and repeated over a series of 6 weeks.

TABLE 13

TORPA Study Treatment Parameters

| Instrument | Wavelength (nm) | Irradiance at the Eye (mW/cm²) | Duration(s) | Pulse Profile | Eye State |
|---|---|---|---|---|---|
| Warp 10 | 670 ± 15 | 50-80 | 90 | CW | Closed |
| GentleWaves | 590 ± 8 | 4 | 30 | 2.5 Hz, 63% DC | Open |
| GentleWaves | 790 ± 60 | 0.6 | 30 | 2.5 Hz, 63% DC | Open |

Based upon the TORPA study parameters and the results obtained in the presently-disclosed cadaver study, the retinal fluence rates presented in Table 14 can be determined for the TORPA study.

TABLE 14

TORPA Study Retinal Fluence Rates, Calculated

| Instrument | Wavelength (nm) | Retinal Fluence Rate (mW/cm²) |
|---|---|---|
| Warp 10 | 670 ± 15 | 4.1-6.5 |
| GentleWaves | 590 ± 8 | 0.4 |
| GentleWaves | 790 ± 60 | 0.2 |

The cellular targets for the three wavelengths are different and thus have independent dose response curves, but the current study provides some context to the tissue exposure that translated to beneficial clinical outcome measures seen in the TORPA study. All fluences are well below the ocular safety standards set by the industry guidelines (i.e., IEC15004). However, there are distinct and surprising differences in the Fluence levels for the three wavelength that make this multi-wavelength approach effective in dry AMD.

The light emitted by the Lumithera LED device is non-coherent, as opposed to the coherent light produced by a laser, and no optical gain occurs within the diode. Consequently, safety standards have evolved to treat LEDs as equivalent to lamps that emit non-coherent light. Applicable standards include those formulated by the International Commission on Non-Ionizing Radiation Protection (ICNIRP), the American Conference of Governmental Industrial Hygienists (ACGIH), and numerous other independent researchers to cover non-coherent light sources. Exposure Limits (ELs) and Threshold Limit Values (TLVs) for LEDs have been established.

Cadaver testing of the three LED sources within the Lumithera device confirmed that the delivered doses of light for the amber, red, and NIR wavelengths were within established safety parameters, provided that the power emitted from the device for each source is kept below the associated value given in Table 14.

In total, the data presented herein support the safety and therapeutic efficacy of multi-wavelength photobiomodulation systems and methods and, moreover, demonstrate an objective improvement in retinal anatomy following multi-wavelength photobiomodulation therapy, which correlates with improved subjective parameters (ETDRS VA and CS). Thus, the data presented herein supports the use of the presently disclosed multi-wavelength phototherapy systems and methods for the treatment of disorders and diseases, including ocular disorders and diseases and, more specifically, dry macular degeneration (dry AMD).

What is claimed is:

1. A wearable device for delivery of photobiomodulation (PBM) to retinal tissue of an eye of a patient, the wearable device comprising:
   a frame comprising a front piece and at least one affixation element attached to the front piece, wherein the front piece is configured to be positioned in front of the eye of the patient;
   at least one first light source disposed within or on the at least one affixation element and configured to produce light in a first light beam having a first PBM wavelength comprising near infrared (NIR) light;
   at least one second light source disposed within or on the at least one affixation element and configured to produce light in a second light beam having a second PBM wavelength,
      wherein the second PBM wavelength differs from the first PBM wavelength by at least 25 nm, and
      wherein at least a portion of each of the first light beam and the second light beam is directed toward the front piece of the frame;
   a diffuser configured to homogenize the light in the first light beam or the second light beam, or in both the first light beam and the second light beam, such that an energy density profile of the light is evenly distributed among a range of emission angles; and
   at least one light directing element disposed within or on the front piece of the frame and configured to receive and redirect the at least a portion of each of the first light beam having the first PBM wavelength and the second light beam having the second PBM wavelength toward the retinal tissue of the eye of the patient when the patient is wearing the wearable device.

2. The wearable device of claim 1, further comprising at least one third light source disposed within or on the affixation element and configured to produce light in a third light beam having a third PBM wavelength,
  wherein the third PBM wavelength differs from the first PBM wavelength and the second PBM wavelength by at least 25 nm,
  wherein the diffuser is further configured to homogenize the light in the third light beam, and
  wherein at least a portion of the third light beam is directed toward the front piece of the frame to be redirected by the at least one light directing element toward the retinal tissue of the eye of the patient.

3. The wearable device of claim 2, wherein the first PBM wavelength is in a range from 800 to 900 nm, the second PBM wavelength is in a range from 600 to 700 nm, and the third PBM wavelength is in a range from 550 to 650 nm.

4. The wearable device of claim 1, wherein the first PBM wavelength is in a range from 800 to 900 nm and the second PBM wavelength is in a range from 600 to 700 nm.

5. The wearable device of claim 1, wherein the first PBM wavelength is in a range from 800 to 900 nm and the second PBM wavelength is in a range from 550 to 650 nm.

6. The wearable device of claim 1, wherein the first light beam has a PBM wavelength that produces a first therapeutic effect and the second light beam has a PBM wavelength that produces a second therapeutic effect that differs from the first therapeutic effect.

7. The wearable device of claim 1, wherein the at least one affixation element comprises an earpiece and the at least one light directing element comprises at least one reflector,
  wherein the at least one first light source and the at least one second light source are disposed within or on the earpiece and arranged to direct the light in the first and second light beams toward the at least one reflector, and
  wherein the at least one reflector is arranged to redirect at least a portion of the light in the first and second light beams toward the eye of the patient.

8. The wearable device of claim 7, wherein the at least one reflector comprises the diffuser configured to homogenize the light in the first and second light beams.

9. The wearable device of claim 7, wherein the at least one reflector is partially transparent.

10. The wearable device of claim 1, further comprising:
  a spatial light modulator disposed within or on the frame and positioned to receive the first and second light beams and to modulate the light in the first and second light beams to generate a modulated light beam;
  wherein the light directing element is configured to receive the modulated light beam and redirect at least a portion of the modulated light beam toward the eye of the patient when the patient is wearing the wearable device.

11. The wearable device of claim 1, further comprising an internal controller within or on the frame and coupled to the at least one first and second light sources to control production of the first and second light beams, wherein the internal controller is communicatively coupled to an external controller that is usable to program the internal controller to control operation of the at least one first and second light sources according to a predetermined treatment regimen.

12. The wearable device of claim 11, wherein the predetermined treatment regimen includes a set of activation times or periods during which each of the at least one first and second light sources is in an emitting state and a set of inactivation times or periods during which each of the at least one first and second light sources is in a non-emitting state.

13. The wearable device of claim 1, wherein the first and second light beams deliver light to the retinal tissue of the eye of the patient in at least two doses, wherein the first light beam in a first dose is predetermined to stimulate a first activity in the retinal tissue, and the second light beam in a second dose is predetermined to stimulate a second activity in the retinal tissue, wherein the second activity differs from the first activity.

14. The wearable device of claim 1, wherein the light in each of the first and second light beams has an irradiance at the retinal tissue that facilitates healing and/or reverses or slows disease progression in the retinal tissue.

15. A wearable device for delivery of photobiomodulation (PBM) to retinal tissue of an eye of a patient, the wearable device comprising:
  a frame comprising a front piece and at least one affixation element attached to the front piece, wherein the front piece is configured to be positioned in front of the eye of the patient;
  at least one light source disposed within or on the frame and configured to produce light in a light beam having a PBM wavelength;
  a diffuser configured to homogenize the light in the light beam, producing a uniform distribution of energy in the light;
  a spatial light modulator disposed within or on the frame and positioned to receive the light beam and to modulate the light in the light beam to generate a modulated light beam; and
  a light directing element within or on the frame to receive the modulated light beam and to redirect at least a portion of the modulated light beam toward the retinal tissue of the eye of the patient when the patient is wearing the wearable device.

16. The wearable device of claim 15, wherein the light directing element is a prism or a waveguide.

17. The wearable device of claim 15, wherein the at least one light source is disposed within or on the at least one affixation element, and the light directing element is disposed within or on the front piece of the frame.

18. The wearable device of claim 15, wherein the at least one light source comprises:
  at least one first light source configured to produce light in a first light beam having a first PBM wavelength; and
  at least one second light source configured to produce light in a second light beam having a second PBM wavelength, wherein the second PBM wavelength differs from the first PBM wavelength by at least 25 nm,
  wherein the diffuser is configured to homogenize the light in the first light beam and/or the second light beam.

19. The wearable device of claim 18, wherein the at least one light source further comprises:
  at least one third light source configured to produce light in a third light beam having a third PBM wavelength, wherein the diffuser is further configured to homogenize the light in the third light beam;
  wherein the third PBM wavelength differs from the first and second wavelengths by at least 25 nm.

20. A method of providing PBM to retinal tissue of a patient wearing the wearable device of claim 1, the method comprising:
placing the wearable device on the patient;
directing the light of the first PBM wavelength to the retinal tissue of the eye of the patient to produce a first therapeutic effect; and
directing the light of the second PBM wavelength from the wearable device to the retinal tissue of the eye of the patient to produce a second therapeutic effect that differs from the first therapeutic effect.

21. The method of claim 20, wherein the light of at least one of the first PBM wavelength or the second PBM wavelength is diffused through an eyelid of the patient before the light reaches the retinal tissue of the eye of the patient.

22. The method of claim 20, wherein the light of the first PBM wavelength and the light of the second PBM wavelength is diffused through an eyelid of the patient before the light reaches the retinal tissue of the eye of the patient.

23. The method of claim 22, wherein the directing the light comprises sequentially directing the light of the first PBM wavelength and the light of the second PBM wavelength from the wearable device to the retinal tissue of the eye of the patient.

24. The method of claim 22, wherein the directing the light comprises simultaneously directing the light of the first PBM wavelength and light of the second PBM wavelength from the wearable device to the retinal tissue of the eye of the patient.

25. A wearable device for delivery of photobiomodulation (PBM) to retinal tissue of an eye of a patient, the wearable device comprising:

a frame comprising a front piece and at least one affixation element attached to the front piece;

at least one first light source producing a first light beam having a first PBM wavelength comprising near infrared (NIR) light and disposed within or on the frame;

at least one second light source producing a second light beam having a second PBM wavelength and disposed within or on the frame, wherein the second PBM wavelength is in a range from 600 to 700 nm or is in a range from 550 to 650 nm; and a diffuser adapted to homogenize the light in the first light beam or the second light beam, or in both the first light beam and the second light beam, reducing non-uniformities in an energy density profile of the light, wherein at least a portion of each of the first light beam having the first PBM wavelength and the second light beam having the second PBM wavelength is directed toward the retinal tissue of the eye of the patient when the patient is wearing the wearable device.

26. The wearable device of claim 25, wherein the at least one affixation element comprises an earpiece and the frame further comprises at least one reflector disposed on the front piece, wherein the at least one first light source and the at least one second light source are disposed on the earpiece and arranged to direct the light in the first and second light beams toward the at least one reflector, wherein the at least one reflector is arranged to redirect at least a portion of the light in the first and second light beams toward the eye of the patient.

* * * * *